US012630546B2

(12) United States Patent
Oryan (Orian) et al.

(10) Patent No.: US 12,630,546 B2
(45) Date of Patent: May 19, 2026

(54) RNF4 TARGETING COMPOUNDS AND USES THEREOF

(71) Applicant: TECHNION RESEARCH & DEVELOPMENT FOUNDATION LIMITED, Haifa (IL)

(72) Inventors: Amir Oryan (Orian), Haifa (IL); Ashraf Brik, Haifa (IL); Yamen Abu Ahmad, Haifa (IL); Satish Gandhesiri, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 390 days.

(21) Appl. No.: 18/371,389

(22) Filed: Sep. 21, 2023

(65) Prior Publication Data

US 2024/0132486 A1 Apr. 25, 2024

Related U.S. Application Data

(63) Continuation of application No. PCT/IL2022/050328, filed on Mar. 24, 2022.

(60) Provisional application No. 63/165,843, filed on Mar. 25, 2021.

(51) Int. Cl.
*C07D 417/12* (2006.01)
*A61P 35/00* (2006.01)

(52) U.S. Cl.
CPC ........... *C07D 417/12* (2013.01); *A61P 35/00* (2018.01)

(58) Field of Classification Search
None
See application file for complete search history.

(56) References Cited

FOREIGN PATENT DOCUMENTS

WO WO-2018223909 A1 * 12/2018 ......... C07K 5/06034
WO 2020076996 A1 4/2020

OTHER PUBLICATIONS

Lenos, K. J. (Dec. 21, 2011). Functions and regulation of Hdmx and post-translational modifications in drug sensitivity and cancer. Retrieved from: [https://hdl.handle.net/1887/18267].

Paiva SL, Crews CM. Targeted protein degradation: elements of PROTAC design. Curr Opin Chem Biol. Jun. 2019;50:111-119. doi: 10.1016/j.cbpa.2019.02.022. Epub Apr. 17, 2019. PMID: 31004963; PMCID: PMC6930012.

Rojas-Fernandez A, Plechanovová A, Hattersley N, Jaffray E, Tatham MH, Hay RT. SUMO chain-induced dimerization activates RNF4. Mol Cell. Mar. 20, 2014;53(6):880-92. doi: 10.1016/j.molcel.2014.02.031. PMID: 24656128; PMCID: PMC3991395.

Steinebach, Christian, et al. "PROTAC-mediated crosstalk between E3 ligases." Chemical Communications, 55.12 (2019): 1821-1824. First published: Jan. 16, 2019. DOI: 10.1039C8CC09541H.

(Continued)

*Primary Examiner* — Jeffrey S Lundgren
*Assistant Examiner* — Anthony Joseph Seitz
(74) *Attorney, Agent, or Firm* — The Roy Gross Law Firm, LLC; Roy D. Gross

(57) ABSTRACT

The present invention provides compounds and pharmaceutical compositions comprising thereof. Further, methods for treating or preventing development of a RNF4 related disorder in a subject in need thereof are also provided.

17 Claims, 22 Drawing Sheets
(11 of 22 Drawing Sheet(s) Filed in Color)

(56) References Cited

OTHER PUBLICATIONS

Ward CC, Kleinman JI, Brittain SM, Lee PS, Chung CYS, Kim K, Petri Y, Thomas JR, Tallarico JA, McKenna JM, Schirle M, Nomura DK. Covalent Ligand Screening Uncovers a RNF4 E3 Ligase Recruiter for Targeted Protein Degradation Applications. ACS Chem Biol. Nov. 15, 2019;14(11):2430-2440. doi: 10.1021/acschembio.8b01083. Epub May 13, 2019. PMID: 31059647; PMCID: PMC7422721.

Galdeano C, Gadd MS, Soares P, Scaffidi S, Van Molle I, Birced I, Hewitt S, Dias DM, Ciulli A. Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem. Oct. 23, 2014;57(20):8657-63. doi: 10.1021/jm5011258. Epub Oct. 6, 2014. PMID: 25166285; PMCID: PMC4207132.

Zhao Q, Ren C, Liu L, Chen J, Shao Y, Sun N, Sun R, Kong Y, Ding X, Zhang X, Xu Y, Yang B, Yin Q, Yang X, Jiang B. Discovery of SIAIS178 as an Effective BCR-ABL Degrader by Recruiting Von Hippel-Lindau (VHL) E3 Ubiquitin Ligase. J Med Chem. Oct. 24, 2019;62(20):9281-9298. doi: 10.1021/acs.jmedchem.9b01264. Epub Oct. 2, 2019. PMID: 31539241.

PCT International Search Report for International Application No. PCT/IL2022/050328, mailed Jul. 10, 2022, 3pp.

PCT Written Opinion for International Application No. PCT/IL2022/050328, mailed Jul. 10, 2022, 10pp.

* cited by examiner

Benign mole
Negative melanoma
Positive melanoma
High RNF4
Low RNF4
Overall Survival (days)

c-Myc
c-Myc$^{S62A}$
c-Myc
RNF4
Actin
RNF4 - - + + - - + +
Chase(min) 0 35 0 35 0 35 0 35
(%)c-Myc 100 25 100 157 100 30 100 15 c-Myc$^{T58A}$
c-Myc$^{S62A}$
c-Myc
hRNF4
Actin
hRNF4 - + - +

$^{35}$S-Hairy
$^{35}$S-c-Myc
$^{35}$S-c-Myc$^{S62A}$
input
GST
GST-RNF4

$^{35}$S-c-Myc
-CIP
+CIP
input
GST
GST-RNF4 c-Myc
c-Myc$^{S62A}$
IP: Ni-NTA beads
WB: α c-Myc
c-Myc
Ub$_n$-c-Myc conjugates

M.W. (kDa)
245
180
135
100
75
63
48
35
25
WB: α Ub
Ub$_n$-conjugates
RNF4
Actin
RNF4 - + - +

R4VP

R = alkyl, $NO_2$, $CF_3$ n = 1 to 5

R = halogen, alkyl, acetyl, $NO_2$, $CF_3$

A375R cells

Figure 12A

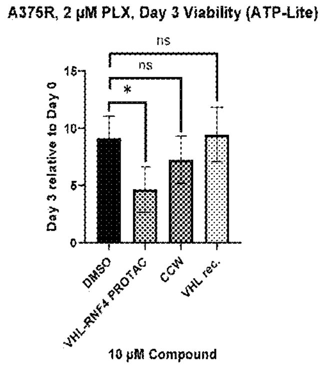

| Bonferroni's multiple comparisons test | Significant? | Summary | Adjusted P Value |
|---|---|---|---|
| DMSO vs. VHL-RNF4 PROTAC | Yes | * | 0.0329 |
| DMSO vs. CCW | No | ns | 0.6967 |
| DMSO vs. VHL rec. | No | ns | >0.9999 |

Figure 12B

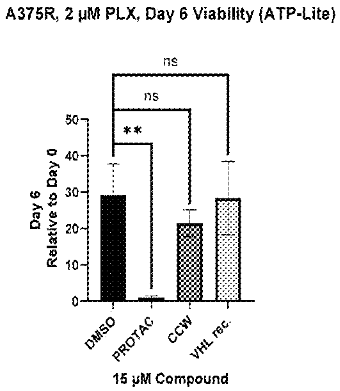

One-Way ANOVA

| Bonferroni's multiple comparisons test | Summary | Adjusted P Value |
|---|---|---|
| DMSO vs. PROTAC | ** | 0.0024 |
| DMSO vs. CCW | ns | 0.1004 |
| DMSO vs. VHL rec. | ns | >0.9999 |

Figure 12C

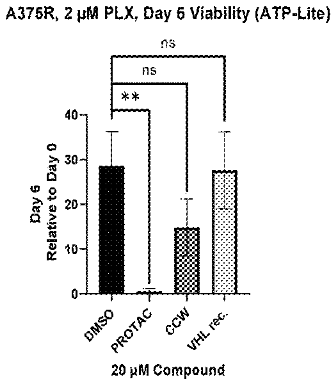

One-Way ANOVA

| Bonferroni's multiple comparisons test | Summary | Adjusted P Value |
|---|---|---|
| DMSO vs. PROTAC | ** | 0.0024 |
| DMSO vs. CCW | ns | 0.1004 |
| DMSO vs. VHL rec. | ns | >0.9999 |

RNF4 TARGETING COMPOUNDS AND USES THEREOF

CROSS REFERENCE TO RELATED APPLICATIONS

This application is a Bypass Continuation of PCT Patent Application No. PCT/IL2022/050328 having International filing date of Mar. 24, 2022, which claims the benefit of priority from U.S. Provisional Patent Application No. 63/165,843, filed Mar. 25, 2021, entitled: RNF4 TARGETING COMPOUNDS AND USES THEREOF. The contents of the above applications are all incorporated herein by reference as if fully set forth herein in their entirety.

FIELD OF THE INVENTION

The present invention is in the field of cancer therapy.

BACKGROUND OF THE INVENTION

Cancer is intimately linked to deregulated proteolysis. Deregulated and increased oncoprotein stabilization is at the heart of tumorigenesis. Moreover, the development of resistance to chemotherapy and molecular treatments is associated with increased oncoprotein stabilization.

RING finger protein 4 (RNF4) belongs to a small group of RING ubiquitin ligases termed SUMO-Targeted Ubiquitin ligases (STUbL). In many cases, ubiquitylation by RNF4 leads to proteasomal degradation of SUMOylated proteins. Recent findings show that in the case of epithelial cancers, melanoma, and osteosarcoma, phosphorylation-dependent, RNF4-mediated ubiquitylation potentiates tumorigenic properties of cancer cells by stabilizing a subset of oncoproteins. While RNF4 is non-oncogenic on its own, it has been shown that it is essential for cancer cells to cope with oncogenic stress. Genes, such as RNF4 are collectively termed "Non-Oncogenic Addiction" genes (NOA), are viewed as the "Achilles' heel" of tumors, thus are potentially excellent targets for personalized therapy. There is a need for development of efficient inhibitors of RNF4 as a novel strategy for eradicating therapy-resistant cancers.

SUMMARY OF THE INVENTION

In one aspect of the invention, there is provided a compound, a salt, an isomer or a tautomer thereof, wherein the compound is represented by Formula I:

(I)

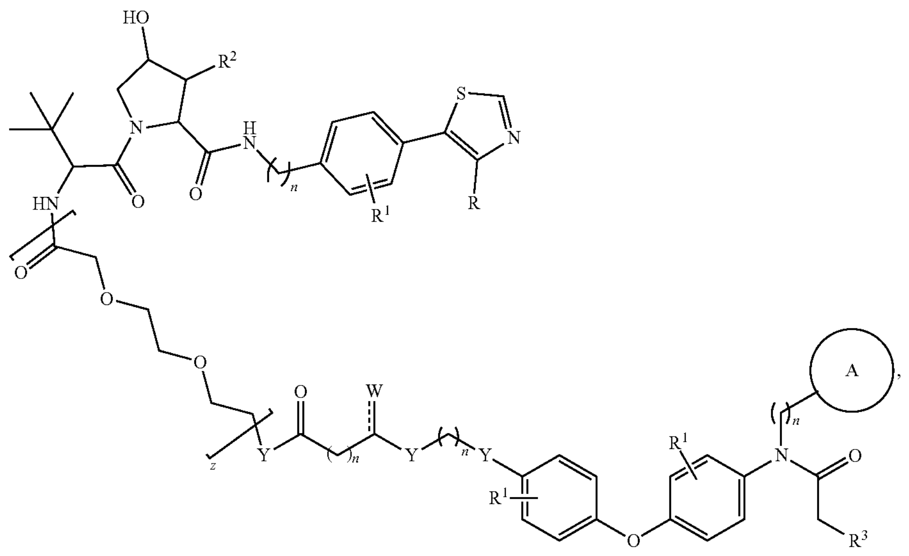

wherein:

each Y independently is selected from the group consisting of: NH, S, O and CH; ----- represents a single bond or a double bond; W is selected from the group consisting of: H, NH, $NH_2$, S, SH, O, OH, $CH_2$ and CH; each n independently represents an integer in a range from 1 to 10; z represents an integer in a range from 0 to 6; R, $R^2$ and $R^3$ each independently represents hydrogen, a hydroxy group, a methyl group, or a halo group; each $R^1$ independently is selected from the group consisting of: a methyl group, an isopropyl group, a tent-butyl group, a ($C_2$-$C_{10}$) alkyl group, a substituted ($C_2$-$C_{10}$) alkyl group, a cycloalkyl group, an alkyne group, a substituted alkyne group, an alkylhydroxy group, an alkoxy group, an hydroxy group, a phenoxy group, a methoxy group, a carboxy group, a keto group, a halo group, a haloalkyl group, a nitro group, a cyano group, an amino group, an amide group, a thioalkoxy group, a thioalkyl group, a thiohydroxy group, trihalomethyl group, a sulfonyl group, a sulfoxy group, a sulfinyl group, a sulfonamide group, and any combination thereof; and A represents an aryl, a substituted aryl, a heteroaryl, a substituted heteroaryl, a $C_3$-$C_8$ cycloalkyl, a substituted $C_3$-$C_8$ cycloalkyl, an alkaryl, a substituted alkaryl, a bicyclic aromatic ring, a substituted bicyclic aromatic ring, a bicyclic heteroaryl, a substituted bicyclic heteroaryl, a bicyclic heterocyclyl, a substituted bicyclic heterocyclyl, a bicyclic cycloalkyl, a substituted bicyclic cycloalkyl, or a combination thereof.

In some embodiments, A comprises any of:

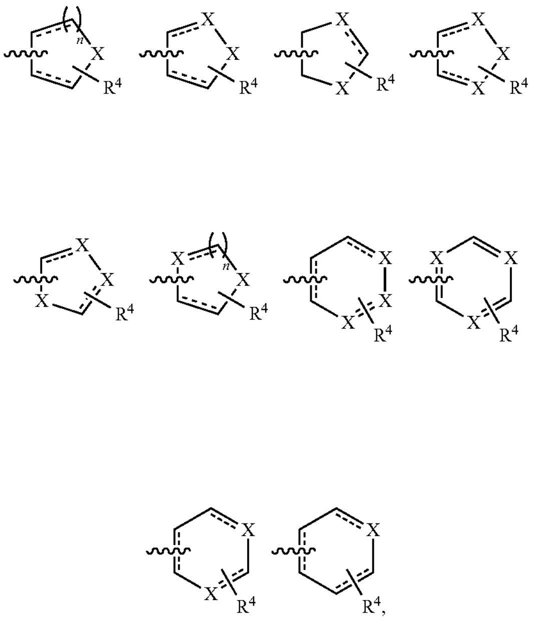

wherein: each X independently represents CH, C, N, NH, S or O; n is 1 or 2; and $R^4$ is absent or selected from the group consisting of: a methyl group, an isopropyl group, a tert-butyl group, a ($C_2$-$C_{10}$) alkyl group, a substituted ($C_2$-$C_{10}$) alkyl group, a cycloalkyl group, an alkyne group, a substituted alkyne group, an alkylhydroxy group, an alkoxy group, an hydroxy group, a phenoxy group, a methoxy group, a carboxy group, a keto group, a halo group, a haloalkyl group, a nitro group, a cyano group, an amino group, an amide group, a thioalkoxy group, a thioalkyl group, a thiohydroxy group, trihalomethyl group, a sulfonyl group, a sulfoxy group, a sulfinyl group, a sulfonamide group, and any combination thereof.

In some embodiments, the A comprises any one of:

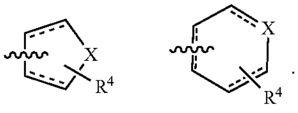

In some embodiments, the z represents an integer in a range from 0 to 3.

In some embodiments, the compound is represented by Formula II:

(II)

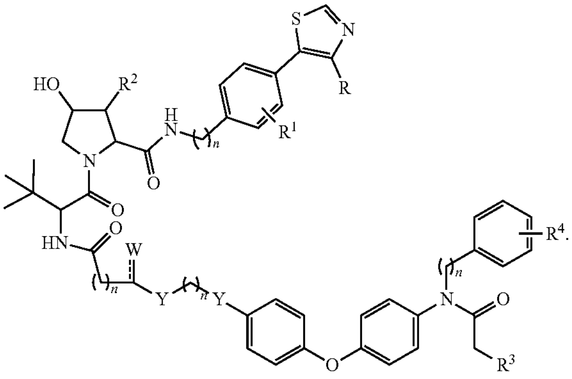

In some embodiments, the compound is represented by Formula III:

(III)

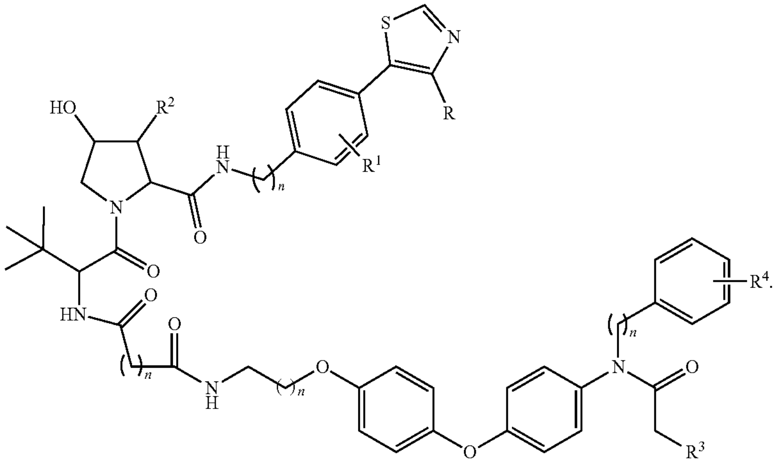

In some embodiments, the compound is represented by Formula IV:

(IV)

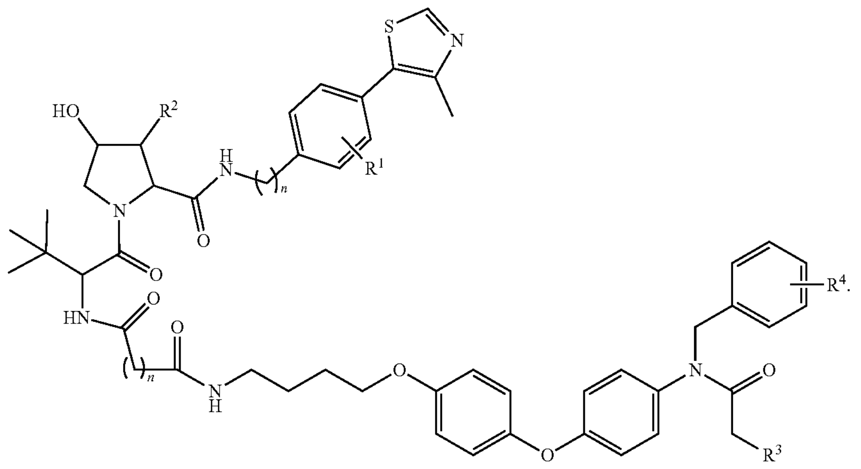

In some embodiments, each of the n independently represents an integer in a range from 1 to 5.

In some embodiments, the $R^1$ is selected from the group consisting of: a methyl group, an isopropyl group, a tent-butyl group, a ($C_2$-$C_{10}$) alkyl group, a substituted ($C_2$-$C_{10}$) alkyl group, a cycloalkyl group, a phenoxy group, a methoxy group, a carboxy group, a nitro group, and a trihalomethyl group.

In some embodiments, the $R^2$ is a halo group.

In some embodiments, the $R^4$ is selected from the group consisting of: a methyl group, an isopropyl group, a tert-butyl group, a ($C_2$-$C_{10}$) alkyl group, a substituted ($C_2$-$C_{10}$) alkyl group, an amino group (e.g. —NRR, wherein each R is independently elected from H or a $C_1$-$C_{10}$ alkyl group, optionally substituted by one or more R4; or wherein the amino group is a cyclic amine, wherein both R are interconnected so as to form a cyclyl), a phenoxy group, a methoxy group, a halo group, a haloalkyl group, a nitro group, and a trihalomethyl group.

In some embodiments, the compound is:

In another aspect, there is provided a pharmaceutical composition comprising the compound of the present invention, and an acceptable carrier.

In some embodiments, the pharmaceutical composition is for use in the inhibition of Ring Finger Protein 4 (RNF4).

In some embodiments, the pharmaceutical composition is for use in the prevention or treatment of a disorder associated with cancer, inflammatory disorder, autoimmune disorder, or viral infection.

In some embodiments, the cancer is selected from the group consisting of: melanoma, squamous cell carcinoma breast cancer, colorectal cancer, osteosarcoma, lung cancer, ovarian cancer, prostate cancer, pancreatic cancer and hematological cancers.

In another aspect, there is provided a method for treating or preventing development of a RNF4 related disorder, in a subject in need thereof, comprising administering to the subject a therapeutically effective amount the pharmaceutical composition of the present invention.

In some embodiments, the disorder is selected from the group comprising: cancer, inflammatory disorder, autoimmune disorder, or viral infection.

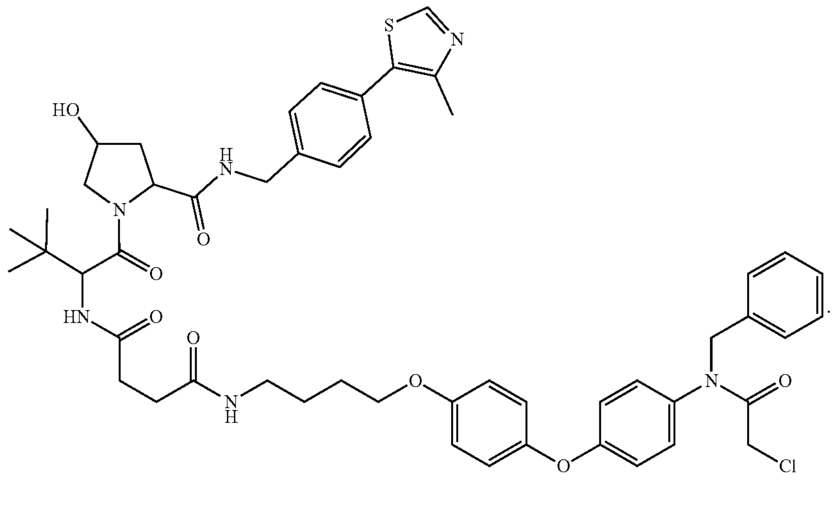 [SMILES: Cc1ncsc1-c1ccc(CNC(=O)C2CC(O)CN2C(=O)C(NC(=O)CCC(=O)NCCCCOc2ccc(Oc3ccc(N(Cc4ccccc4)C(=O)CCl)cc3)cc2)C(C)(C)C)cc1]

In some embodiments, the cancer is selected from the group consisting of: melanoma, squamous cell carcinoma breast cancer, colorectal cancer, osteosarcoma, lung cancer, ovarian cancer, prostate cancer, pancreatic cancer and hematological cancers.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 2A-O include micrographs and graphs showing that RNF4 mRNA and protein levels are elevated in human melanoma and correlate with poor survival. Immunohistochemistry of patient-derived biopsies of nevi (FIGS. 2A-B), and melanoma tumors (FIGS. 2C-K) (H&E x40). RNF4 was identified using 810D mAb (red). A negative melanoma biopsy (FIGS. 2C-D), and positive biopsies (FIGS. 2E-L). FIGS. 2B, 2D, 2F, 2H, 2J and 2L, are higher magnification (H&E x400). Insets are higher magnification of the regions in the dashed squares. Scale bar is 50 μm. (FIG. 2M) Quantification of positive cells in each biopsy. (FIGS. 2N-O) Kaplan-Meier overall survival curves of melanoma patients, stratified according to RNF4 mRNA, (n; n=330, p<0.05) and protein (o; n=28 p; ns, likely due to small size of the TMA) levels. In both panels Low RNF4 is shown in blue and High RNF4 in red;

(FIG. 4A) Western blot analysis of the indicated proteins derived from PLX4032-sensitive (A375) or PLX4032-resistant human A375R cells. (FIG. 4B) Expression of RNF4 in A375 cells induces resistance to PLX4032 (Vemurafenib). A375 Cells were infected with Dox-inducible RNF4-coding viruses. Cell viability was monitored in the absences or presence of Dox and treatment with PLX4032 at the indicated concentrations for six days, n=3. (FIG. 4C) shRNF4-medeiated knockdown of RNF4 resulted in reduced viability of A375R cells as measured by MTT assay. A375R cells were infected with the indicated shRNA and PLX4032 concentrations. Cell viability was determined six days post-infection. (FIG. 4D) Colony formation of A375R cells infected with the indicated vectors, in the presence of PLX4032 at 5 μM. Expression of eIF2α but not of FLAG vector, in shRNF4-expressing A375R cells partially restores sensitivity to PLX4032. (FIG. 4E) Quantification of colonies number shown in (FIG. 4D), n=3. (FIG. 4F) Size of A375R xenograft mouse tumors expressing either scRNA control or shRNF4 in the presence of PLX4072. ****=P<0.0001 (FIGS. 4G-I) High RNF4 mRNA level correlates with resistance to RTK therapy (see methods). (FIG. 4G) Boxplot depict RNF4 mRNA expression in melanoma samples at time of pre-treatment comparing responders to none responders, n=15. (FIG. 4H) Reduction in tumor size upon treatment for individual patients shown in (FIG. 4G). (FIG. 4I) comparison of RNF4 mRNA levels between pre-treatment and upon disease progression. Blue lines denote increase of RNF4 expression in upon progression while red lines denote decrease (n=12, paired Wilcoxon Ranksum P<0.02);

(FIG. 5A) $c\text{-}Myc^{S62A}$ mutant is not stabilized by the expression of RNF4 in dynamic cycloheximide chase experiment. (FIG. 5B) Thr58 that is required for c-Myc degradation is not required for RNF4-dependent stabilization. (FIGS. 5C-D) In vitro translated (IVT) labeled $^{35}S$-Met-Hairy and $^{35S}$ -Met-c-Myc bind to GST-RNF4, while $^{35}S$ -Met-$c\text{-}Myc^{S62A}$ binds weakly to GST-RNF4. (FIG. 5D) Mock-treated but not CIP-treated $^{35}S$-Met-c-Myc (FIG. 5B), bind to GST-RNF4 (CIP, Calf Intestinal Phosphatase). In FIGS. 5C-D, 5% input is shown and no binding is detected for GST alone. (FIGS. 5E-F) RNF4 ubiquitylates c-Myc but not $c\text{-}Myc^{S62A}$. (FIG. 5E) RNF4 ubiquitylates c-Myc but not $c\text{-}Myc^{S62A}$ in HEK293T cells. (FIG. 5F) overall ubiquitylation determined using a α-Ub antibody;

(FIG. 6A) Schematic diagram of hRNF4 (not to scale): SIM, SUMO-interacting motif; ARM, Arginine Rich Motif; RING, Really Interesting Gene; NTR, nucleosome targeting region. (FIG. 6B) Left panel: in vitro translated (IVT) c-Myc bind to GST-RNF4 but not to $GST\text{-}RNF4^{\Delta RM}$. Right panel: Protein levels of the GST-fusion proteins. (FIGS. 6C-D) β-catenin (FIG. 6C), and c-Myc (FIG. 6D), Luciferase reporter assays in HEK293T cells transfected with the indicated plasmids Lower panels: western blot analyses of steady-state levels of β-catenin, c-Myc, and RNF4 in representative extracts. (FIG. 6E) RNF4, but not catalytically inactive $RNF4^{C159A}$, enhances Delta-dependent Notch-induced activation of the TP1-Luciferase-Notch reporter in a co-culture assay. (FIG. 6F) RNF4-stabilizes Notch intracellular domain protein (N-ICD). $^{35}$S-Met pulse chase analysis of FLAG-NICD in MK4 cells expressing indicated plasmids followed by α-Flag-IP;

(FIG. 7A) c-Myc stabilization by RNF4 requires K11/K33 ubiquitin. Where indicated, cells were transfected with HA-tagged wild-type ubiquitin, or mutants where a specific Lys was replaced by Arg (K #R). K0 is a ubiquitin molecule in which all internal Lys residues were replaced with Arg. Lower panel: quantitation of the effect of ubiquitin mutants on RNF4-dependent c-Myc stabilization using 9E10 antibody (Data shown are mean±SE, n=6). Expression of c-Myc (FIG. 7B upper panel) and β-catenin (FIG. 7B lower panel), in cells transfected with, where indicated, RNF4 and the ubiquitin mutants. UbK11* and UbK33 * are mutant ubiquitin molecules that contain a single lysine where all other lysine residues are replaced with Arg. Fold: relative change in c-Myc and β-catenin protein levels. (FIG. 7C). Co-expression of K11* and K33* within ubiquitin is sufficient for RNF4-dependent Myc ubiquitylation. Total ubiquitylation is shown in lower panel. (FIG. 7D) Expression of Fbw7 ligase subunit reduces c-Myc protein levels in control and RNF4-expressing cells, suggesting that RNF4 stabilization does not inhibit Fbw7-dependent degradation of c-Myc;

(FIGS. 9A-E) blue color indicates an RNF4-interactor-based recruiter, red color indicates a VHL-recruiter-based degrader, and black color indicates the linker. (FIG. 9A) Structure of R4VP that was used in all experiments shown below in FIGS. 11-15. (FIGS. 9B-E) The inventors designed modified versions of R4VP;

FIGS. 12A-C show that RNF4-VHL-PROTAC (R4VP) inhibits A375R proliferation. Viability of A375R melanoma cells as determined by MTT assay. Cells were grown in the presence of 2 mM of PLX 4032 treated with the indicated compounds for six days at the indicated concentration **=p<0.01 ns: non-significant; n=3; CCW-RNF4 binding molecule only; VHL-rec, VHL recruiter molecule only.

FIG. 16A is a bar measuring indirectly cell viability using MTT assays of mouse melanoma B16F10 cancer cells. The cells were treated with the indicated doses of the indicated PROTACs [(VHL-only PROTAC or RNF4-VHL (R4VP)] for three days, and viability was determined compared to control (DMSO). FIG. 16B is a bar representing viability of B16F10 cells in three independent biological repeats where cells were treated for three days with the indicated PROTACS. One-way analysis of ANOVA (n=3, ****=p<0.001)

FIG. 17A presents FACS analysis of control (untreated) A375R melanoma cells, and FIG. 17B presents FACS analysis of A375R melanoma cells three hours after the exposure to 20 uM RNF4-VHL-PROTAC.

As shown in FIG. 18C, both cell lines express RNF4 protein. Thus, R4VP PROTAC has a selective activity against tumorigenic cancer cells.

DETAILED DESCRIPTION OF THE INVENTION

Figures 1A, 1B, 1C:
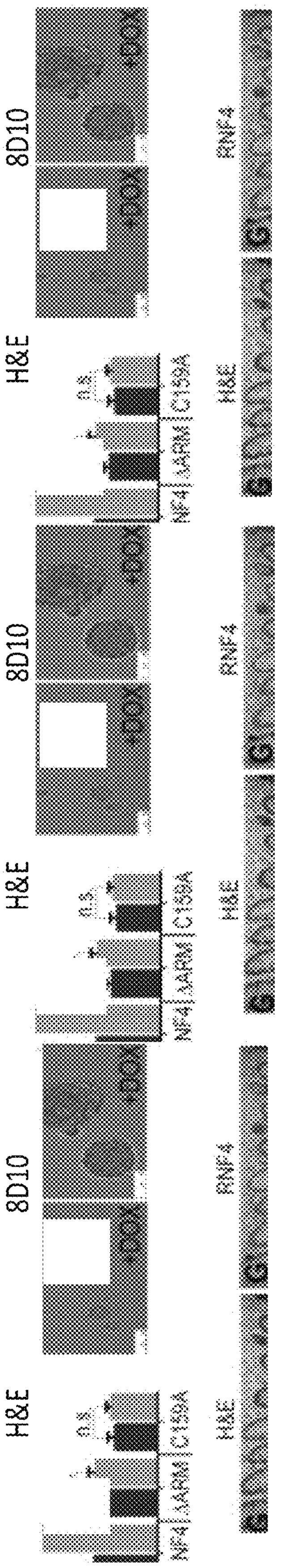
FIGS. 1A-C' include micrographs showing that RNF4 is highly expressed in colon tumors. High levels of RNF4 protein are observed in 30% of patient-derived of carcinoma (FIGS. 1C and 1C') in the cancerous part of high-grade adenoma (CIS adenoma, FIGS. 1B and 1B') but not in benign adenoma (FIGS. 1A and 1A'). ' in the Figure number indicates Hematoxylin Eosin staining (H&E). 8D10 is a mAb anti RNF4 we generated, (n=99)

According to some embodiments, the present invention provides a compound, a salt, an isomer or a tautomer thereof, wherein the compound is represented by Formula I shown hereinbelow.

The present invention is directed compounds and compositions comprising the compounds. In some embodiments, the compounds are Ring Finger Protein 4 (RNF4) inhibitors.

In some embodiments, the compounds bind RNF4 and prevent it from stabilizing oncogenic substrates. In some embodiments, the compounds and compositions of the present invention are used in methods for treating or preventing development of a RNF4 related disorder. In some embodiments, the compounds and compositions of the present invention are used in methods for preventing tumor potentiating activity of RNF4, thereby reducing and/or inhibiting cancer cell proliferation and tumorigenic properties of cancer cells such as colony formation.

In some embodiments, the compounds of the present invention are proteolysis targeting chimera (PROTAC).

As used herein, the term "proteolysis targeting chimera (PROTAC)" refers to a heterobifunctional small molecule composed of two active domains associated by a linker capable of removing specific unwanted proteins. PROTACs consist of two covalently linked protein-binding molecules: one capable of engaging an E3 ubiquitin ligase, and another that binds to a target protein meant for degradation.

The term "linker" as used herein, refers to a chemical moiety utilized to attach one part of a compound of interest to another compound of interest.

As used herein, the term "small molecule" refers to a non-peptidic, non-oligomeric organic compound. Small molecules can be either synthesized in the laboratory or found in nature. In some embodiments, a small molecule is characterized in that it contains several carbon-carbon bonds, and has a molecular weight of less than 2000 g/mol, preferably less than 1500 g/mol. In some embodiments, small molecules according to the present invention are synthetic small molecules.

In some embodiments, the compounds of the present invention bind to an E3-ubiquitin ligase. In some embodiments, the E3-ubiquitin ligase is Von-Hipple Landau (VHL) ubiquitin ligase. In some embodiments, the compounds of the present invention bind to RNF4. In some embodiments, the compounds of the present invention are characterized by inducing degradation of the target protein RNF4.

Compounds

According to an aspect of embodiments of the invention there is provided a compound, a salt, an isomer or a tautomer thereof, wherein the compound is represented by Formula I:

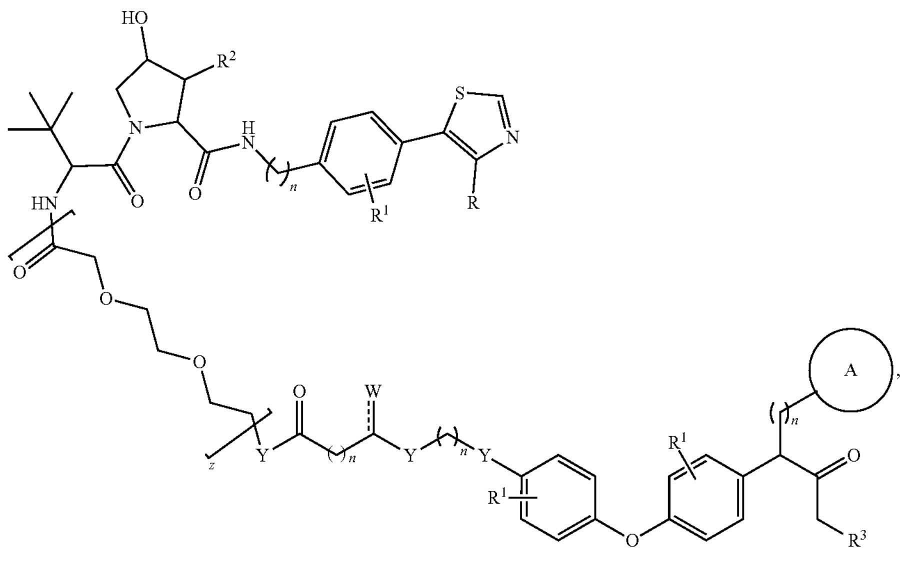

wherein:

each Y independently is selected from the group consisting of: NH, S, O and CH; ----- represents a single bond or a double bond; W is selected from the group consisting of: H, NH, $NH_2$, S, SH, O, OH, $CH_2$ and CH as allowed by valency; each n independently represents an integer in a range from 1 to 10 (e.g. 1, 2, 3, 4, 5, 6 7, 8, 9, or 10, or between 1-5, 1-3, 3-5, 1-6, 1-8, 1-9, 5-10, 5-7, 7-10, 3-10, 1-4, 1-7, including any range between); z represents an integer in a range from 0 to 6; R, $R^2$ and $R^3$ each independently represents hydrogen, or one or more substituents each substituent is independently selected from: a hydroxy group, a methyl group, or a halo group, or any combination thereof; each $R^1$ is H or represents one or more substituents each substituent is independently selected from: a methyl group, an isopropyl group, a tent-butyl group, a ($C_2$-$C_{10}$) alkyl group, a substituted ($C_2$-$C_{10}$) alkyl group, a cycloalkyl group, an alkyne group, a substituted alkyne group, an alkylhydroxy group, an alkoxy group, an hydroxy group, a phenoxy group, a methoxy group, a carboxy group, a keto group, a halo group, a haloalkyl group, a nitro group, a cyano group, an amino group, an amide group, a thioalkoxy group, a thioalkyl group, a thiohydroxy group, trihalomethyl group, a sulfonyl group, a sulfoxy group, a sulfinyl group, a sulfonamide group, and any combination thereof; and A represents an aryl, a substituted aryl, a heteroaryl, a substituted heteroaryl, a $C_3$-$C_8$ cycloalkyl, a substituted $C_3$-$C_8$ cycloalkyl, an alkaryl, a substituted alkaryl, a bicyclic aromatic ring, a substituted bicyclic aromatic ring, a bicyclic heteroaryl, a substituted bicyclic heteroaryl, a bicyclic heterocyclyl, a substituted bicyclic heterocyclyl, a bicyclic cycloalkyl, a substituted bicyclic cycloalkyl, or a combination thereof. In some embodiments, R1 is hydrogen.

In some embodiments, the compound is represented by Formula Ia:

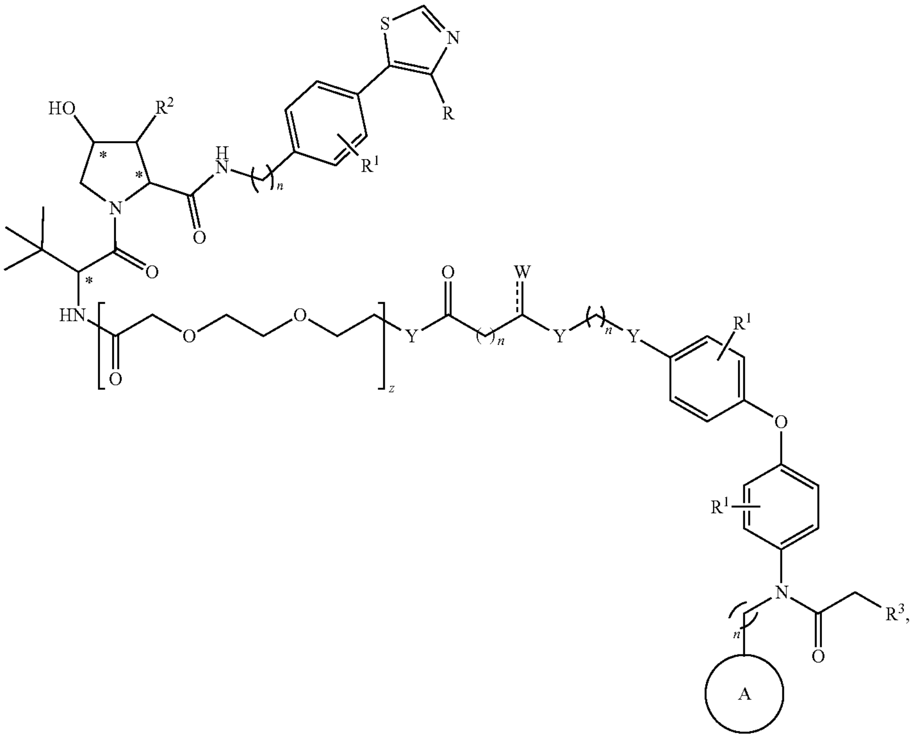

wherein each * is referred to any of R or S enantiomers or a mixture thereof.

In some embodiments, the compound is represented by Formula Ib:

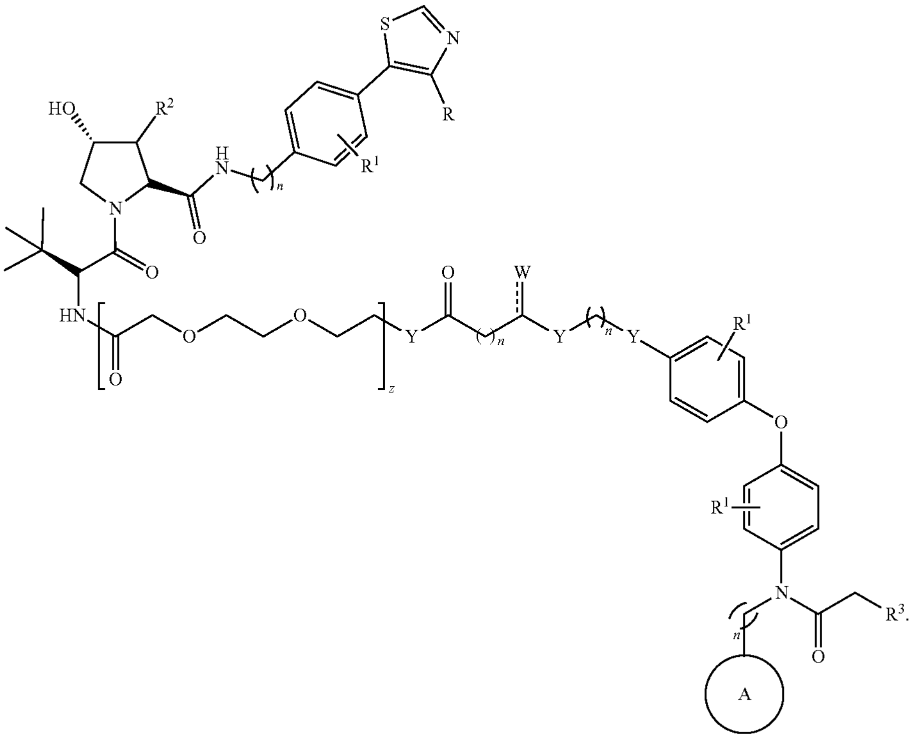

In some embodiments, z represents an integer in a range from 0 to 3.

In some embodiments, A comprises an aliphatic (C3-C10) ring, a substituted aliphatic (C3-C10) ring, an aromatic (C5-C10) ring, a substituted aromatic (C5-C10) ring or a combination thereof. In some embodiments, A comprises an aliphatic (C3-C8) ring, an aromatic (C5 or a C6) ring, a bicyclic aliphatic (C5-C20) ring, a bicyclic aromatic (C6-C20) ring, or a combination thereof, wherein each ring is optionally substituted. In some embodiments, A is devoid of an unsubstituted ring.

As used herein the term "(C3-C10) ring" is referred to an optionally substituted C3, C4, C5, C6, C7, C8, C9 or C10 aliphatic ring, aromatic ring, or a ring comprising an unsaturated bond. In some embodiments, (C3-C10) ring comprises optionally substituted cyclopropane, cyclobutene, cyclopentane, cyclohexane, or cycloheptane.

In some embodiments, A is a C5 or C6 heteroaryl (e.g. pyrrole, furan, thiophene, thiazole, pyrazole, isothiazole, imidazole, etc.)

In some embodiments, A is a fused heterocyclic ring (e.g. indole, isoindole, benzofuran, benzothiophene, benzotriazole, quinoline, chromene, chroman, quinazoline).

In some embodiments, A is a phenyl optionally substituted with one or more $R^4$ as described hereinbelow. In some embodiments, A comprises an alkaryl (such as benzyl) optionally substituted with one or more $R^4$ as described hereinbelow.

In some embodiments, A is attached via a carbon atom. In some embodiments, A is attached via a nitrogen atom.

In some embodiments, A comprises a phenyl, furan, pyridine, pyrazine, pyrrole, imidazole, pyrazole, oxazole, thiophene, or thiazole.

In some embodiments, A comprises any of:

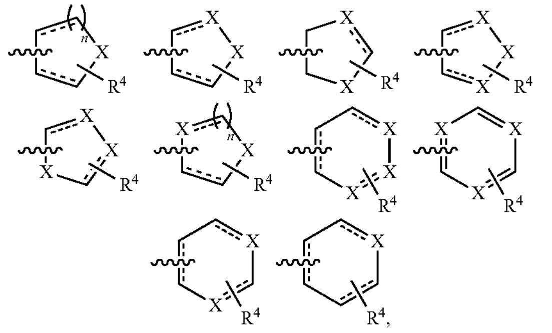

Wherein a wavy bond represents an attachment point, each X independently represents CH, C, N, NH, S or O; n is 1 or 2; and $R^4$ is absent or selected from the group consisting of: a methyl group, an isopropyl group, a tent-butyl group, a ($C_2$-$C_{10}$) alkyl group, a substituted ($C_2$-$C_{10}$) alkyl group, a cycloalkyl group, an alkyne group, a substituted alkyne group, an alkylhydroxy group, an alkoxy group, an hydroxy group, a phenoxy group, a methoxy group, a carboxy group, a keto group, a halo group, a haloalkyl group, a nitro group, a cyano group, an amino group (e.g. —NRR, wherein each R is independently elected from H or a $C_1$-$C_{10}$ alkyl group, optionally substituted by one or more R4; or wherein the amino group is a cyclic amine, wherein both R are interconnected so as to form a cyclyl), an amide group, a thioalkoxy group, a thioalkyl group, a thiohydroxy group, trihalomethyl group, a sulfonyl group, a sulfoxy group, a sulfinyl group, a sulfonamide group, and any combination thereof. In some embodiments, $R^4$ is H or represents one or more substituents each substituent is independently selected from: —$NO_2$, —CN, —OH, —$CONH_2$, —$CONR'_2$, —$CNNR'_2$, —$CSNR'_2$, —CONH—OH, —CONH—$NH_2$, —NHCOR', —NHCSR', —NHCNR', —NC(═O)R', —NC(═O)OR', —NC(═O)NR', —NC(═S)OR', —NC(═S)NR', —$SO_2R'$, —SOR', —SR', —$SO_2OR'$, —$SO_2N(R')_2$, —$NHNR'_2$, —NNR', carbonyl, $C_1$-$C_{10}$ haloalkyl, optionally substituted $C_1$-$C_{10}$ alkyl, —$NH_2$, —NH($C_1$-$C_{10}$ alkyl), —N($C_1$-$C_{10}$ alkyl)$_2$, $C_1$-$C_{10}$ haloalkoxy, hydroxy($C_1$-$C_{10}$ alkyl), hydroxy($C_1$-$C_{10}$ alkoxy), alkoxy($C_1$-$C_{10}$ alkyl), alkoxy($C_1$-$C_{10}$ alkoxy), amino($C_1$-$C_{10}$ alkyl), —CONH($C_1$-$C_{10}$ alkyl), —CON($C_1$-$C_{10}$ alkyl)$_2$, —$CO_2H$, —$CO_2R'$, —OCOR', —C(═O)R', —OC(═O)OR', —OC(═O)NR', —OC(═S)OR', —OC(═S)NR', a heteroatom, cycloalkyl, heterocyclyl, aryl, heteroaryl, ($C_1$-$C_{10}$ alkyl)alkyl-cycloalkyl, ($C_1$-$C_{10}$ alkyl)alkyl-aryl, ($C_1$-$C_{10}$ alkyl)alkyl-heteroaryl, or any combination thereof, and wherein each of cycloalkyl, heterocyclyl, aryl, heteroaryl is substituted or non-substituted, including any combination thereof; and each R' is independently H or comprises an optionally substituted $C_1$-$C_{10}$ alkyl, an $C_1$-$C_{10}$ alkyl-aryl, an $C_1$-$C_{10}$ alkyl-cycloalkyl, optionally substituted $C_3$-$C_{10}$ cycloalkyl, optionally substituted $C_3$-$C_{10}$ heterocyclyl, optionally substituted heteroaryl, optionally substituted aryl or a combination thereof.

In some embodiments, the term "cyclyl" comprises an aryl, a polycyclyl, a heteroaryl, a cycloalkyl, or heterocyclyl or any combinations thereof.

In some embodiments, the term "polycyclic ring" or "polycyclyl" encompasses a plurality (e.g. 2, 3, 4, 5 or 6) of fused or adjacent rings (e.g. biaryl or bicyclohexyl), wherein each ring is independently selected from aryl, heteroaryl, an optionally unsaturated cycloalkyl, an optionally unsaturated heterocyclyl, or any combination thereof. In some embodiments, the term "polycyclyl" encompasses a polycyclic aromatic ring, a polycyclic aliphatic ring, or a mixed polycyclic ring.

In some embodiments, the term "mixed polycyclic ring" refers to any plurality of rings covalently bound to each other (e.g. fused rings, dicylyls, spirocyclic rings etc.) comprising at least one aromatic ring (aryl, or heteroaryl) and at least one aliphatic or non-aromatic ring (optionally a heterocyclyl and/or unsaturated cyclyl).

In some embodiments, the term "cyclyl" comprises C3-C10 cyclyl. In some embodiments, the term "C3-C10 cyclyl" and the term "(C3-C10) ring" are used herein interchangeably and are referred to an optionally substituted C3, C4, C5, C6, C7, C8, C9 or C10 aliphatic ring, aromatic ring, or a ring comprising an unsaturated bond.

As used herein the term "substituted" encompasses substitution by one or more R, wherein R comprises any one of —$NO_2$, —CN, —OH, —$CONH_2$, —$CONR'_2$, —$CNNR'_2$, —$CSNR'_2$, —CONH—OH, —CONH—$NH_2$, —NHCOR', —NHCSR', —NHCNR', —NC(═O)R', —NC(═O)OR', —NC(═O)NR', —NC(═S)OR', —NC(═S)NR', —$SO_2R'$, —SOR', —SR', —$SO_2OR'$, —$SO_2N(R')_2$, —$NHNR'_2$, —NNR', carbonyl, $C_1$-$C_{10}$ haloalkyl, optionally substituted $C_1$-$C_{10}$ alkyl, —$NH_2$, —NH($C_1$-$C_{10}$ alkyl), —N($C_1$-$C_{10}$ alkyl)$_2$, $C_1$-$C_{10}$ haloalkoxy, hydroxy($C_1$-$C_{10}$ alkyl), hydroxy ($C_1$-$C_{10}$ alkoxy), alkoxy($C_1$-$C_{10}$ alkyl), alkoxy($C_1$-$C_{10}$ alkoxy), amino($C_1$-$C_{10}$ alkyl), —CONH($C_1$-$C_{10}$ alkyl), —CON($C_1$-$C_{10}$ alkyl)$_2$, —$CO_2$ H, —$CO_2R'$, —OCOR', —C(═O)R', —OC(═O)OR', —OC(═O)NR', —OC(═S) OR', —OC(═S)NR', a heteroatom, cycloalkyl, heterocyclyl, aryl, heteroaryl, ($C_1$-$C_{10}$ alkyl)alkyl-cycloalkyl, ($C_1$-$C_{10}$ alkyl)alkyl-aryl, ($C_1$-$C_{10}$ alkyl)alkyl-heteroaryl, or any combination thereof, and wherein each of cycloalkyl, heterocyclyl, aryl, heteroaryl is substituted or non-substituted, including any combination thereof.

In some embodiments, A comprises any one of:

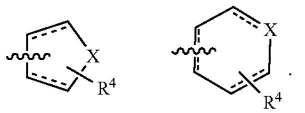

wherein X and $R^4$ are as described herein.

In some embodiments, the compound is represented by formula II:

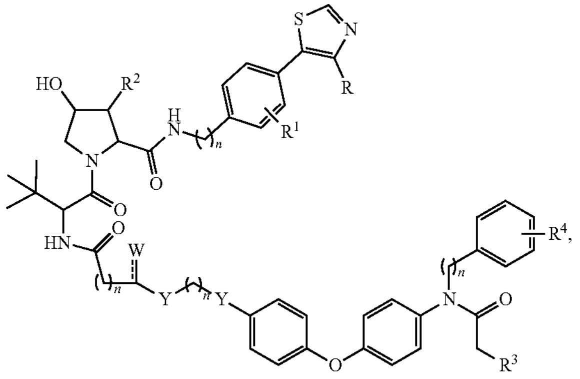

wherein n, Y, W, R, $R^1$, $R^2$, $R^3$ and $R^4$ are as described herein.

In some embodiments, the compound is represented by formula IIa:

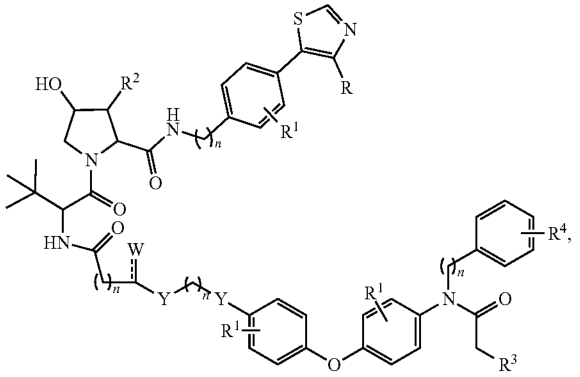

wherein n, Y, W, R, $R^1$, $R^2$, $R^3$ and $R^4$ are as described herein.

In some embodiments, the compound is represented by Formula IIb:

(IIb)

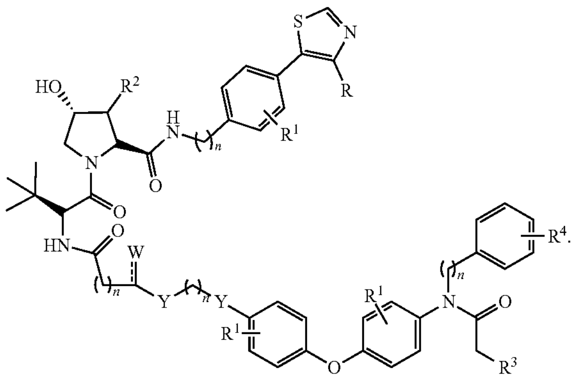

In some embodiments, the compound is represented by Formula III:

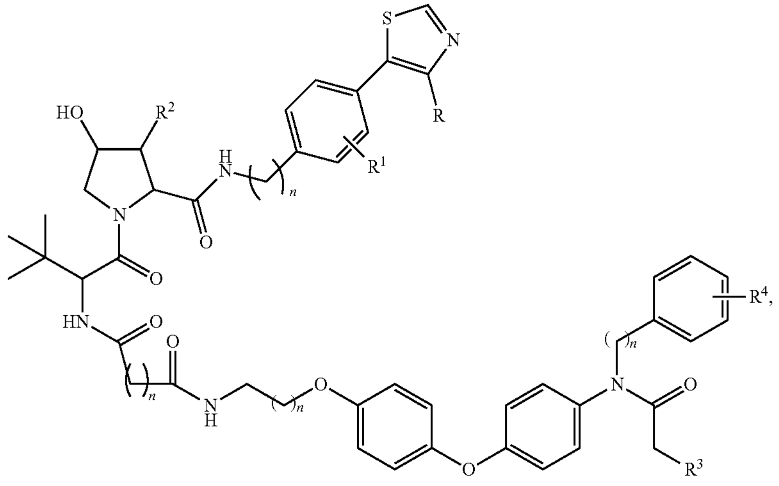

wherein n, R, $R^1$, $R^2$, $R^3$ and $R^4$ are as described herein.

In some embodiments, the compound is represented by Formula IIIa:
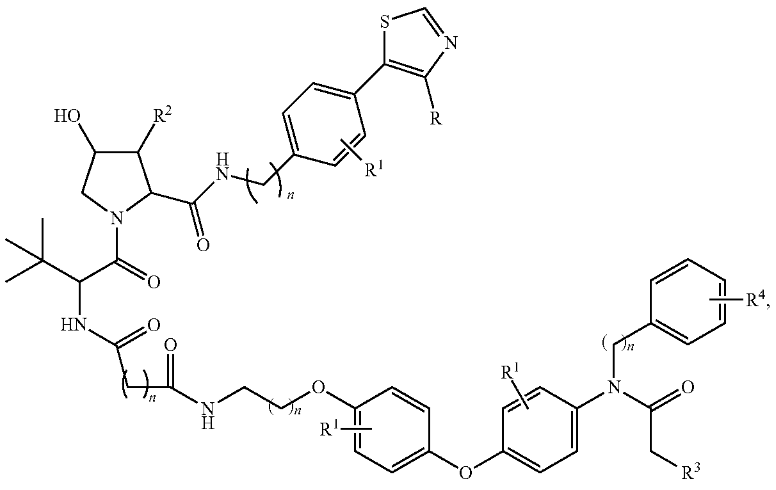
wherein n, R, $R^1$, $R^2$, $R^3$ and $R^4$ are as described herein.
In some embodiments, the compound is represented by Formula IIIb:
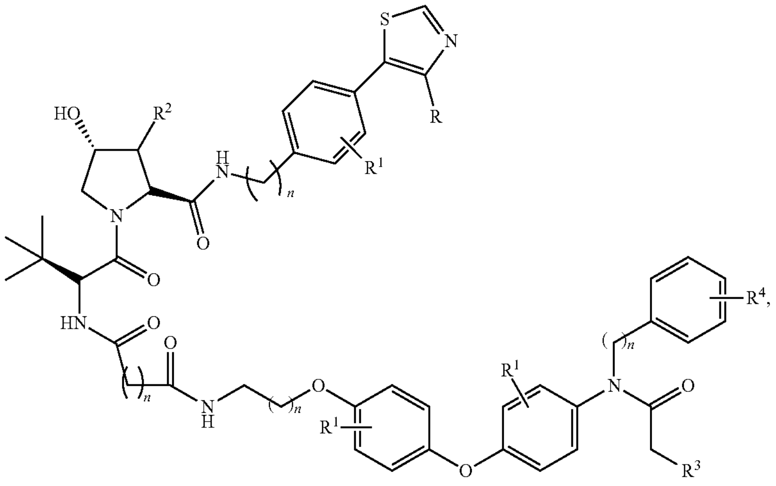
wherein n, R, $R^1$, $R^2$, $R^3$ and $R^4$ are as described herein.

In some embodiments, the compound is represented by Formula IV:
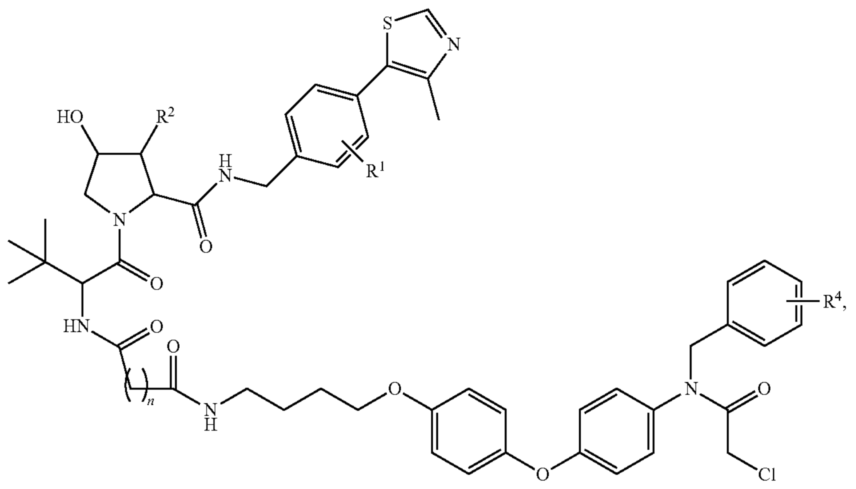
wherein n, $R^1$, $R^2$, and $R^4$ are as described herein.
In some embodiments, the compound is represented by Formula IVa:
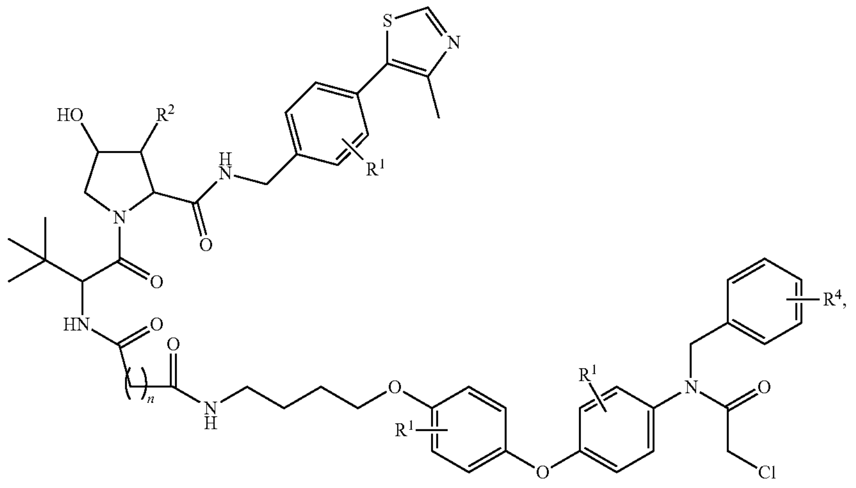
wherein n, $R^1$, $R^2$, and $R^4$ are as described herein.

In some embodiments, the compound is represented by Formula IVb:

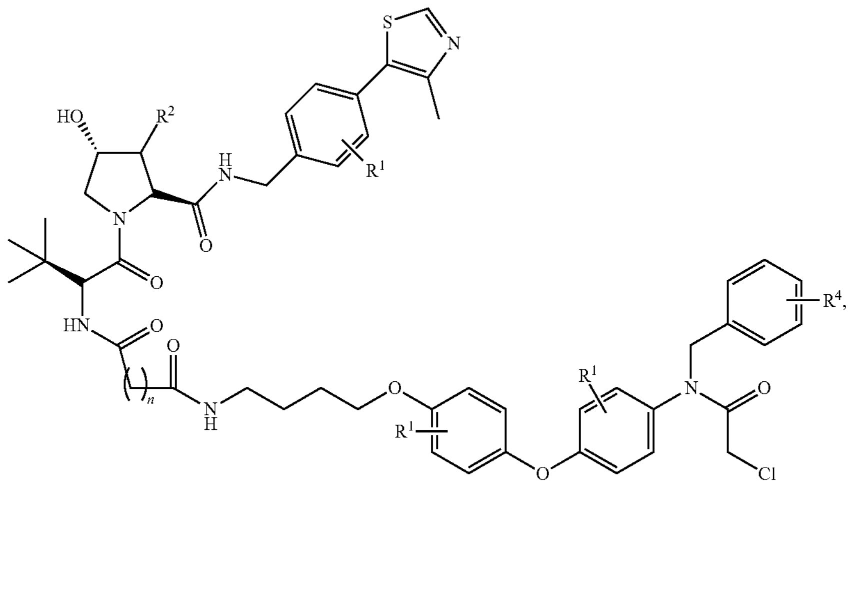

wherein n, $R^1$, $R^2$, and $R^4$ are as described herein.

In some embodiments, each of the n independently represents an integer in a range from 1 to 5.

In some embodiments, the $R^1$ is selected from the group consisting of: a methyl group, an isopropyl group, a tent-butyl group, a ($C_2$-$C_{10}$) alkyl group, a substituted ($C_2$-$C_{10}$) alkyl group, a cycloalkyl group, a phenoxy group, a methoxy group, a carboxy group, a nitro group, and a trihalomethyl group.

In some embodiments, the $R^2$ is a halo group.

In some embodiments, the $R^4$ is selected from the group consisting of: a methyl group, an isopropyl group, a tent-butyl group, a ($C_2$-$C_{10}$) alkyl group, a substituted ($C_2$-$C_{10}$) alkyl group, a phenoxy group, a methoxy group, a halo group, a haloalkyl group, a nitro group, and a trihalomethyl group.

In some embodiments, the compound is:

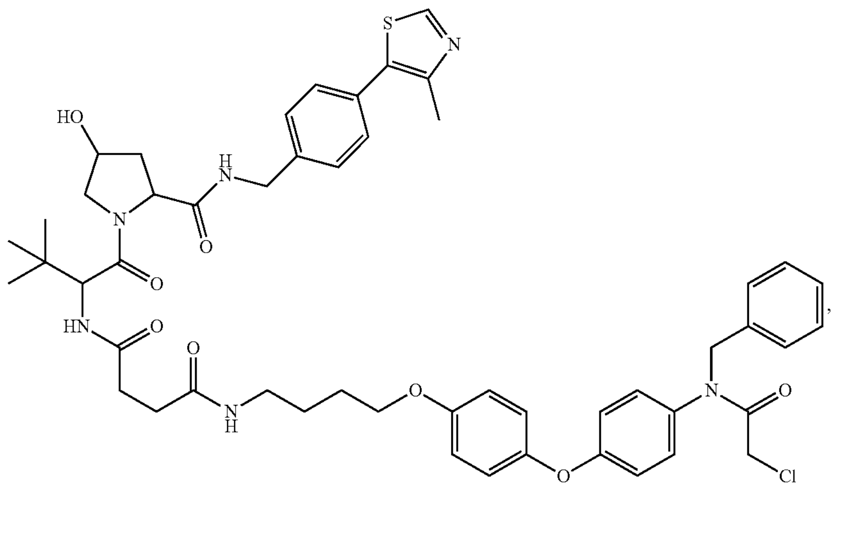 [SMILES: Cc1ncsc1-c1ccc(CNC(=O)C2CC(O)CN2C(=O)C(NC(=O)CCC(=O)NCCCCOc2ccc(Oc3ccc(N(Cc4ccccc4)C(=O)CCl)cc3)cc2)C(C)(C)C)cc1]

including any diastereomer, or any tautomer thereof.

In some embodiments, the compound is:
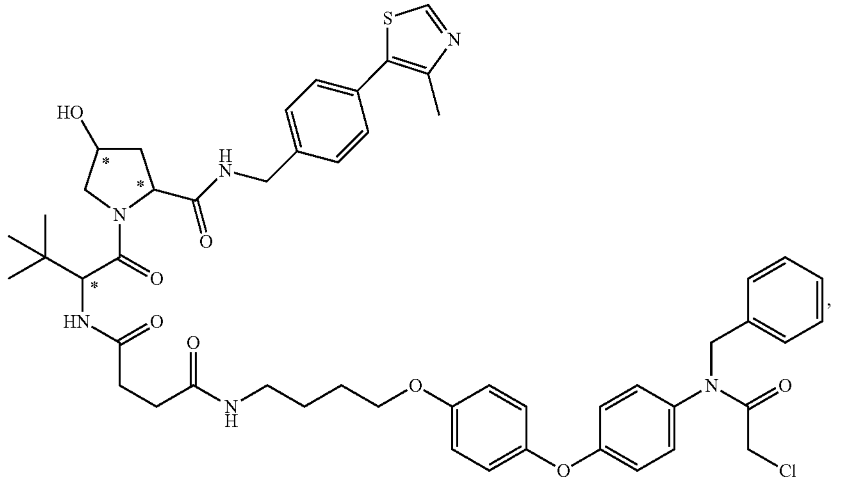 [SMILES: Cc1ncsc1-c1ccc(CNC(=O)C2CC(O)CN2C(=O)C(NC(=O)CCC(=O)NCCCCOc2ccc(Oc3ccc(N(Cc4ccccc4)C(=O)CCl)cc3)cc2)C(C)(C)C)cc1]
wherein * is referred to any of R or S enantiomers or a mixture thereof.
In some embodiments, the compound is:
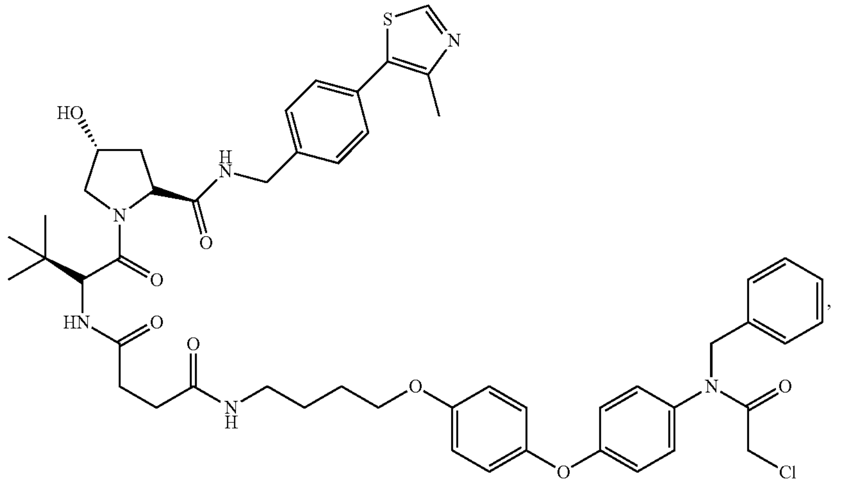
including any diastereomer, or any tautomer thereof.

In some embodiments, the compound is selected from the group consisting of:
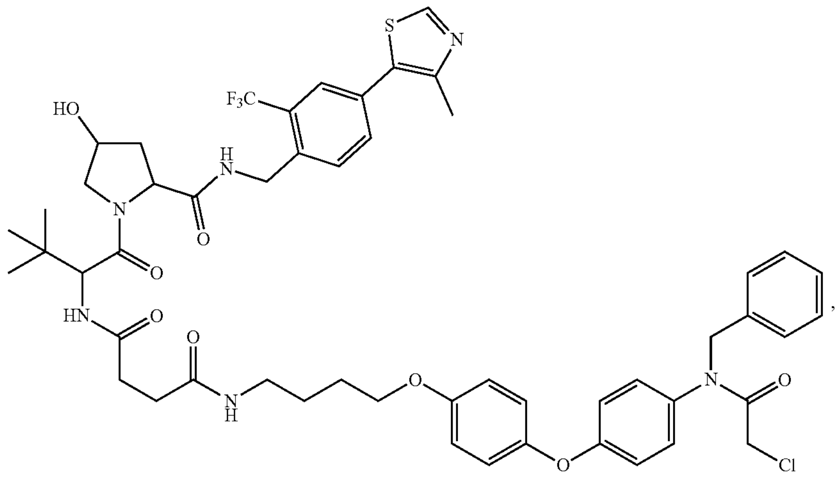 [SMILES: COc1cc(-c2scnc2C)ccc1CNC(=O)C1CC(O)CN1C(=O)C(NC(=O)CCC(=O)NCCCCOc1ccc(Oc2ccc(N(Cc3ccccc3)C(=O)CCl)cc2)cc1)C(C)(C)C]
,
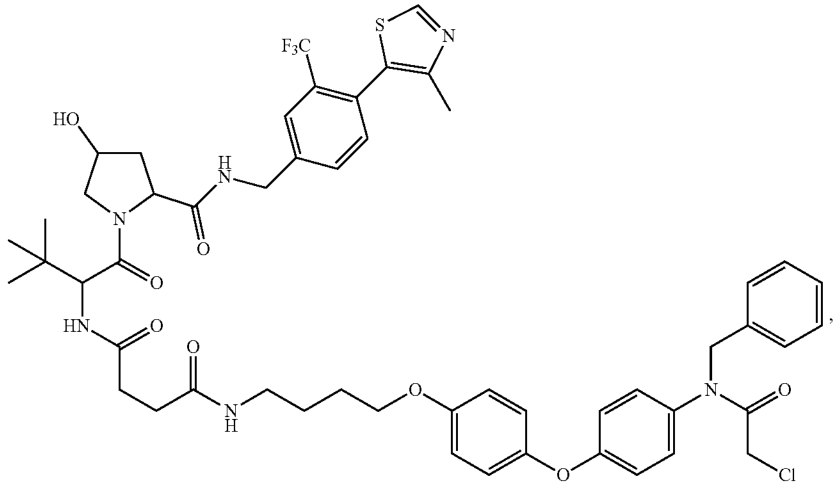
,
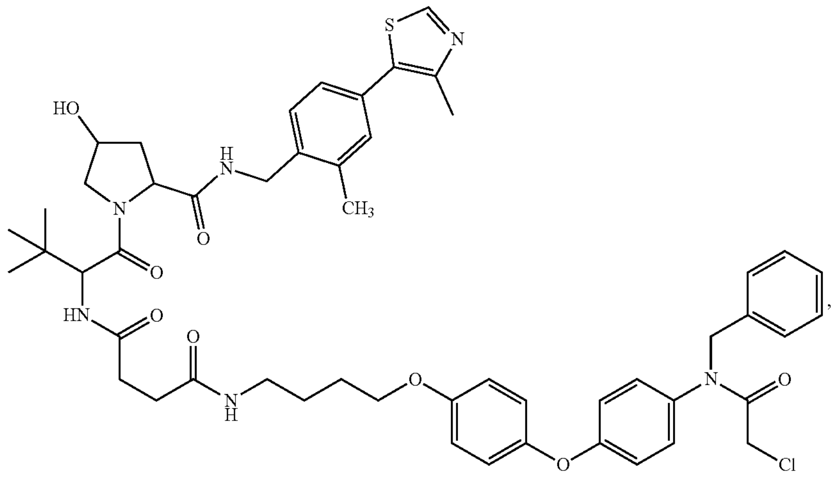
, -continued
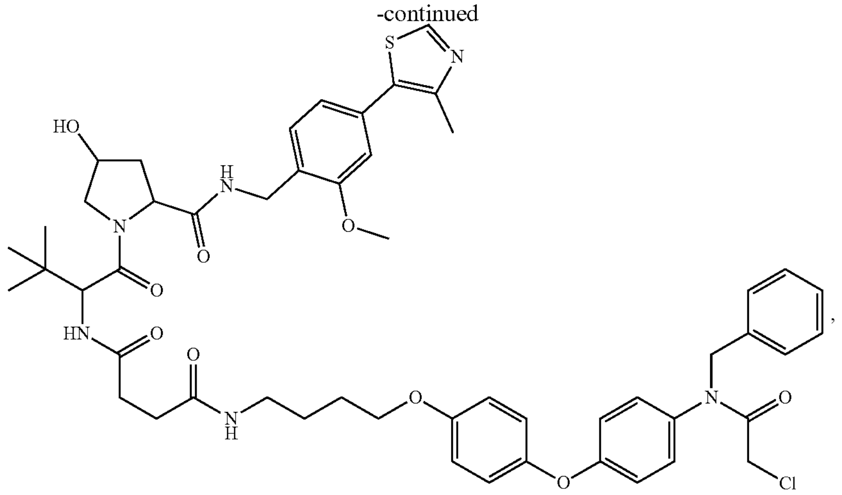
including any diastereomer, or any tautomer thereof.
In some embodiments, the compound is selected from the group consisting of:
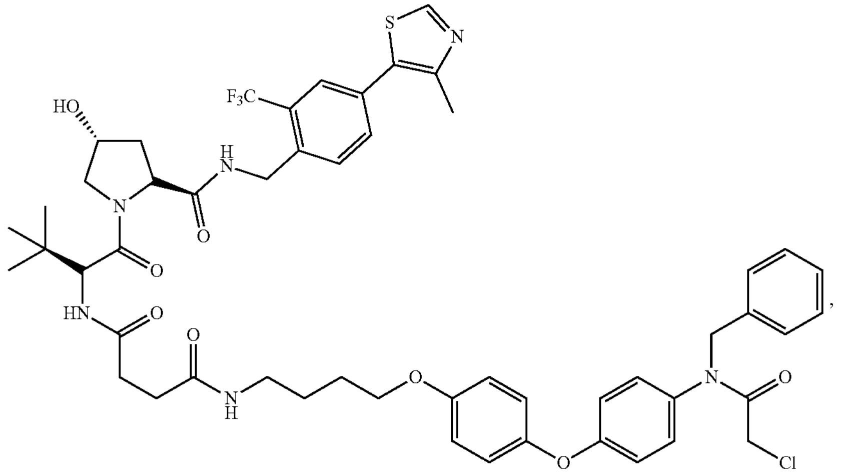
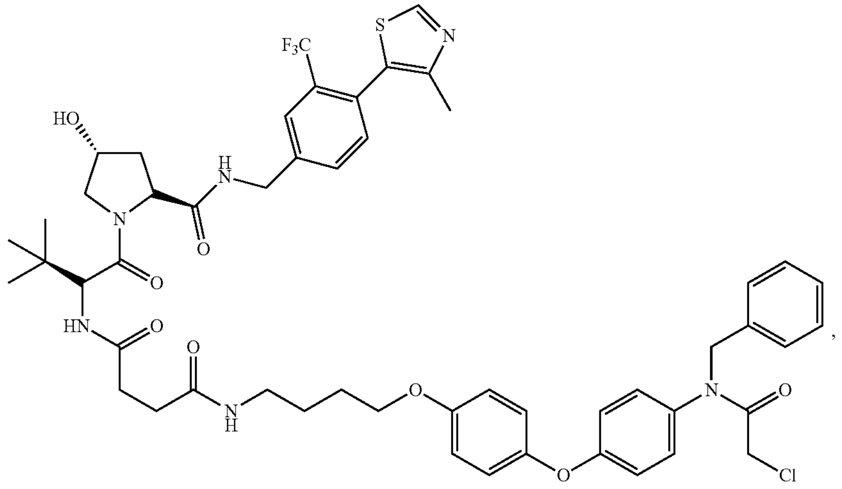

-continued

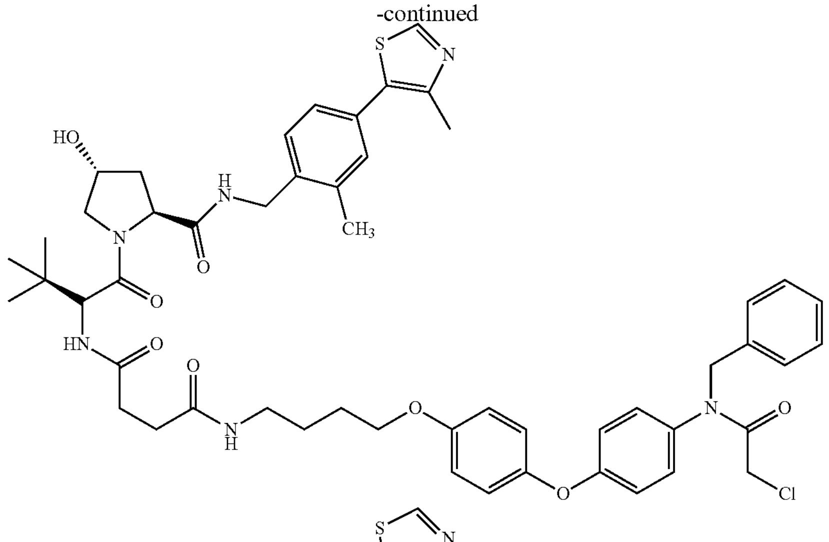

,

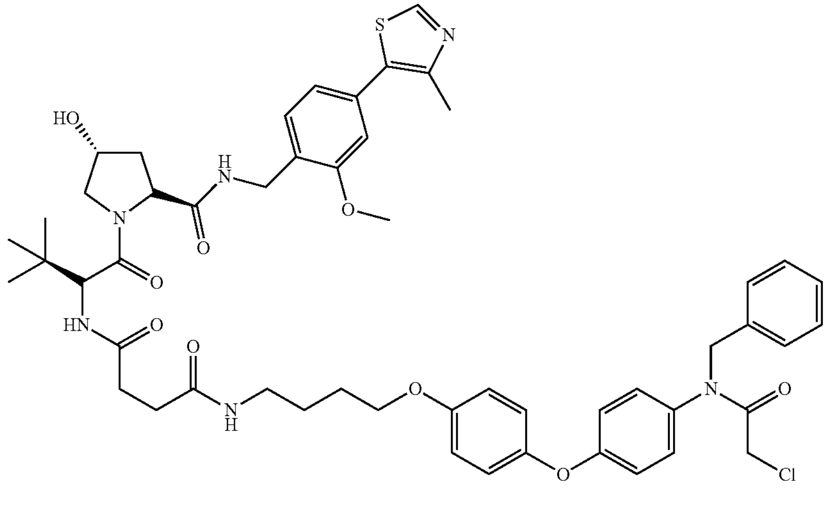

, including any diastereomer, or any tautomer thereof.

In some embodiments, the compound of the invention comprises any one of the compounds disclosed herein, including any enantiomers thereof. In some embodiments, the compound of the invention comprises a mixture of enantiomers (e.g. a racemic mixture).

The compounds described hereinabove may be applied or otherwise utilized either as is, or as an acceptable salt, enantiomer, diastereomer, solvate, or hydrate.

Non limiting examples of salts include but are not limited to: cations derived from alkali or alkaline earth metals (e.g. sodium, potassium, magnesium), cations derived from ammonia and amines (e.g. ammonium, diethylammonium, ethanolammonium, isopropylammonium) and trimethylsulfonium salts.

In some embodiments, the compounds described herein are chiral compounds (i.e. possess an asymmetric carbon atom). In some embodiments, diastereomers, geometric isomers and individual isomers are encompassed within the scope of the present invention. In some embodiments, a chiral compound described herein is in form of a racemic mixture. In some embodiments, a chiral compound is in form of a single enantiomer, with an asymmetric carbon atom having the R configuration. In some embodiments, a chiral compound is in form of a single enantiomer, with an asymmetric carbon atom having the S configuration as described hereinabove.

In some embodiments, a chiral compound is in form of a single enantiomer with enantiomeric purity of more than 70%. In some embodiments, a chiral compound is in form of a single enantiomer with enantiomeric purity of more than 80%. In some embodiments, a chiral compound is in form of a single enantiomer with enantiomeric purity of more than 90%. In some embodiments, a chiral compound is in form of a single enantiomer with enantiomeric purity of more than 95%.

In some embodiments, the compound of the invention comprising an unsaturated bond is in a form of a trans-, or cis-isomer. In some embodiments, the composition of the invention comprises a mixture of cis- and trans-isomers, as described hereinabove.

In some embodiments, the compounds described herein can exist in unsolvated form as well as in solvated form, including hydrated form. In general, the solvated form is equivalent to the unsolvated form and is encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the conjugate described herein)

and a solvent, whereby the solvent does not interfere with the biological activity of the solute. Suitable solvents include, for example, ethanol, acetic acid and the like.

The term “hydrate” refers to a solvate, as defined hereinabove, where the solvent is water.

In some embodiments, a compound as described hereinabove has increased binding affinity to RNF4. In some embodiments, a compound as described hereinabove is for use in the inhibition of RNF4. In some embodiments, the compound is capable of inhibiting stabilization of specific oncogenes. In some embodiments, the stabilized oncogenes are phosphorylated. In some embodiments, the phosphorylated oncogenes are mitogenic agents.

In some embodiments, a compound as described hereinabove is characterized by anti-tumor activity against cancer cells. In some embodiments, a compound as described hereinabove reduces proliferation and inhibition of colonies at the μM rages. In some embodiments, a compound as described hereinabove reduces proliferation and inhibition of colonies at a concentration ranging from 0.1 μM to 100 μM 0.9 μM to 100 μM 1 μM to 100 μM, 5 μM to 100 μM, 10 μM to 100 μM, 0.1 μM to 50 μM, 0.9 μM to 50 μM, 1 μM to 50 μM, 5 μM to 50 μM, 10 μM to 50 μM, 0.1 μM to 30 μM, 0.9 μM to 30 μM, 1 μM to 30 μM, 5 μM to 30 μM, or 10 μM to 30 μM, including any range therebetween. Each possibility represents a separate embodiment of the invention.

In some embodiments, a compound as described hereinabove reduces proliferation and inhibition of melanoma cells at a concentration ranging from 0.1 μM to 100 μM, 0.9 μM to 100 μM, 1 μM to 100 μM, 5 μM to 100 μM, 10 μM to 100 μM, 0.1 μM to 50 μM, 0.9 μM to 50 μM, 1 μM to 50 μM, 5 μM to 50 μM, 10 μM to 50 μM, 0.1 μM to 30 μM, 0.9 μM to 30 μM, 1 μM to 30 μM, 5 μM to 30 μM, or 10 μM to 30 μM, including any range therebetween. Each possibility represents a separate embodiment of the invention.

In some embodiments, a compound as described hereinabove inhibits the growth of human melanoma cells. In some embodiments, a compound as described hereinabove inhibits the growth of human melanoma cells resistant to therapy by the inhibitor Vemurafenib. In some embodiments, a compound as described hereinabove reduces proliferation and inhibition of Vemurafenib-resistant melanoma cells (A375R) at a concentration ranging from 0.1 μM to 100 μM, 0.9 μM to 100 μM, 1 μM to 100 μM, 5 μM to 100 μM, 10 μM to 100 μM, 0.1 μM to 50 μM, 0.9 μM to 50 μM, 1 μM to 50 μM, 5 μM to 50 μM, 10 μM to 50 μM, 0.1 μM to 30 μM, 0.9 μM to 30 μM, 1 μM to 30 μM, 5 μM to 30 μM, or 10 μM to 30 μM, including any range therebetween. Each possibility represents a separate embodiment of the invention.

As used herein, increased binding affinity is by at least 10%. In one embodiment, increased affinity as used herein is by at least 30%. In one embodiment, increased affinity as used herein is by at least 50%. In one embodiment, increased affinity as used herein is by at least 75%. In one embodiment, increased affinity as used herein is by at least 100%. In one embodiment, increased affinity as used herein is by at least 150%. In one embodiment, increased affinity as used herein is by at least 250%. In one embodiment, increased affinity as used herein is by at least 500%. In one embodiment, increased affinity as used herein is by at least 1,000%.

In one embodiment, increased affinity as used herein is by at least 1.5-fold. In one embodiment, increased affinity as used herein is by at least 2-fold. In one embodiment, increased affinity as used herein is by at least 5-fold. In one embodiment, increased affinity as used herein is by at least 10-fold. In one embodiment, increased affinity as used herein is by at least 50-fold. In one embodiment, increased affinity as used herein is by at least 100-fold. In one embodiment, increased affinity as used herein is by at least 500-fold. In one embodiment, increased affinity as used herein is by at least 1,000-fold.

In some embodiments, a compound as described herein above is characterized by targeting RNF4 for proteasomal degradation.

Pharmaceutical Compositions Comprising the Disclosed Compounds

According to an aspect of embodiments of the invention there is provided a pharmaceutical composition comprising one or more compounds as described herein and a pharmaceutically acceptable carrier.

According to an aspect of embodiments of the invention there is provided a pharmaceutical composition comprising therapeutically effective amount of one or more compounds as described herein.

According to another aspect, the invention provides a pharmaceutical composition comprising as an active ingredient, a therapeutically effective amount of a compound the present invention, and a pharmaceutically acceptable carrier and/or diluent.

In some embodiments, the pharmaceutical composition is for use in the inhibition of Ring Finger Protein 4 (RNF4).

In some embodiments, the pharmaceutical composition is for use in the prevention or treatment of a disorder associated with cancer, inflammatory disorder, autoimmune disorder, or viral infection.

In some embodiments, the cancer is selected from the group consisting of: melanoma, squamous cell carcinoma breast cancer, colorectal cancer, osteosarcoma, lung cancer, ovarian cancer, prostate cancer, pancreatic cancer and hematological cancers.

The compounds described hereinabove may be administered or otherwise utilized either as is, or as a pharmaceutically acceptable salt, an enantiomer, a tautomer, a diastereomer, a protonated or non-protonated form, a solvate, a hydrate, or a prodrug thereof.

The phrase “pharmaceutically acceptable salt” refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase “pharmaceutically acceptable salts” is meant to encompass salts of the active compounds which are prepared with relatively nontoxic acids or bases, depending on the particular substituents found on the compounds described herein.

Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compound as described herein to be converted into either base or acid addition salts.

In some embodiments, the neutral forms of the compounds described herein are regenerated by contacting the salt with a base or acid and isolating the parent compounds in a conventional manner. The parent form of the compounds differs from the various salt forms in certain physical properties, such as solubility in polar solvents, but otherwise the salts are equivalent to the parent form of the compound for the purposes of the present invention.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

In some embodiments, the compounds described herein possess asymmetric carbon atoms (optical centers) or double bonds; the racemates, diastereomers, tautomers, geometric isomers and individual isomers are encompassed within the scope of the present invention.

As used herein and in the art, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

In some embodiments, the compounds described herein can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

In some embodiments, the "pharmaceutical composition" refers to a preparation of one or more of the compounds described herein (as active ingredient), or physiologically acceptable salts or prodrugs thereof, with other chemical components including, but not limited to, physiologically suitable carriers, excipients, lubricants, buffering agents, antibacterial agents, bulking agents (e.g., mannitol), antioxidants (e.g., ascorbic acid or sodium bisulfate), anti-inflammatory agents, anti-viral agents, chemotherapeutic agents, anti-histamines and other.

In some embodiments, the purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier", which may be interchangeably used, refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, PA, latest edition, which is incorporated herein by reference.

In some embodiments, pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage, as described and specified herein, may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p.1).

In some embodiments, the pharmaceutical composition may be formulated for administration in either one or more of routes depending on whether local or systemic treatment or administration is of choice, and on the area to be treated. As further described herein throughout, administration may be done orally, dentally, by inhalation, or parenterally, for example by intravenous drip or intraperitoneal, subcutaneous, intramuscular or intravenous injection, or topically (including ophtalmically, vaginally, rectally, intranasally).

Formulations for topical and/or dental administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration may include powders or granules, suspensions, dental compositions, or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an antibacterial agent, an antioxidant, a buffering agent, a bulking agent, a surfactant, an anti-inflammatory agent, an anti-viral agent, a chemotherapeutic agent and anti-histamine.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be recognized that these embodiments are susceptible to various modifications and alternative forms well known to those of skill in the art.

As used herein, the term "pharmaceutically acceptable" means suitable for administration to a subject, e.g., a human and/or for a proliferating cell as described herein. For example, the term "pharmaceutically acceptable" can mean approved by a regulatory agency of the Federal or a state government or listed in the U. S. Pharmacopeia or other generally recognized pharmacopeia for use in animals, and more particularly in humans. In some embodiments, pharmaceutically acceptable carrier is non-toxic, inert solid, semi-solid liquid filler, diluent, encapsulating material, formulation auxiliary of any type, or simply a sterile aqueous medium, such as saline. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents that may be useful in the present compositions include di stilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety.

According to an embodiment of the invention, pharmaceutical compositions contain 0.1%-95% of the compound of the present invention. According to another embodiment of the invention, pharmaceutical compositions contain 1-70% of the compound. According to another embodiment of the invention, the pharmaceutical composition or formulation to be administered may contain a quantity of the compound, according to embodiments of the invention in an amount effective to treat the condition or disease of the subject being treated.

According to one embodiment, the pharmaceutical compositions of the present invention are administered in the form of a pharmaceutical composition comprising at least one of the active components of this invention (a compound as described hereinabove) together with a pharmaceutically acceptable carrier or diluent. In another embodiment, the compositions of this invention can be administered either individually or together in any conventional sub-retinal or transdermal dosage form.

The carrier may comprise, in total, from about 0.1% to about 99.99999% by weight of the pharmaceutical compositions presented herein.

The pharmaceutical compositions also include incorporation of the active material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

As used herein, the terms "administering," "administration," and like terms refer to any method which, in sound medical practice, delivers a composition containing an active agent to a subject in such a manner as to provide a therapeutic effect.

In one embodiment, depending on the severity and responsiveness of the condition to be treated, dosing can be of a single or a plurality of administrations, with course of treatment lasting from several days to several weeks or until cure is affected or diminution of the disease state is achieved.

As used herein, the term "therapeutically active molecule" or "therapeutic agent" means a molecule, group of molecules, complex or substance administered to an organism for diagnostic, therapeutic, preventative medical, or veterinary purposes. This term includes pharmaceuticals, e.g., small molecules, treatments, remedies, biologics, devices, and diagnostics, including preparations useful in clinical screening, prevention, prophylaxis, healing, imaging, therapy, surgery, monitoring, and the like. This term can also specifically include nucleic acids and compounds comprising nucleic acids that produce a bioactive effect, for example.

The term "therapeutically effective amount" refers to the concentration of the compound(s), or their combination, normalized to body weight, that is effective to treat a disease or disorder in a mammal. The term "a therapeutically effective amount" refers to an amount effective, at dosages and for periods of time necessary, to achieve the desired therapeutic or prophylactic result. A physician or veterinarian of ordinary skill can readily determine and prescribe the effective amount of the bioactive agent required.

In some embodiments, a pharmaceutical composition of the invention comprises pharmaceutically active agents. In some embodiments, pharmaceutically active agents are added prior to transplantation. Pharmaceutically active agents include but are not limited to any of the specific examples disclosed herein. Those of ordinary skill in the art will recognize also numerous other compounds that fall within this category and are useful according to the invention.

Methods of Use

According to some aspects, there is provided a method for treating, ameliorating, reducing and/or preventing a RNF4 related disorder.

According to some aspects, there is provided a method for treating, ameliorating, reducing and/or preventing a condition associated with increased cell proliferation in a subject in need thereof, the method comprising the step of: administering to a subject a pharmaceutical composition comprising an effective amount of a compound of the invention, thereby treating, ameliorating, reducing and/or preventing a condition associated with increased cell proliferation in a subject in need thereof.

According to some embodiments, there is provided a method for treating, ameliorating, reducing and/or preventing cancer or pre-malignancy condition in a subject in need thereof, the method comprising the step of: administering to a subject a pharmaceutical composition comprising an effective amount of a compound of the invention, thereby treating, ameliorating, reducing and/or preventing cancer or pre-malignancy condition in a subject in need thereof.

In some embodiments, there is provided a method for treating cancer or pre-malignancy condition in a subject in need thereof, the method comprising the step of administering to the subject a pharmaceutical composition comprising an effective amount of a compound of the invention and pharmaceutical acceptable carrier, thereby treating, ameliorating, reducing and/or preventing cancer or pre-malignancy condition in a subject in need thereof. In some embodiments, the subject is further treated with an additional anticancer therapy such as chemotherapy, radiotherapy, immunotherapy, hormonal therapy, toxin therapy or surgery.

In another embodiment, a compound of the invention or a composition comprising the compound is for use in treatment, amelioration, reduction, and/or prevention of a RNF4 related disorder.

In another embodiment, a compound of the invention or a composition comprising the compound is for use in treatment, amelioration, reduction, and/or prevention of cancer or pre-malignancy condition in a subject in need thereof. In some embodiments, there is provided a composition comprising an effective amount of the compound for use in the treatment or prevention of cancer or pre-malignancy condition in a subject in need thereof. In some embodiments, there is provided a composition comprising an effective amount of one or more compounds disclosed herein, for use in the treatment or prevention of cancer or pre-malignancy condition in a subject in need thereof In some embodiments, the composition further comprises at least one anticancer agent such as a chemotherapeutic agent. In some embodiments, the composition is adopted for use in combination with an anticancer therapy such as chemotherapy, radiotherapy, immunotherapy, hormonal therapy, toxin therapy or surgery.

In some embodiments, there is provided a use of a composition comprising an effective amount of a compound of the invention in the preparation of a medicament for the treatment, amelioration, reduction, or prevention of a disease associated with increased cell proliferation in a subject in need thereof. In some embodiments, the invention provides use of a composition comprising an effective amount of a compound disclosed herein in the preparation of a medicament for the treatment of a disease associated with increased cell proliferation in a subject in need thereof.

In one embodiment, the compound of the present invention is provided to the subject per se. In one embodiment, one or more of the compound of the present invention are provided to the subject per se. In one embodiment, the compound of the present invention is provided to the subject as part of a pharmaceutical composition where it is mixed with a pharmaceutically acceptable carrier. In one embodiment, one or more of the compound of the present invention are provided to the subject as part of a pharmaceutical composition where they are mixed with a pharmaceutically acceptable carrier.

In some embodiments, the RNF4 related disorder is cancer. In some embodiments, the RNF4 related disorder is autoimmune disorder. In some embodiments, the RNF4 related disorder is inflammatory disorder. In some embodiments, the RNF4 related disorder is viral infection.

As used herein, the term "inflammatory disorder" refers to a disorder relating to abnormality of inflammation. It refers to any deviation from baseline functioning of organismal physiology caused by, or related to, inflammation or inflammatory processes. "Inflammation" is a fundamental pathological process comprising a dynamic complex of cytological and chemical reactions that occur in the affected blood vessels and adjacent tissues in response to injury or abnormal stimulation. Inflammation may arise in response to stimulation or damage from any physical, chemical, or biological agent. The physical, chemical, or biological agent(s) may be endogenous or exogenous factors. An example of an exogenous factor includes, but is not limited to; physical trauma such as compression from a blow or strike, or biological factors such as infection. Examples of endogenous factors include, chemical imbalances such as those arising from disease, and biological factors, such as the biological responses that lead to repair and healing of injury. Inflammation may be acute or chronic. Typically, chronic inflammation involves the interaction of antigens, antibodies, and autoantigens. Inflammatory disorders that can be treated according to the invention include but are not limited to atherosclerosis, atherothrombosis, insulin resistance, pancreatitis, restenosis, an inflammatory lung disease, and an inflammatory bowel disease. It shall be understood that in the present invention, inflammatory disorders that can be treated according to the invention can be included in embodiments individually or in any combination.

The terms "autoimmune disease" or "autoimmune disorder" refer to diseases that result from an aberrant immune response of an organism against its own cells and tissues due to a failure of the organism to recognize its own constituent parts (down to the sub-molecular level) as "self". The group of diseases can be divided in two categories, organ-specific and systemic diseases.

In some embodiments, the disease associated with increased cell proliferation is cancer. In some embodiments, the cancer is selected from the group consisting of: melanoma, squamous cell carcinoma breast cancer, colorectal cancer, osteosarcoma, lung cancer, ovarian cancer, prostate cancer, pancreatic cancer and hematological cancers.

As used herein "cancer" or "pre-malignancy" are diseases associated with cell proliferation. Non-limiting types of cancer include carcinoma, sarcoma, lymphoma, leukemia, blastoma and germ cells tumors. In one embodiment, carcinoma refers to tumors derived from epithelial cells including but not limited to breast cancer, prostate cancer, lung cancer, pancreas cancer, and colon cancer. In one embodiment, sarcoma refers of tumors derived from mesenchymal cells including but not limited to sarcoma botryoides, chondrosarcoma, Ewing's sarcoma, malignant hemangioendothelioma, malignant schwannoma, osteosarcoma and soft tissue sarcomas. In one embodiment, lymphoma refers to tumors derived from hematopoietic cells that leave the bone marrow and tend to mature in the lymph nodes including but not limited to Hodgkin lymphoma, non-Hodgkin lymphoma, multiple myeloma and immunoproliferative diseases. In one embodiment, leukemia refers to tumors derived from hematopoietic cells that leave the bone marrow and tend to mature in the blood including but not limited to acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. In one embodiment, blastoma refers to tumors derived from immature precursor cells or embryonic tissue including but not limited to hepatoblastoma, medulloblastoma, nephroblastoma, neuroblastoma, pancreatoblastoma, pleuropulmonary blastoma, retinoblastoma and glioblastoma-multiforme. In one embodiment, germ cell tumors refer to tumors derived from germ cells including but not limited to germinomatous or seminomatous germ cell tumors (GGCT, SGCT) and nongerminomatous or nonseminomatous germ cell tumors (NGGCT, NSGCT). In one embodiment, germinomatous or seminomatous tumors include but not limited to germinoma, dysgerminoma and seminoma. In one embodiment, non-germinomatous or non-seminomatous tumors refers to pure and mixed germ cells tumors including but not limited to embryonal carcinoma, endodermal sinus tumor, choriocarcinoma, tearoom, polyembryoma, gonadoblastoma and teratocarcinoma.

In some embodiments, the present invention is directed to methods of prevention or treatment of a neural cancer disease. Non-limiting types of neural cancer include acoustic neuroma, astrocytoma, chordoma, CNS lymphoma, craniopharyngioma, glioma, medulloblastoma, meningioma, metastatic brain tumor, primary brain lymphoma, spinal cord tumor, oligodendroglioma, pituitary tumor, primitive neuroectodermal tumor, Schwannoma, juvenile pilocytic astrocytoma, pineal tumor and rhabdoid tumor. In one embodiment, astrocytoma refers to tumor derived from astrocytes including but not limited to grade I—pilocytic astrocytoma, grade II—low-grade astrocytoma, grade III—anaplastic astrocytoma and grade IV—glioblastoma. In one embodiment, other types of glioma include but not limited to brain stem glioma, ependymoma, mixed glioma, optic nerve glioma and subependymoma.

As used herein, "cancer or pre-malignant cell proliferation" is a molecular process which requires the involvement of the RING finger protein 4 (RNF4). In some embodiments, cancer cell transition from benign to malignant is RNF4-dependent. In another embodiment, RNF4 is an indicator of malignancy of tissues selected from, but not limited to, breast epithelium, skin cells, colorectal tissue, bone, and muscle tissue. In another embodiment, RNF4 is a biomarker correlating with poor patient prognosis.

In some embodiments, as known to one skilled in the art, malignancy-associated RNF4 is detected by an assay, including immune-assays, western-blot, immune-histochemistry, mRNA level, and the like.

The term "subject" as used herein refers to an animal, more particularly to non-human mammals and human organism. Non-human animal subjects may also include prenatal forms of animals, such as, e.g., embryos or fetuses. Non-limiting examples of non-human animals include: horse, cow, camel, goat, sheep, dog, cat, non-human primate, mouse, rat, rabbit, hamster, guinea pig, and pig. In one embodiment, the subject is a human. Human subjects may also include fetuses. In one embodiment, a subject in need thereof is a subject afflicted with and/or at risk of being afflicted with a condition associated with increased cell proliferation.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described peptides prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, the term "condition" includes anatomic and physiological deviations from the normal that constitute an impairment of the normal state of the living animal or one of its parts, that interrupts or modifies the performance of the bodily functions.

Definitions

As used herein, the term "alkyl" describes an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atoms, 22 carbon atoms, 23 carbon atoms, etc., up to and including 100 carbon atoms. In the context of the present invention, a "long alkyl" is an alkyl having at least 20 carbon atoms in its main chain (the longest path of continuous covalently attached atoms). A short alkyl therefore has 20 or less main-chain carbons. The alkyl can be substituted or unsubstituted, as defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine.

The term "haloalkyl" describes an alkyl group as defined herein, further substituted by one or more halide(s).

The term "haloalkoxy" describes an alkoxy group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The term "carboxy" or "carboxylate" describes a —C(═O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(═O)—R' group, where R' is as defined hereinabove.

The above-terms also encompass thio-derivatives thereof (thiocarboxy and thiocarbonyl).

The term "thiocarbonyl" describes a —C(═S)—R' group, where R' is as defined hereinabove.

A "thiocarboxy" group describes a —C(═S)—OR' group, where R' is as defined herein.

A "sulfinyl" group describes an —S(═O)—R' group, where R' is as defined herein.

A "sulfonyl" or "sulfonate" group describes an —S(═O)$_2$—R' group, where Rx is as defined herein.

A "carbamyl" or "carbamate" group describes an —OC(═O)—NR'R" group, where R' is as defined herein and R" is as defined for R'.

A "nitro" group refers to a —$NO_2$ group.

A "cyano" or "nitrile" group refers to a —C≡N group.

As used herein, the term "azide" refers to a —$N_3$ group.

The term "sulfonamide" refers to a —S(═O)$_2$—NR'R" group, with R' and R" as defined herein.

The term "phosphonyl" or "phosphonate" describes an —O—P(═O)(OR')$_2$ group, with R' as defined hereinabove.

The term "phosphinyl" describes a —PR'R" group, with R' and R" as defined hereinabove.

The term "alkaryl" describes an alkyl, as defined herein, which substituted by an aryl, as described herein. An exemplary alkaryl is benzyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

General

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Synthesis

The compounds a and b were synthesized as described previously. The synthetic procedure for the preparation of compound c is as follows:

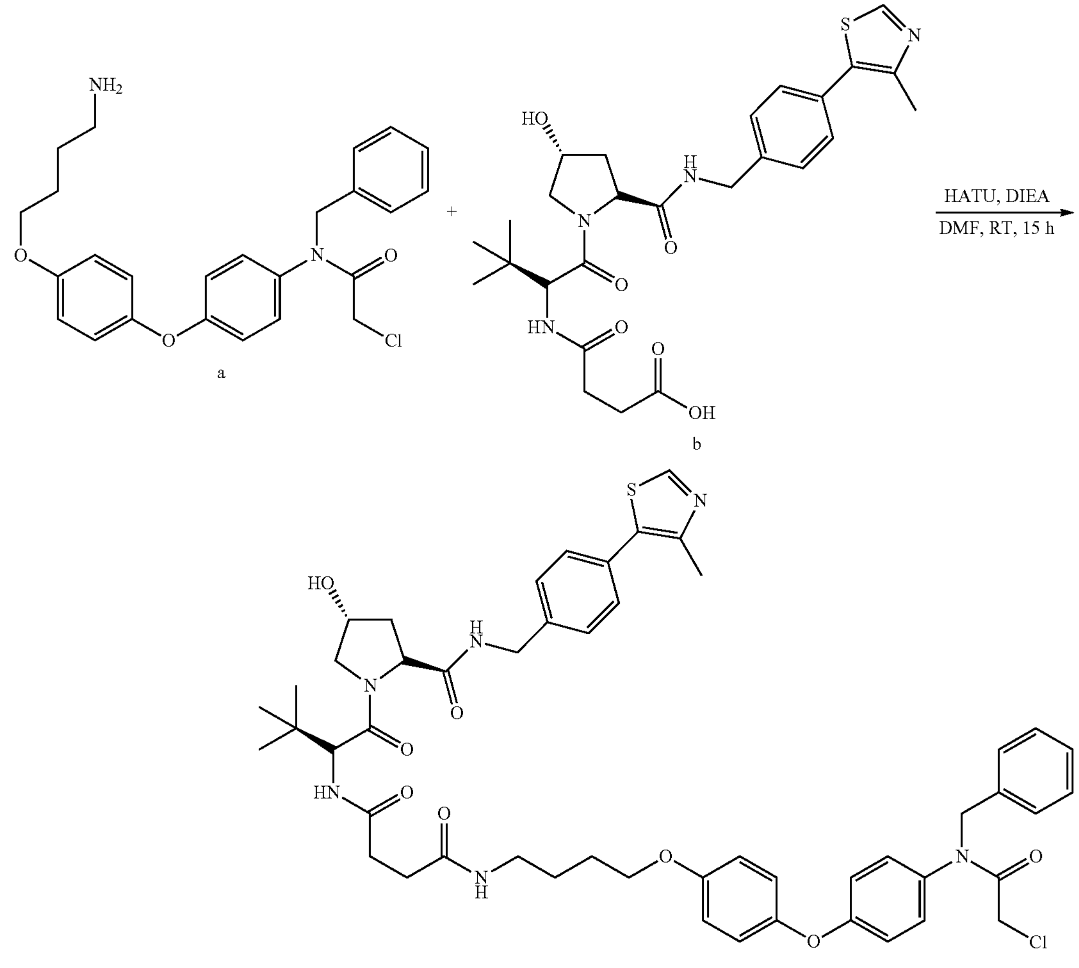

a b c

To a solution of 4-(((R)-1-((2R,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid (a, 100 mg, 0.227 mmol) in DMF (3.0 mL), N-(4-(4-(4-aminobutoxy)phenoxy)phenyl)-N-benzyl-2-chloroacetamide (b, 120.9 mg, 0.227 mmol) and DIEA (160 μL, 0.908 mmol) were added and stirred the reaction for 5 min. After 5 min, HATU (95 mg, 0.250 mmol) was added and continued the reaction for overnight at room temperature and was monitored by TLC. The reaction mixture was diluted with cold water and ethyl acetate. The organic layer was separated, dried over $Na_2SO_4$ and distilled under reduced pressure. The crude was passed through a silica loaded column chromatography to obtain the pure product N1-(4-(4-(4-(N-benzyl-2-chloroacetamido)phenoxy)phenoxy)butyl)-N4-((R)-1-((2R,4R)-4-hydroxy-2-((4-(4-methylthiazol-5-yl)benzyl)carbamoyl)pyrrolidin-1-yl)-3,3-dimethyl-1-oxobutan-2-yl)succinamide (c) in 36% isolated yield (78.1 mg). $^1H$ NMR (400 MHz, $CDCl_3$): δ 9.00 (s, 1H), 7.39 (t, J=6.0 Hz, 1H), 7.29 (q, J=13.2 Hz, 4H), 7.20-7.18 (m, 4H), 7.13-7.10 (m, 2H), 6.90-6.88 (m, 2H), 6.84-6.76 (m, 6H), 6.24 (t, J=4.8 Hz, 1H), 4.92 (s, 1H), 4.78 (s, 2H), 4.62 (t, J=8.0 Hz, 1H), 4.48-4.44 (m, 2H), 4.39-4.37 (m, 1H), 4.30-4.25 (m, 1H), 3.98 (d, J=11.6 Hz, 1H), 3.87 (t, J=6.0 Hz, 2H), 3.80 (s, 2H), 3.57-3.53 (m, 1H), 3.22-3.19 (m, 2H), 2.47-2.30 (m, 8H), 2.14-2.08 (m, 1H), 1.73-1.69 (m, 2H), 1.62-1.58 (m, 2H), 0.89 (s, 9H). $^{13}C$ NMR (100 MHz, $CDCl_3$): δ 172.3, 171.7, 170.8, 170.2, 170.1, 165.7, 159.4, 159.0, 157.9, 154.7, 151.1, 148.0, 144.6, 138.1, 135.4, 133.6, 132.5, 128.5, 128.4, 128.0, 128.0, 127.5, 127.2, 126.7, 120.5, 116.8, 114.6, 69.2, 66.8, 57.8, 57.4, 55.8, 52.9, 42.1, 40.9, 38.5, 35.4, 33.9, 30.2, 30.1, 28.7, 25.5, 25.3, 25.1, 13.5. HRMS (+ESI): calcd. for $C_{51}H_{60}ClN_6O_8S$=951.3882; found 951.3876.

Cell Lines

MDA-MB23Dox$^{SAE2shRNA}$ cells were a kind gift of Thomas F. Westbrook (Baylor College of Medicine). All cells were grown at 37° C. in 10% FCS and DMEM. HTC116Fbw7$^{+/+}$ and HTC116Fbw7$^{-/-}$ cells were a generous gift of Bert Vogelstein and Kenneth Kinzler (Johns Hopkins University). The latter were propagated in McCoy's 5A medium (Gibco) supplemented with 10% FBS and maintained in a humidified chamber at 37° C. with 5% CO2. Transient transfections were carried out using JetPei according to the manufacturer's (PolyPlus Transfections) instructions. Mouse MK4, CHO-IRES-GFP and CHO-Delta-IRES-GFP cells were grown at 37° C. and transfected with Lipofectamine 2000®.

Human melanoma cells A375 (ATCC- CRL1619) Myeloma U266 cells, and U2OS osteosarcoma cells were from ATCC and maintained in DMEM RPMI media supplemented with 100 U/ml penicillin, 0.1 mg/ml streptomycin, and 10% FBS or. Human MeWo cell lines were maintained in RPMI supplemented with 15% FBS. Resistant cells were as described previously (12): A375R and Lu1205R were cultured in DMEM with 10% FCS, penicillin/streptomycin, and 2 μM PLX4032. Cells were transfected using CalFectin transfection reagent (Sinagen Laboratories) according to manufacturer instructions. BRAF inhibitor PLX4032 was purchased from Selleckchem.

Antibodies

αRNF4 8D10 mAb antibody and rabbit polyclonal αRNF4 were used as described (Thomas et al. 2016). α-VEGF was a kind gift from Israel Vlodaysky. Anti-Ubiquitin antibody [Ubi-1 1:100] (ab7254) was from Abcam. rabbit α-HIF-1α (1:500, #10006421) was from Cayman Chemicals, and mouse α-Actin (1:1000) was from MP Biomedicals. Mouse α-tubulin (1:2000, #SC5286), mouse α-c-Myc mAb 9E10 (1:500, #SC40), and α-HA1.1 mAb (1:1000, #SC-393579) were from Santa Cruz Biotechnologies. Rat α-mCD31 (1:200, #DIA310) was from Dianova, α-FLAG M2 mAb (1:500, #F3165) was from Sigma.

shRNA Design, Production and Targeting

Generation of constitutive pLKO-based shRNF4 (C1, C2), and scrambled (sc; control), as well as Dox-induced conditional miR-30-based RNF4 knockdown (ShRNF4-1, ShRNF4-2, and Renilla control) are described in (5). RNA extraction, cDNA synthesis and qPCR analysis: qPCR analysis was performed as described in (Heüberger et al. 2014).

Protein Stability Assays

Protein stability using Cyclohexamide chase experiments was determined as described (Abed, et al. 2011; Trausch-Azar et al. 2014). When indicated, constitutive shRNA was induced with 1 μg/ml doxycycline for 36 h before cell harvesting. Cells were lysed in RIPA buffer and lysates were resolved over SDS-PAGE. Proteins were identified using indicated antibodies and visualized using chemiluminescence (Image-Quant LAS4000). $^{35}S$-Met pulse/chase experiments were performed as described in (Abed et al 2011). Pulse labeling, was 10 min for c-Myc and 30 min for NICD at 37° C. IP of c-Myc and FLAG-NICD proteins was performed using α-c-Myc (N262, 1:50) and α-Flag (1:200), respectively.

Protein Stability in the Presence of RNF4-VHL-PROTAC (R4VP)

Protein stability was determined in steady state and dynamic CHX chase experiments as described (Trausch-Azar et al. 2015). Proteins resolved over SDS-PAGE, using the indicated antibodies, and visualized using chemiluminescence (Image-Quan LAS4000). Where indicated cells were treated for the indicated times and concentrations with R4VP or related compounds.

Cell Viability Assay

Cell viability was assessed using MTT (Sigma-Aldrich) and ATP-lite (Perkin Elmer) assays according to the manufacture instructions. In assays evaluating resistance to PLX4032, PLX4032-treated cells were cultured for six days before analysis. Viability was measured using cells were performed in 96-well plates and cells incubated for 24 h at 37° C. Next, cells were incubated in MTT solution (Sigma-Aldrich) and processed according to the manufacturer instructions and analyzed using Stat Fax 2100 ELISA reader.

Colony formation assay: Cells were suspended in DMEM or RPMI medium and seeded at a density of 1000 cells/well. Plates were maintained at 37° C. for six days, fixed overnight with 4% paraformaldehyde (PFA), stained with 0.05% crystal violet.

Wnt, and Myc Luciferase Reporter Assays

Reporter assays were performed as previously described. Where indicated, LiCl was added for 12 h at a final concentration of 15 mM to activate the TOP-reporter. Cells were harvested 48 h post-transfection and assayed for luciferase and β-galactosidase activities.

In Vitro GST-Binding Assays

Binding assays were performed as previously described using bacterial expressed purified and immobilized GST, GST-RNF4 and GST-RNF4ΔARM proteins and where indicated, 35S-Met-c-Myc or 35S-Met-c-MycS62A or 35S-Met-β-catenin. For substrate de-phosphorylation the indicated proteins were pre-incubated with CIP or buffer only for 20'.

GST-bound material was resolved over SDS-PAGE and radioactive proteins visualized using a Typhoon 9400® imager.

Ubiquitylation in Cells

Ubiquitylation and SUMOylation were performed as previously described. 3×105 HEK293T transfected with indicated vectors. 48 h post-transfection, cells were incubated with 0.01 mM MG132 for 6 h, and subjected to hot lysis followed by immune precipitation. Where His-Ub was used, cells were or lysed in 1 ml guanidine-hydrochloride buffer followed by binding to Ni-NTA beads (Qiagen) in the presences of 20 mM imidazole. Ubiquitylated and SUMOylated proteins were visualized a SDS-PAGE gels followed by western blotting with the indicated antibodies.

Pathology

Human samples were obtained from the Institute of Pathology, RAMBAM Healthcare Haifa, Israel. Paraffin blocks immunostained with indicated antibodies and an automated BenchMark XT system. Certified GI pathologist confirmed diagnosis of each case. All experiments with human tissues were conducted under Helsinki committee approval number 0239-12-RMB. Analysis of mRNA of melanoma patient samples was performed by Tongwu Zhang, Division of Cancer Epidemiology and Genetics, Laboratory of Translational Genomics, National Cancer Institute, Bethesda, MD, 20892 USA.

Resistance to Vemurafenib in Cell Culture and In Vivo

Cells were infected with pINDUCER conditional doxycycline lentiviral vectors coding for control or RNF4 shRNA. shRNA was induced by the addition of doxycycline at a concentration of 0.5 μg/ml for 4 days in vitro and at a concentration of 2 mg/ml in drinking water for the in vivo experiment. For the in vitro experiment A375R cells infected with shRNF4 or scrambled control were plated in 96 well plate at 1000 cells/well. Cells were exposed to increasing concentrations of Vemurafenib for 6 days. Cell viability was measured using ATPLite assay. For the in vivo experiment, $1*10^6$ A375R cells were injected subcutaneously to six-week-old female nude mice. Three days after injection Dox was added to drinking water and the mice were treated with oral Vemurafenib. Briefly, Tumor growth was monitored twice per week for four weeks, at which point the mice will be sacrificed and tumors will be harvested.

Tissue Microarray (TMA)

Tissue microarray were constructed as described (Jilaveanu et al. 2009). Tumors were stained using α-RNF4 mAb8D10 antibody and assessed for RNF4 level. Clinical data regarding response to treatment, disease-free and overall survival were collected and analyzed by HK.

Correlation Between RNF4 mRNA Levels and Resistance to Therapy in Patient Samples We analyzed a melanoma cohort treated with MAPK inhibitors; Post-treatment biopsies were taken when the tumor progressed. Fifteen patient samples that were analyzed for RNF4 mRNA level; 9 responders, and 6 non-responders and set a threshold of 30% reduction in tumor size. Additionally, we analyzed 12 patient samples; 3 patients were treated with Dabtrafenib and Trametinib, 7 patients with Dabrafenib, and 2 patients with Vemurafenib (. RNF4 mRNA expression was compared between pre-treatment and post-treatment samples using paired Wilcoxon Ranksum test.

Statistical Analysis

SEM and t-test comparisons were performed using GraphPad Prism and ANOVAs software. In all experiments, significance as follows: **=p<0.0001, *=P<0.001, **=P<0.05, *=P<0.01.

Example 1

Background on Target Identification, RNF4 is an Essential NOA Gene in Cancer RNF4 Protein Levels are Abnormally Upregulated in Human-Derived Cob-Rectal Biopsies (FIGS. 1-5)

Evaluating patients-derived colo-rectal biopsies the inventors observed that RNF4 protein level is elevated in carcinoma in situ and colorectal carcinoma (CRC; FIGS. 1B-C') but not in benign adenoma of humans, or $APC^{min}$ mice model of intestinal adenoma (not shown). Moreover, high RNF4 protein level was observed in 30% of CRC biopsies (FIGS. 1C-C' p<0.001 n=99), and a high level of RNF4 mRNA correlates with a poor outcome of ER+-luminal "type A" breast cancer patients.

Figures 2A, 2B, 2C, 2D, 2E, 2F, 2G, 2H, 2I, 2J, 2K, 2L, 2M, 2N, 2O:
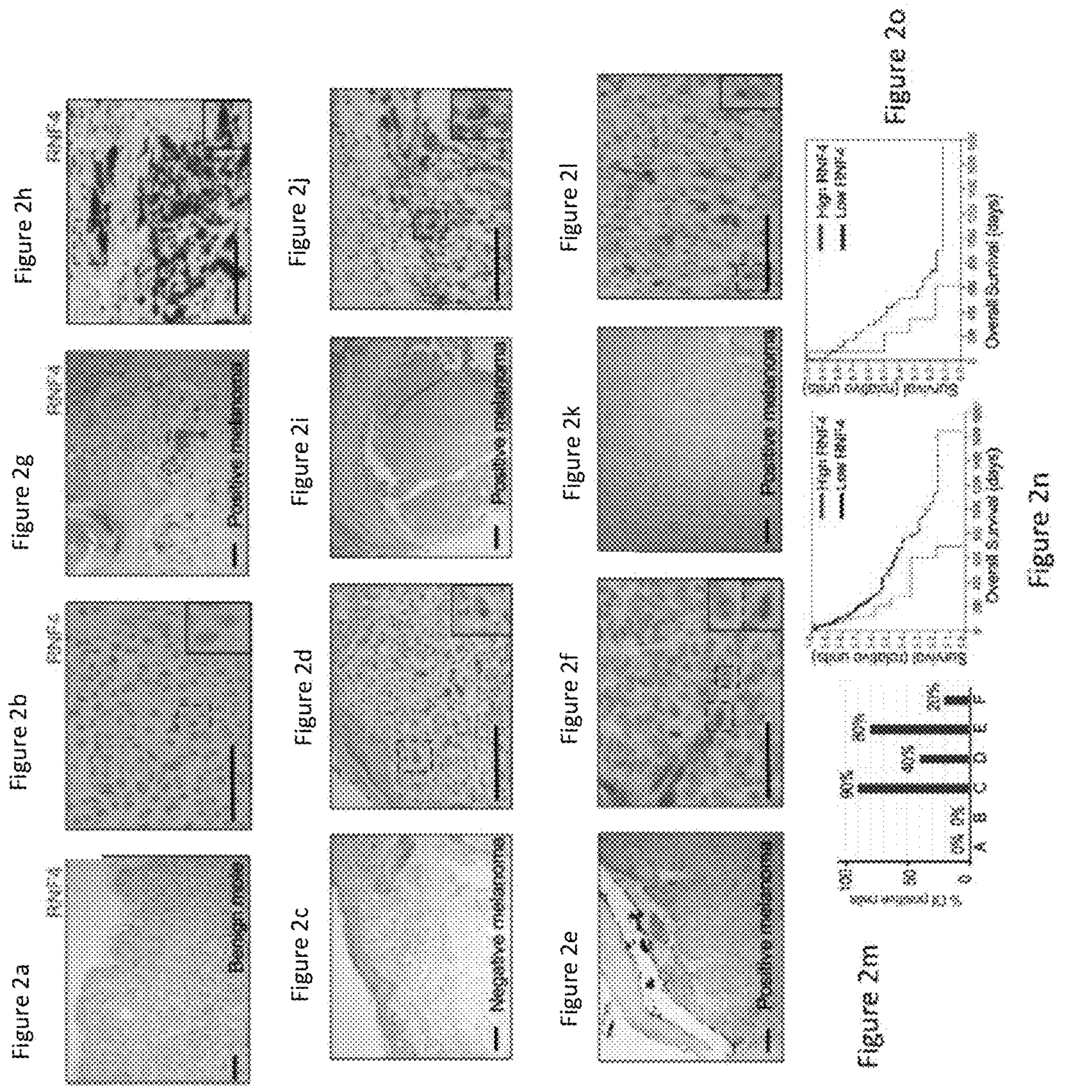

High RNF4 levels Correlate with Melanoma Development and Poor Prognosis of Patients High levels of RNF4 protein were observed in 50% of patient-derived melanoma samples but rarely in nevi (benign lesion; FIGS. 2A, 2B-M, n=30; 13). Screening samples of melanoma patients we found that high RNF4 mRNA levels is associated with poorer survival (FIGS. 2N; n=330, p<0.05; not shown). At the protein level, using patient-derived TMA, and our monoclonal anti-RNF4 antibody (8D10 mAb), we found that patients exhibiting melanomas expressing high levels of RNF4 protein are characterized with poorer prognosis compare to low expression (FIG. 2O, n=28).

RNF4 is Essential for Tumorigenic Properties of Cancer Cells

Figures 3A, 3B, 3C, 3D, 3E, 3F:
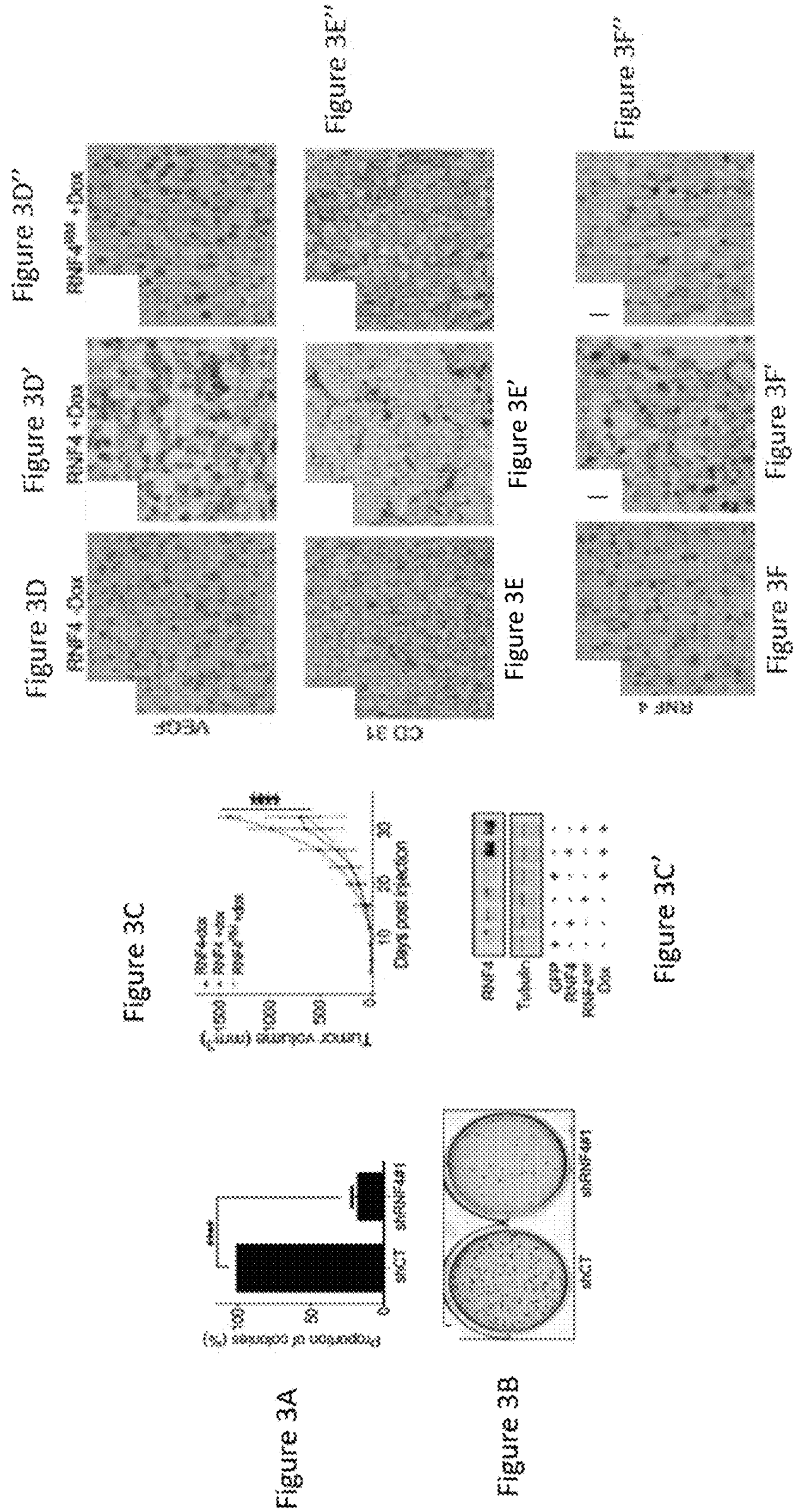
FIGS. 3A-F" include micrographs and graphs showing RNF4 potentiates tumorigenicity of melanoma in culture and in vivo: Colony formation assay of A375 cells in soft agar (FIG. 3A). Cells were infected with the control (shCT) or shRNF4 coding vectors, **=P<0.001; n=3 (representative wells. RNF4 potentiates melanoma tumorigenesis in vivo (FIG. 3B). Tumor size of A375-expressing Dox-inducible RNF4 or RNF4C159A catalytic inactive RING mutant ($RNF4^{RM}$) injected subcutaneously to xenograft nude mice in the absence or presence of Doxycyclin, as indicated (−/+Dox; n=7 per group; **=p<0.0001) (FIG. 3C). Western blot analysis of RNF4 protein level in transplanted A375 cells at time of transplantation (FIG. 3C'). Representative immuno-histochemistry images with indicated antibodies (FIGS. 3D-F"). Doxycyclin induced the expression of RNF4 (FIGS. 3D'-3F') or $RNF4^{RM}$ (FIGS. 3D"-3F")

The above data fits well with the effects of RNF4 in experimental biological assays. The survival of human MeWo or A375 melanoma cells is reduced upon Doxycycline-induced (Dox) conditional targeting of shRNF4 but not control scRNA. Targeting RNF4 also resulted in reduced ability to form colonies in soft agar and attenuated cell migration in trans-well assay (FIGS. 3A-B). Similar results were observed in aggressive breast cancer cell lines (e.g. MDA-MB231, and osteosarcoma.

RNF4 Potentiate Tumorigenesis of Epithelial Cells

In several biological settings, RNF4 potentiates the cancerous phenotype. For example, conditional expression of RNF4, but not RNF4 mutants that cannot bind to phosphorylated proteins or are catalytically inactive RNF, enhanced colony formation capacity of otherwise non-aggressive SW480 CRC cell lines, thereby potentiating their tumorigenic capacity. Similar results were observed in MCF7 breast cancer cells.

RNF4 Potentiates Melanoma Tumorigenesis In Vivo

The inventors tested the impact of RNF4 on tumorigenesis in vivo by infecting A375 melanoma cells with lentiviral plasmids coding for Dox-induced RNF4 or catalytically inactive mutant ($RNF4^{RM}$)that were injected into nude mice. As shown in FIG. 3, Dox-induced expression of RNF4, but not a catalytic inactive mutant RNF4, resulted in larger and more vascular tumors (n=16 p<0.001; FIGS. 3C-F").

High RNF4 Levels Are Associated with Resistance to Therapy in Patients, and are Required for the Survival of Vemurafenib-Resistant Melanoma Cells in Culture and In Vivo One characteristic of melanoma aggressiveness is the development of resistance to targeted therapy. Resistance to PLX4032 (Vemurafenib®) an inhibitor of BRAFV600E, develops rapidly, and represents a clinical challenge, even in the era of immunotherapies.

Figures 4A, 4B, 4C, 4D, 4E, 4F, 4G, 4H, 4I:
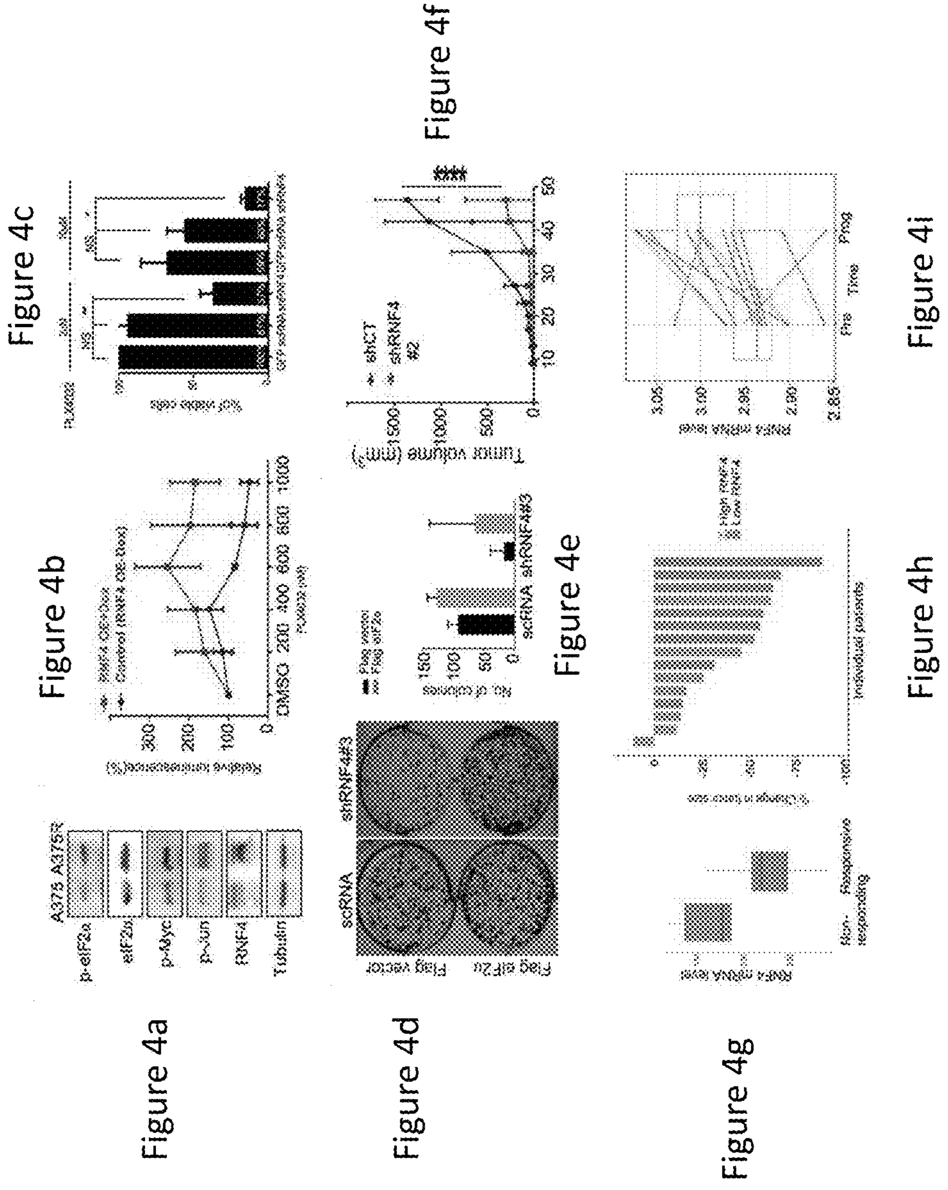
FIGS. 4A-I present graphs showing that RNF4 confers resistance to RTK inhibitors.

Given the role of RNF4 in melanoma tumorigenesis and the related MAPK signaling components, we studied the involvement of RNF4 in resistance to BRAF inhibition. Indeed, higher RNF4 protein levels as well as its stabilized substrates were elevated in PLX4032-resistant cell lines, such as A375R, LU1205R, UACC1113 (FIG. 4A). Both gain- and loss-of function experiments established a critical role for RNF4 in conferring resistance to PLX4032. Expression of RNF4 in A375 PLX4032-sensitive cells induced PLX-4032 resistance (FIG. 4B), and PLX4032-resistant A375 cells (A375R) expressing shRNF4 re-gained sensitivity to treatment (FIG. 4C). In accordance, A375R expressed higher RNF4 as well as higher p-eIF2α protein levels. Moreover, over-expression of eIF2α in A375R cells subjected to RNF4 knockdown, partially restored resistance to PLX4032 (FIGS. 4D-E).

To substantiate observations made in melanoma cells, we tested the effects of RNF4 knockdown on PLX4032-resistant xenografts in vivo. The inventors injected subcutaneously to nude mice, A375R cells expressing Dox-inducible shRNF4 or control (shRenilla). Control shRNA expressing A375R cells rapidly developed tumors (8/8) that resisted PLX4720 treatment. However, only 3/8 animals in the group injected with RNF4-knockdown cells developed tumors, that were notably smaller (p<0.0001, FIG. 4F).

Lastly, the inventors analyzed patient samples that were either sensitive or resistant to BRAF/MEK inhibition (FIGS. 4G-H). Higher RNF4 mRNA levels correlated with smaller reduction in tumor size (Mann whitney test p<0.04) and with failure to respond to treatment (Cohen's D=0.85, within top 1% of all protein coding genes). Moreover, upon progression, resistant tumors expressed higher RNF4 level (FIG. 4I; paired Wilcoxon ranksum p<0.02). This correlation suggests that RNF4 is likely to play an important role in the resistance to MAPK inhibition in melanoma patients. In summary, we established in vitro, in vivo and in patient-samples, that RNF4 promotes melanoma progression and resistance to targeted therapy which is partly mediated via p-eIF2α.

Example 2

Background on Mechanisms of Action and Eitope Selection

The inventors determined the mechanism of action of RNF4 in cancer. The inventors determined the molecular motifs required for its interaction with the stabilized oncoproteins. The inventors delineated the biochemical, molecular and transcriptional action of RNF4 together with these oncoproteins including the targeting epitope within RNF4 as well as specific peptide sequences with the stabilized oncoproteins.

RNF4 Stabilizes, Ubiquitylates and Binds to Phosphorylated β-Catenin and c-Myc

Figures 5A, 5B, 5C, 5D, 5E, 5F:
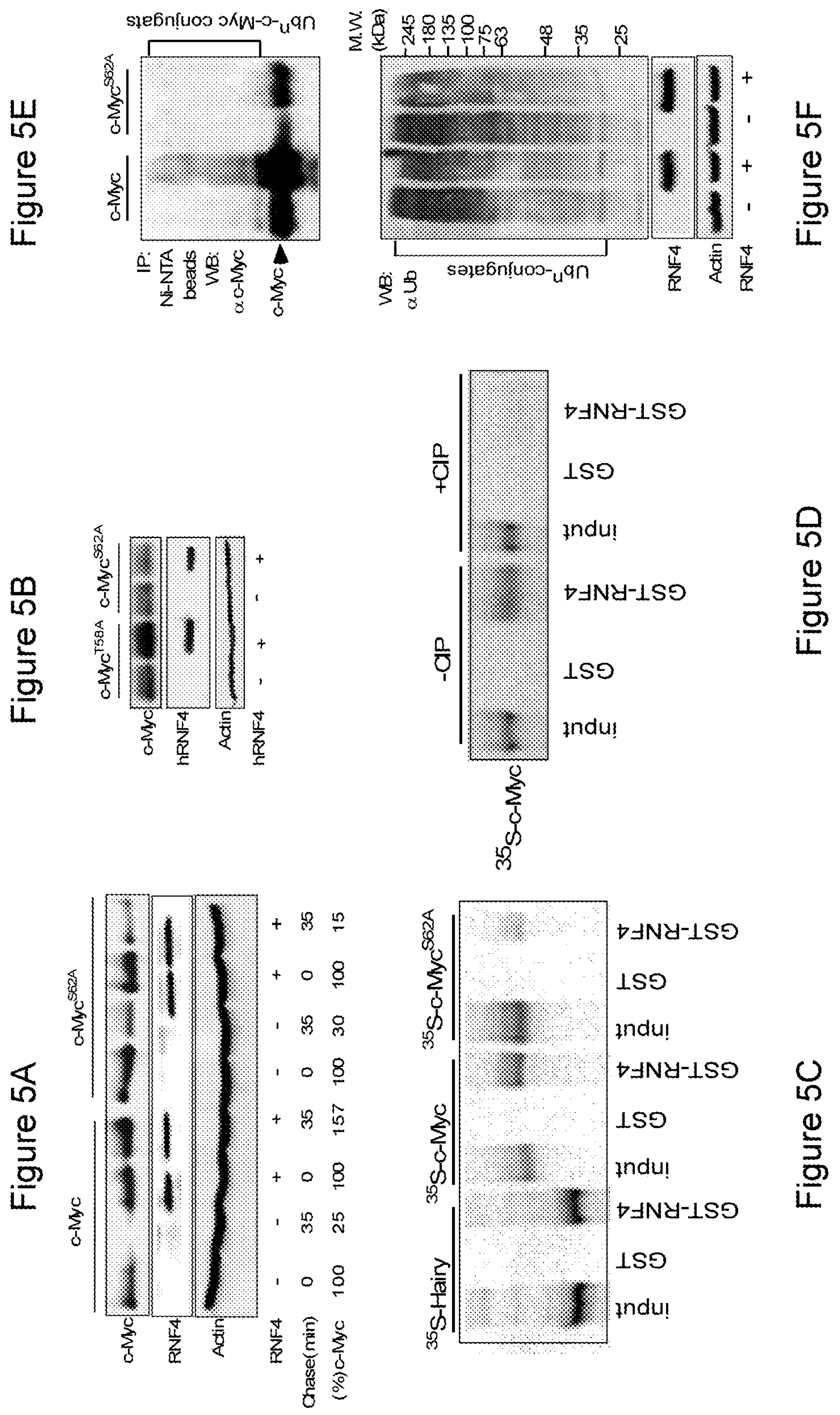
FIGS. 5A-F show that phosphorylation of Ser62 within c-Myc is required for RNF4-dependent stabilization, binding, and ubiquitylation of c-Myc.

The inventors found that an initial phosphorylation by mitogenic kinases (e.g., p-S62-c-Myc, p-S45β-catenin, p-c-Jun) is required for RNF4 interaction with these oncoproteins. Mutations abolishing these phosphorylations such as C-Myc$^{S62A}$ inhibit binding, ubiquitylation and stabilization by RNF4 (FIG. 5). Thus, in addition to its known functions, RNF4 translates transient phosphorylation signals into long-term protein stability.

An Arginine-Rich-Region is Required for RNF4 Binding, Stabilization and Transcriptional Activation of Oncogenic Transcription Factors RNF4 binds and potentiates the stability and activity of its oncogenic substrates directly. The interaction solely depends on RNF4's Arginine rich motif (ARM), and site-specific phosphorylation of these oncoproteins. RNF4 deletion mutant lacking the ARM domain (a.a. 72-82 in human RNF4, see FIG. 7A) fails to bind in vitro and ubiquitylate these oncoproteins in cells. Subsequently RNF4$^{\Delta ARM}$ fails to stabilize these proteins, as well as to enhance their transcriptional activity (FIG. 6).

Figures 6A, 6B, 6C, 6D, 6E, 6F:
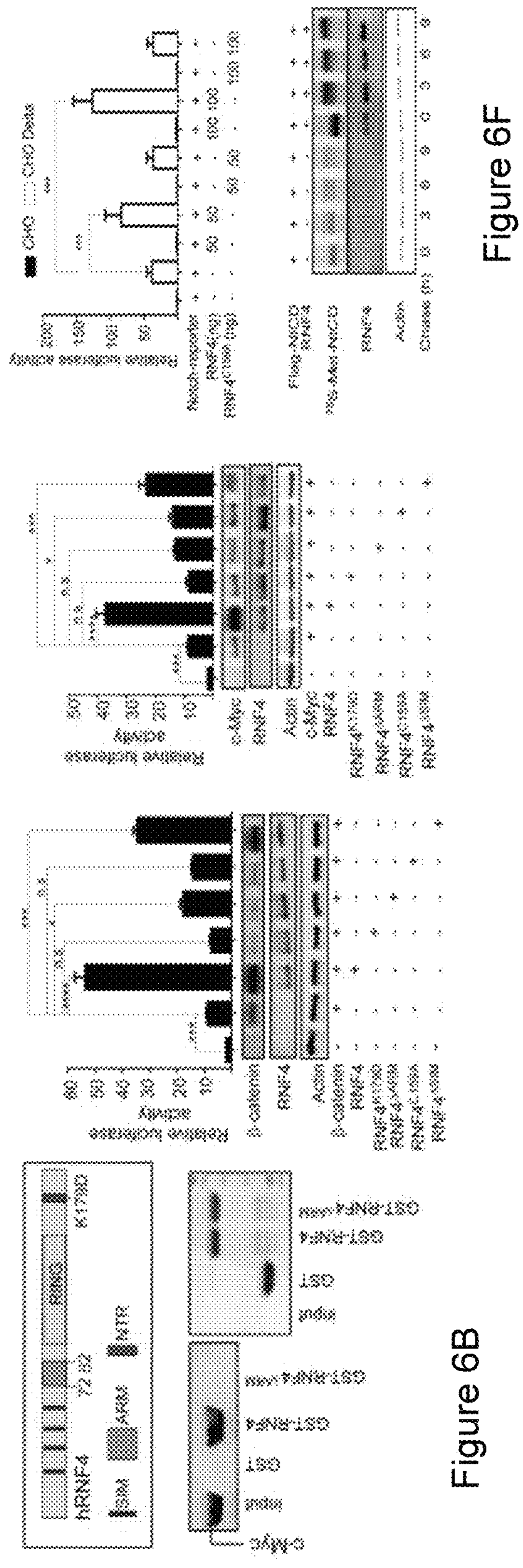
FIGS. 6A-F show the mode of RNF4 action.

In accordance, RNF4$^{\Delta\Delta ARM}$ fails to potentiate tumorigenic properties of cancer cell similarly to the observed with the RNF4 RING mutant including transcriptional activation (FIGS. 6 C-F). Please note that the ARM domain is unique and is not present in the most closely-related ligase, RNF111, Arkadia, further demonstrating the uniqueness of the epitope. Moreover, mutant RNF4, RNF4$^{K179D}$ that cannot bind to nucleosomes fails to stabilize, or enhance the transcriptional activity of these oncoproteins (FIG. 6C).

Figures 7A, 7B, 7C, 7D:
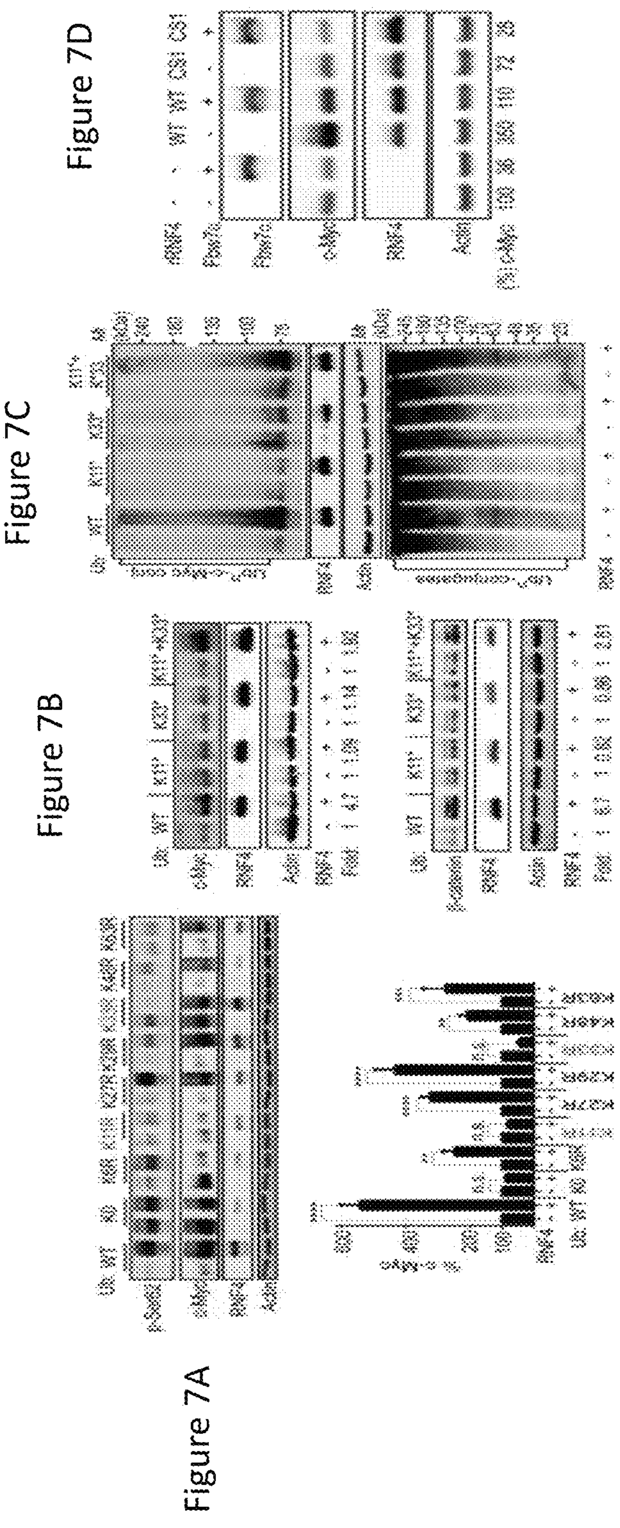
FIGS. 7A-D show c-Myc stabilization requires RNF4-dependent catalysis of K11/K33 containing poly-ubiquitin chains.

Atypical Poly-Ubiquitin Chains are Required for RNF4-Dependent Oncoprotein Stabilization The inventors determined that RNF4-dependent stabilization requires the catalysis of atypical ubiquitin chains with internal linkage of K11, K33 of ubiquitin (FIGS. 7A-B). Remarkably, using ubiquitin mutants that each contain only a single Lys residue (K*), the inventors found that only co-expression of K11* and K33* together was sufficient for the stabilization and ubiquitylation of c-Myc and β-catenin (FIG. 7C).

RNF4 Activity Does not Affect SCF Ligase or Impact on UBC (Ub-E2s)

Substrates stabilized by RNF4 like c-Myc, PGC1α, NICD, CycE, and c-Jun, are all substrates for the SCF ligase complexes such as SCF$^{FbW7}$. However, RNF4 was able to stabilize c-Myc in SCFF$^{bW7\ -/-}$ null cells, and expression of SCF$^{FbW7}$ ligase resulted in degradation of RNF4-stabilized c-Myc (FIG. 7D). In addition, the inventors found that other components of the SCF complex/proteasome are not affected by RNF4. Furthermore, RNF4 can further stabilize and enhance the activity of oncoprotein with that harbor a degradation resistant mutation (e.g. Myc$^{T58A}$) Thus, the stabilizing effects of RNF4 are independent of the SCF ligase complex involved in the degradation of these oncoproteins.

Figure 8:
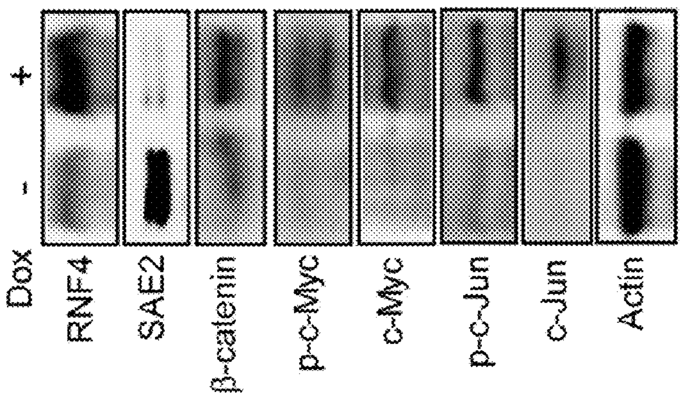
FIG. 8 shows that RNF4 stabilizes oncoproteins independent of de-novo SUMOylatio: Endogenous oncoproteins in MDA-MB231$^{shSAE2}$ are stabilized by Dox co-expressing RNF4 and at the same time targeting the SAE2 subunit of the SUMO E1 activating enzyme inhibiting SUMOylation. Suggesting, that oncoprotein stabilization is independent of de-novo SUMOylation.
Figure 9A:
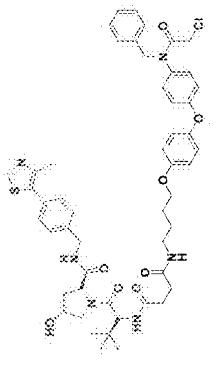
FIGS. 9A-E show the structure of R4VP and R4VP derivatives.
Figure 9B:
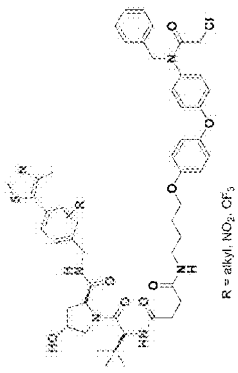
Figure 9C:
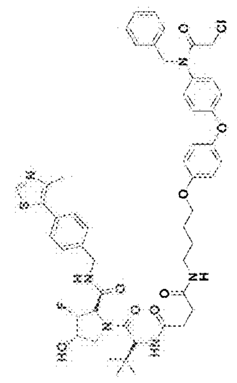
Figure 9D:
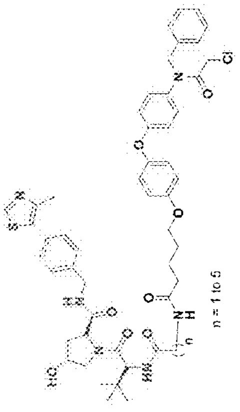
Figure 9E:
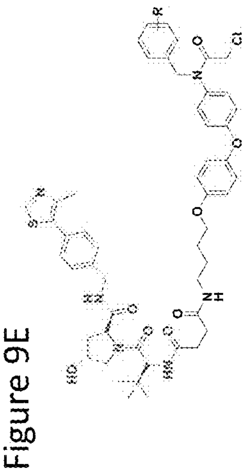

RNF4 Stabilizing and Tumor Potentiating Activity is Independent of Covalent SUMOylation The tumor potentiating activities are independent of RNF4's SIM motifs that mediated interactions with SUMOylated proteins. Conditional expression of RNF4 stabilizes endogenous oncoprotein also in cells where covalent SUMOylation was co-inhibited by the conditional targeting of the SUMO E1 subunits SAE2 (FIG. 8).

Example 3

Development of RNF4-VHL-PROTAC (R4VP)

Development of RNF4-VHL-PROTAC (R4VP)

The inventors generated a novel molecule termed RNF4-VHL-PROTAC (R4VP) and designed additional related molecules that the inventors predict that can be more potent.

Figure 10:
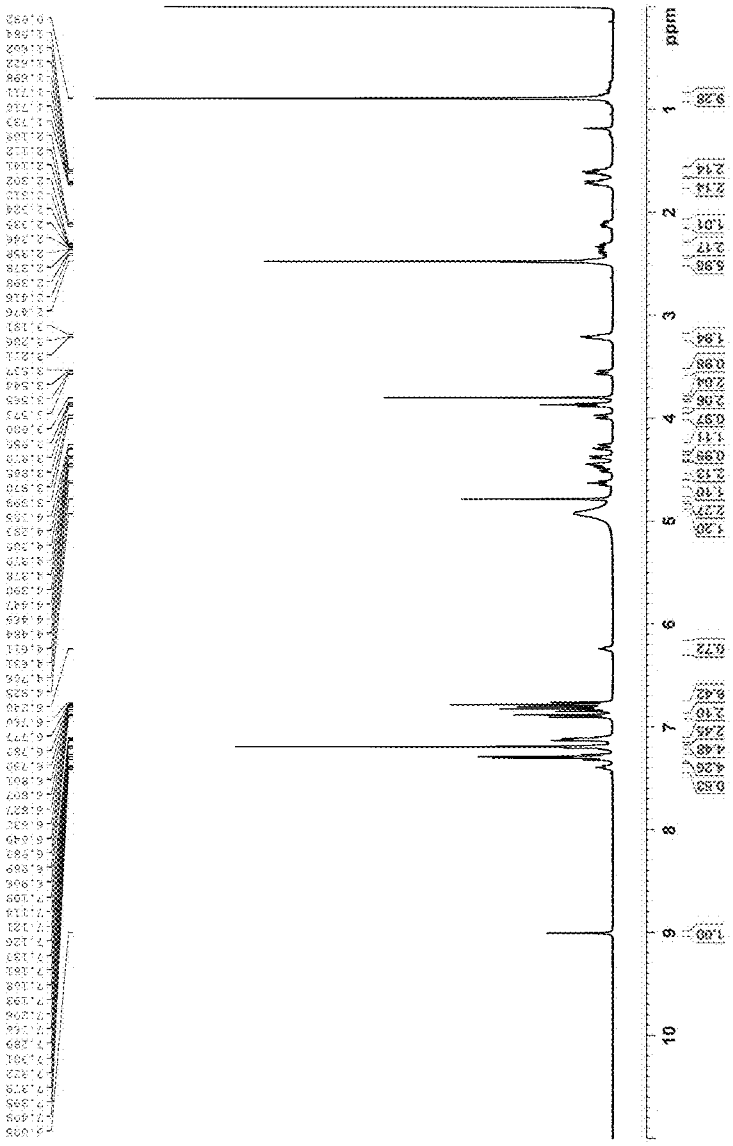
FIG. 10 includes a proton NMR spectra analysis of RNF4-VHL-PROTAC (R4VP)

(FIGS. 9-10). R4VP is a novel bi-functional molecule; one head of the molecule binds to the ubiquitin ligase VHL, and the second head binds to RNF4. Thus the molecule bridges between RNF4 and VHL. The chemical details of the generation of R4VP molecules are described under methods. The inventors also designed modified R4VP-related molecules (FIGS. 9B-E). The composition of R4VP was validated by Proton NMR analysis (FIG. 10).

R4VP Targets RNF4 for Degradation by the Proteasome

Figure 11C:
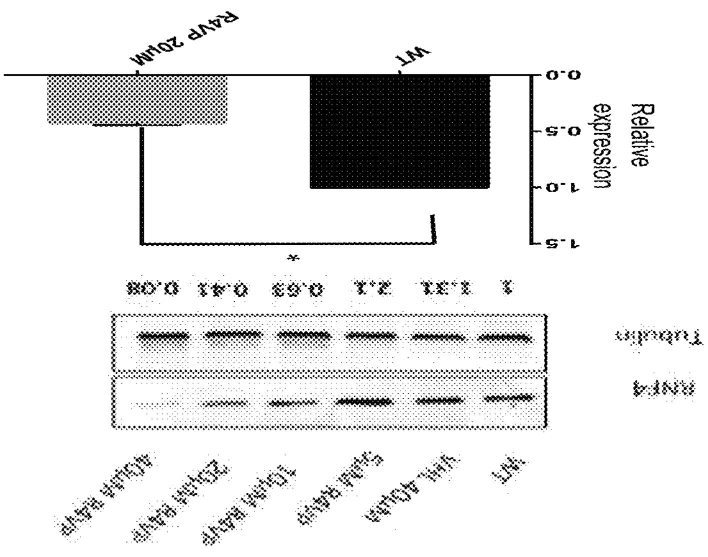
FIGS. 11A-C show that RNF4-VHL-PROTAC (R4VP) induced degradation of RNF4. Western blot analysis of protein extract derived from A375R cells. Transfected HA-RNF4 (FIG. 11A) protein, or endogenous RNF4 (FIG. 11B). Protein levels are reduced upon addition of R4VP for three hours. RNF4 protein levels are restored to levels similar to control treated cells in the presence of 40 mM proteasome inhibitor MG132. RNF4-VHL-PROTAC (R4VP) reduces the level of endogenous RNF4 in A375 melanoma cells in a dose dependent manner (FIG. 11C).
Figure 11B:
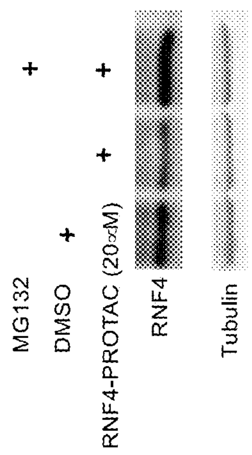
Figure 11A:
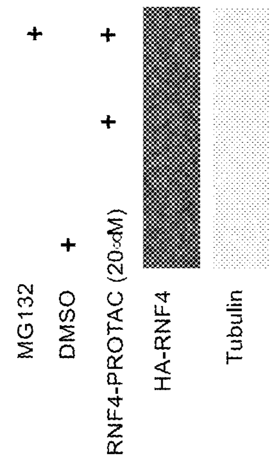

Three hours treatment of cancer cells with R4VP resulted in reduced the level of exogenous or endogenous RNF4 protein but not of VHL. Moreover R4VP-dependent degradation of RNF4 can be inhibited by the proteasome inhibitor MG132 (FIG. 11).

R4VP Inhibits Proliferation of Vemurafenib-Resistant Melanoma

Figure 13:
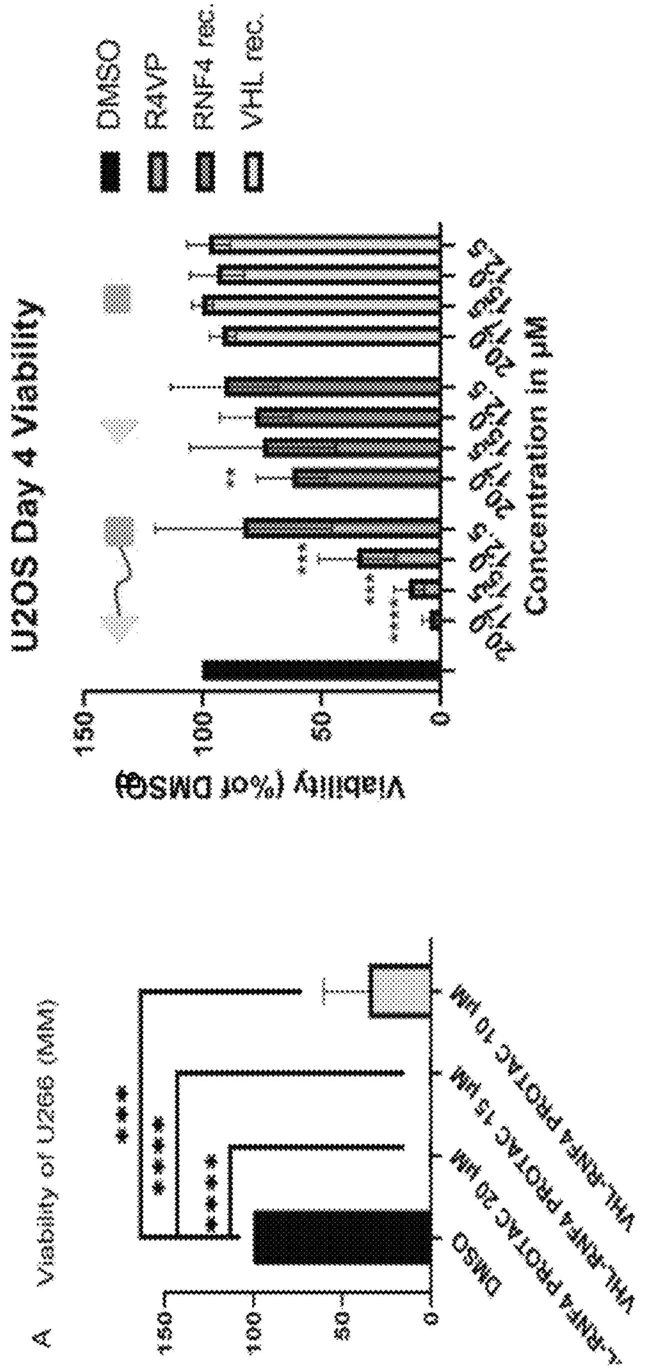
FIG. 13 shows that RNF4-VHL-PROTAC (R4VP) inhibits Multiple Myeloma and osteosarcoma cells proliferation: (Left panel) RNF4-VHL-PROTAC (R4VP) inhibits proliferation of human Myeloma U266cells as determined by MTT assay. (Right panel) RNF4-VHL-PROTAC (R4VP) inhibits proliferation of U2OS human osteosarcoma cells in a dose dependent manner as determined by MTT assay. Cell were treated for three hours with the indicated compound: R4VP (denoted as triangle and square connected), RNF4 binder only (triangle only), VHL recruiter (square only)

R4VP inhibited the growth and proliferation of Vemurafenib-resistant melanoma cells (A375R) at concentration as of 10 μM and above (FIG. 12). Moreover, control compounds such as the VHL or RNF4 binding portions of the R4VP molecule had minimal or no effect. R4VP growth inhibitory effects were also observed in osteosarcoma (U2Os) and Multiple Myeloma cancer cells (U266) in similar concentrations (FIG. 13).

Figure 14:
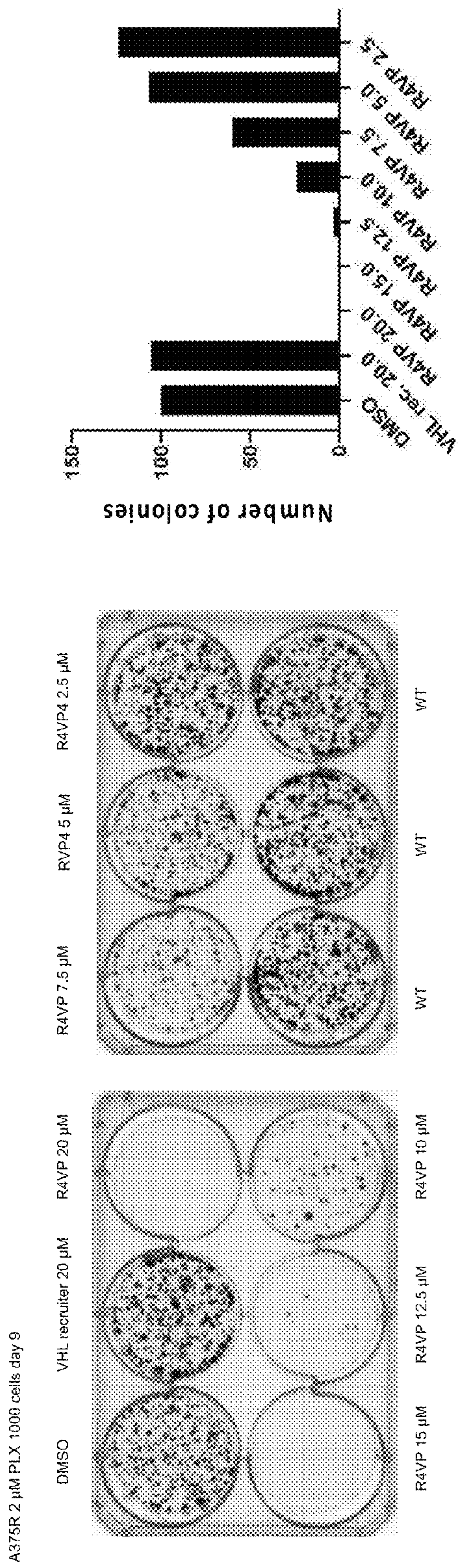
FIG. 14 shows that RNF4-VHL-PROTAC (R4VP) inhibits colony formation of PLX-resistant A375 human Melanoma cells: RNF4-VHL-PROTAC (R4VP) but not VHL only PROTAC (VHL), or DMSO, inhibits colony formation of human A375R melanoma (upper panel). The indicated PROTAC molecule was added at time of cell seeding at the indicated concentration. Colonies were visualized 8 d after seeding (A375R and U2Os respectively). Quantification of the number of colonies in each well is shown below in the bar graph.
Figure 15:
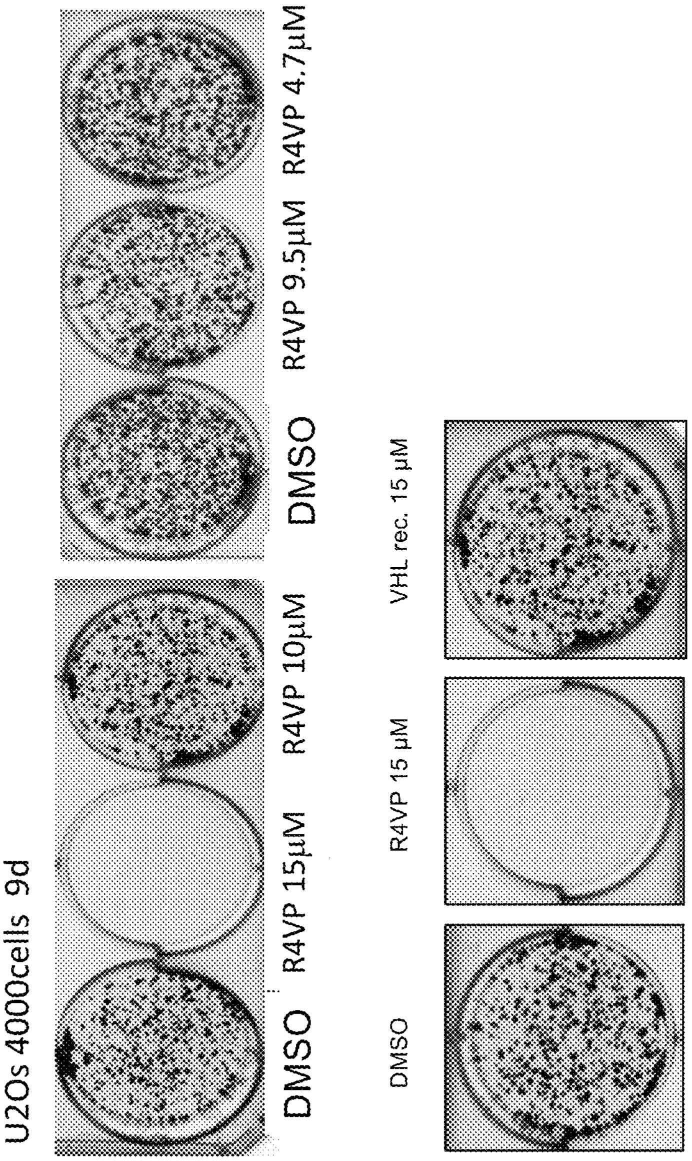
FIG. 15 shows that RNF4-VHL-PROTAC (R4VP) inhibits colony formation of U2OS osteosarcoma cells: RNF4-VHL-PROTAC (R4VP) but not VHL only PROTAC (VHL), or DMSO, inhibits colony formation of human U2OS sarcoma cells. The indicated PROTAC molecule was added at time of cell seeding at the indicated concentration. Colonies were visualized 9 d after seeding (U2Os respectively).
Figure 16:
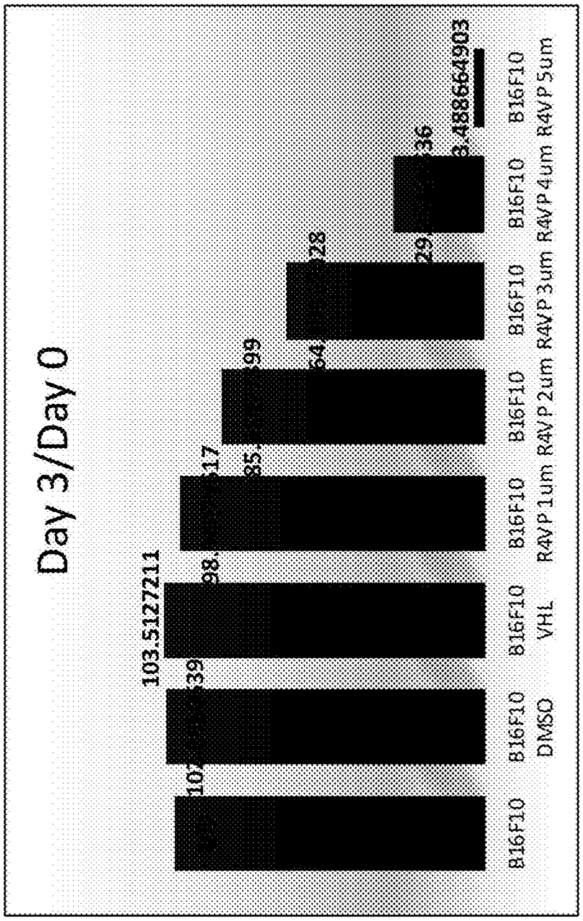
FIGS. 16A-B show that RNF4-VHL-PROTAC, but not VHL-only PROTAC, inhibits cell proliferation and colony formation of B16F10 aggressive melanoma cells. RNF4-VHL-PROTAC (R4VP) or VHL-only PROTACS were added at the indicate times and colonies were visualized after 9 days.
FIG. 16C is an image representing colony formation of b16F10 cells treated with control, VHL-only PROTAC or R4VPat the indicated concentrations for nine days.
Figure 16:
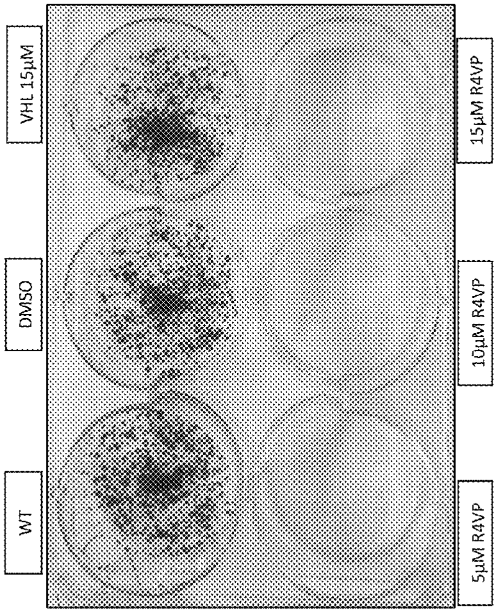
Figure 16:
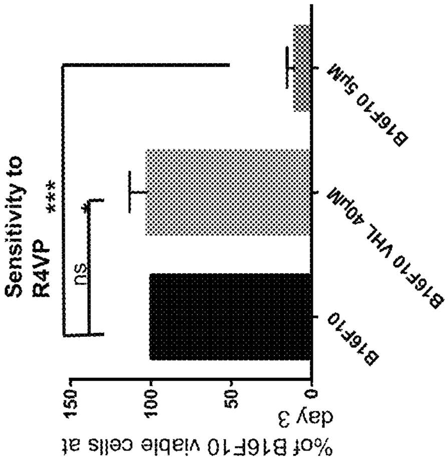

Addition of R4VP to culture media inhibited colony formation of melanoma and osteosarcoma cells in a dose dependent manner, while the VHL only portion of the molecule had not such effect (FIGS. 14, 15). Likewise, R4VP inhibits proliferation and colony formation of B16F10 murine melanoma cells (FIG. 16A-C).

Figure 17:
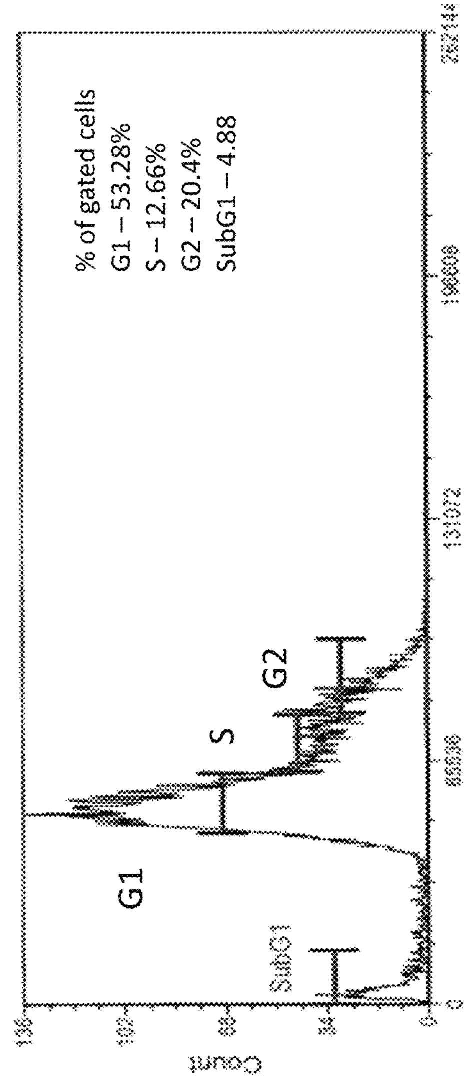
FIGS. 17A-B show that treatment of A375R melanoma cells that are resistant to Vemurafenib therapy results in cell-death as evident by FACS analysis with the accumulation of cells in Sub-G1 three hours after the exposure to RNF4-VHL-PROTAC.
Figure 17:
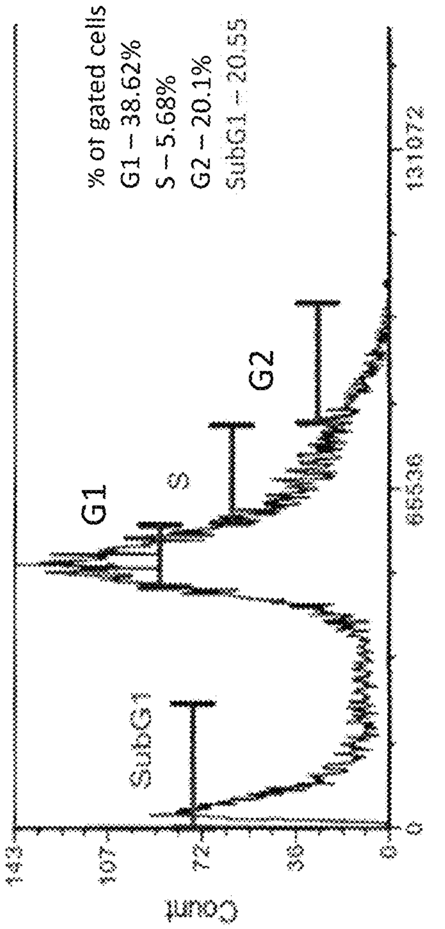

R4VP induces cell death. Short treatment (3 h) of human RTK-resistant melanoma cell by R4VP results in extensive cell death as determined by the increase in sub-G1 cells using FACS analysis (FIG. 17A-B).

Figure 18:
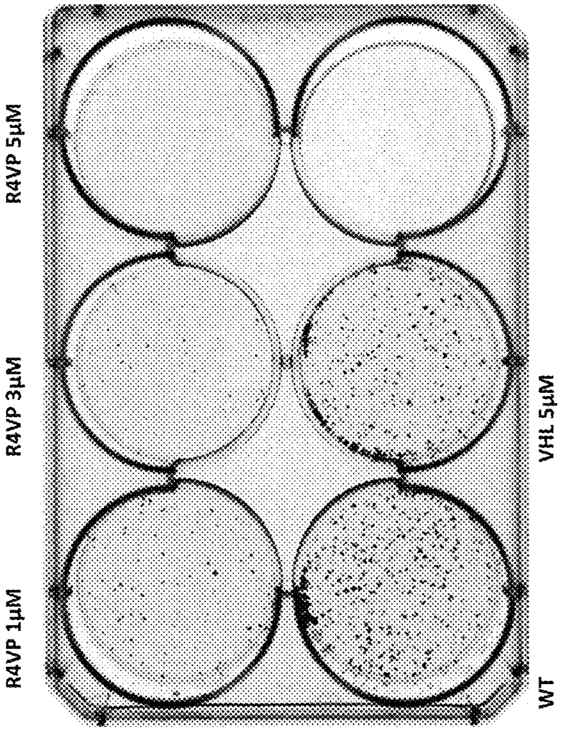
FIGS. 18A-C show that RNF4-VHL-PROTAC acts at the single μM range (1, 3 and 5 μM) inhibiting colony formation of tumorigenic human squamous skin cancer cells (SCC1), as demonstrated by FIG. 18A but not of human non-tumorigenic cell line of keratinocytes HeCat, as demonstrated by FIG. 18B. VHL-only PROTAC serves as control.
Figure 18:
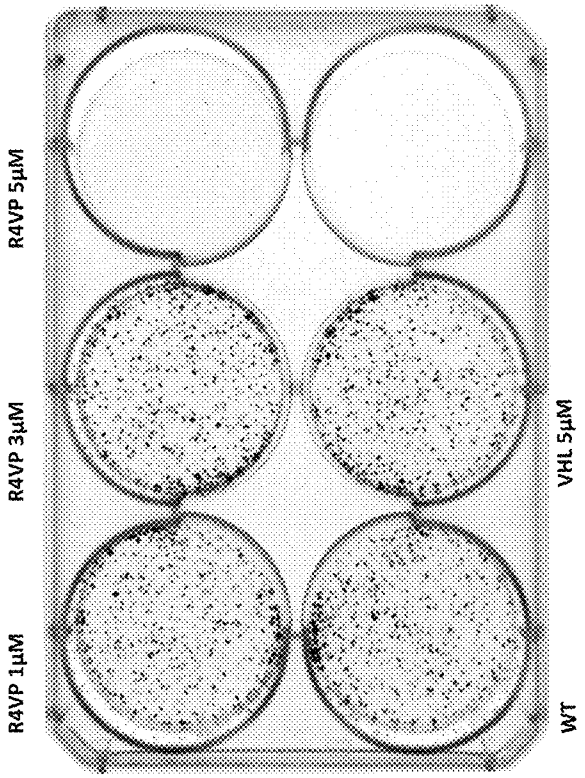
Figure 18C:
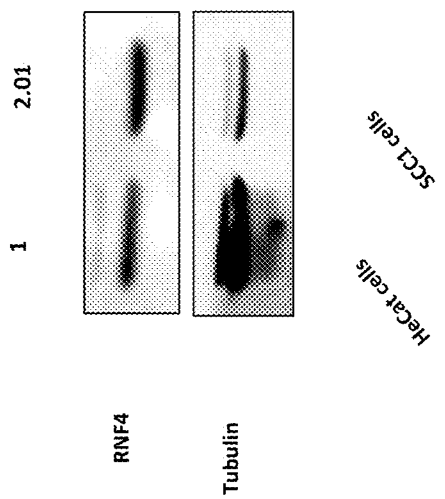

R4VP has differential activity towards tumorigenic cells. We observed that human squamous cell carcinoma cell line (HCC1) is sensitive to R4VPat the single low μM range [IC50<1 μM]. In contrast, non-tumorigenic human keratinocyte cell line HeCat were not affected at these concentrations (1-3 μM) (FIG. 18A-C).

Example 4

Structural Modifications of RNF4-VHL-PROTAC (R4VP)

A variety of modifications on the R4VP molecule can be performed.

An exemplary synthetic route for structural modifications on the phenyl ring of VHL ligand is as follows:

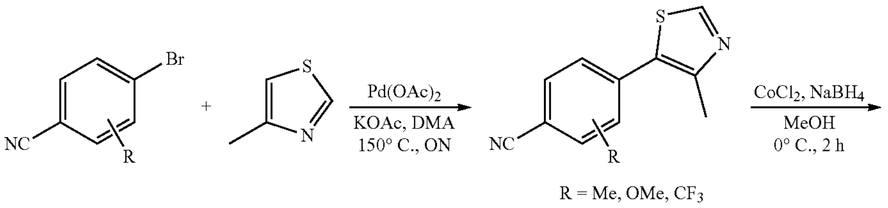

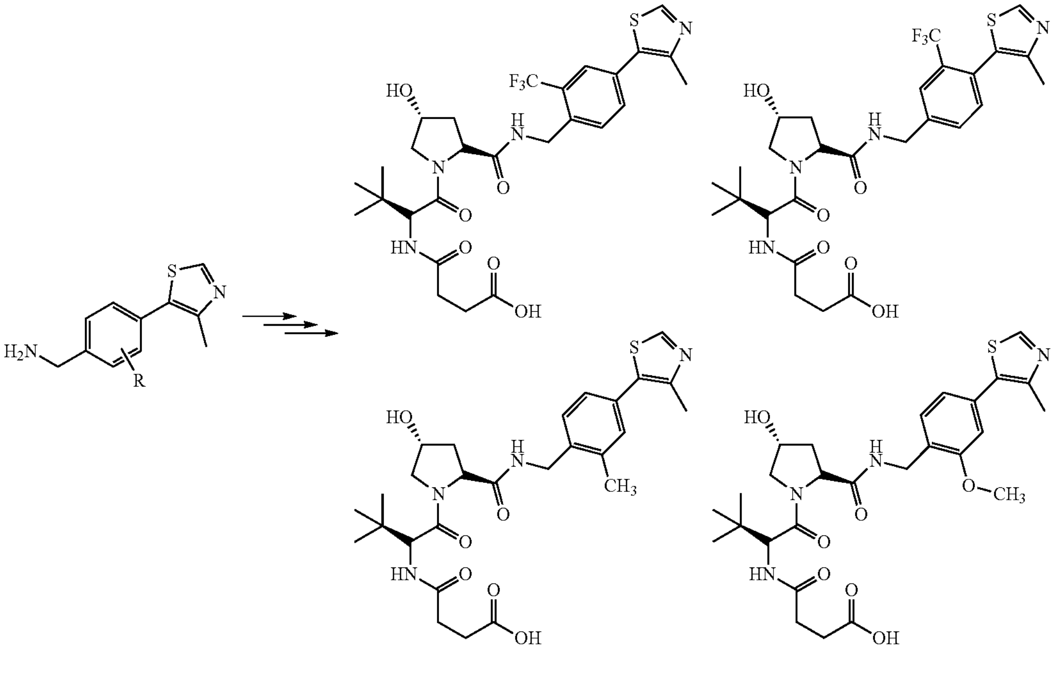

An exemplary synthetic route for structural modifications on the phenyl ring A of RNF4 ligand is as follows:
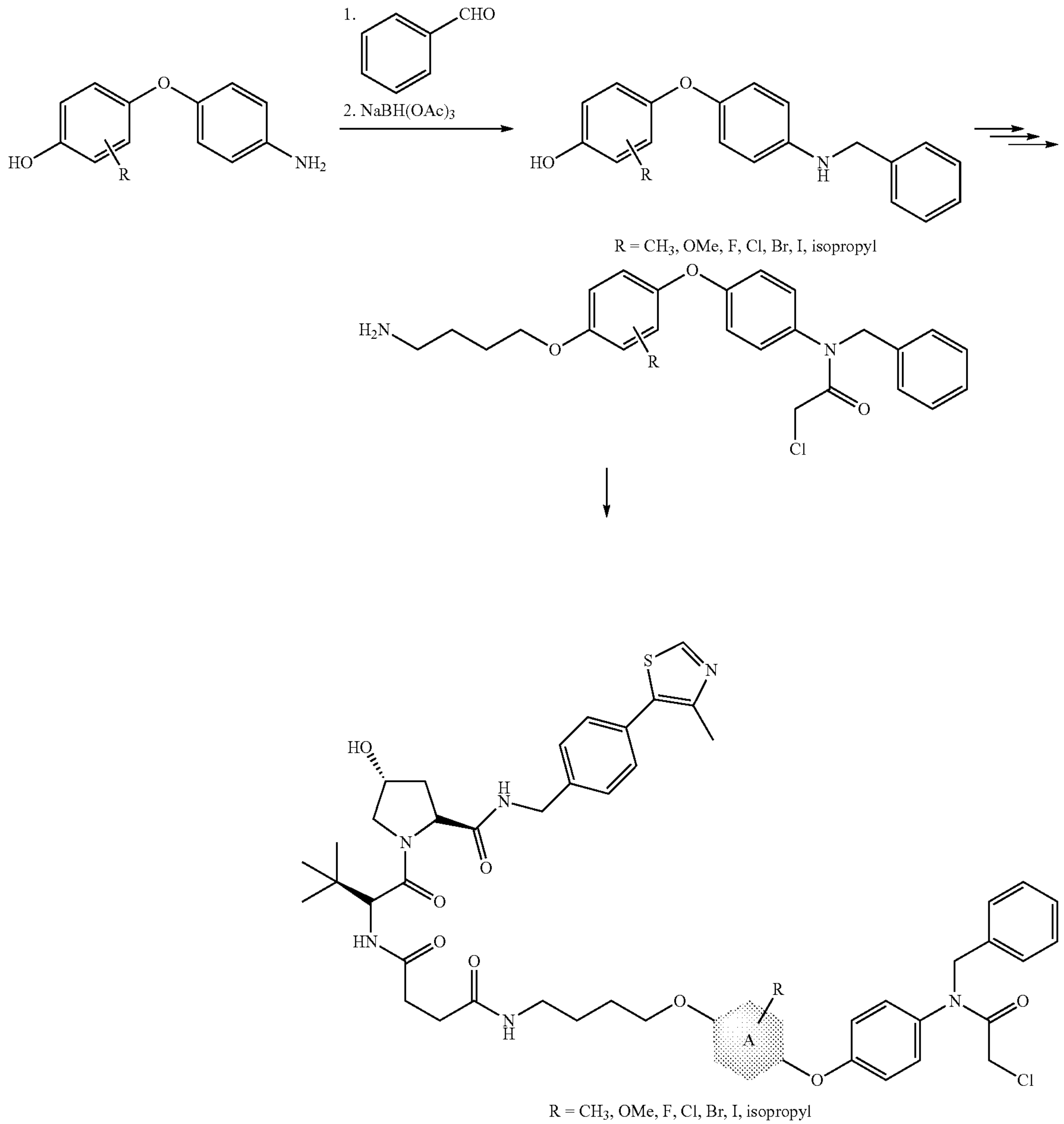
An exemplary synthetic route for structural modifications on the phenyl ring B of RNF4 ligand is as follows:
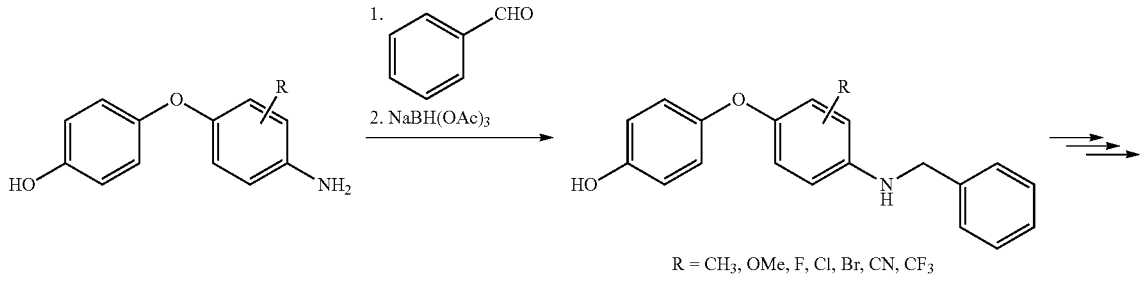

-continued
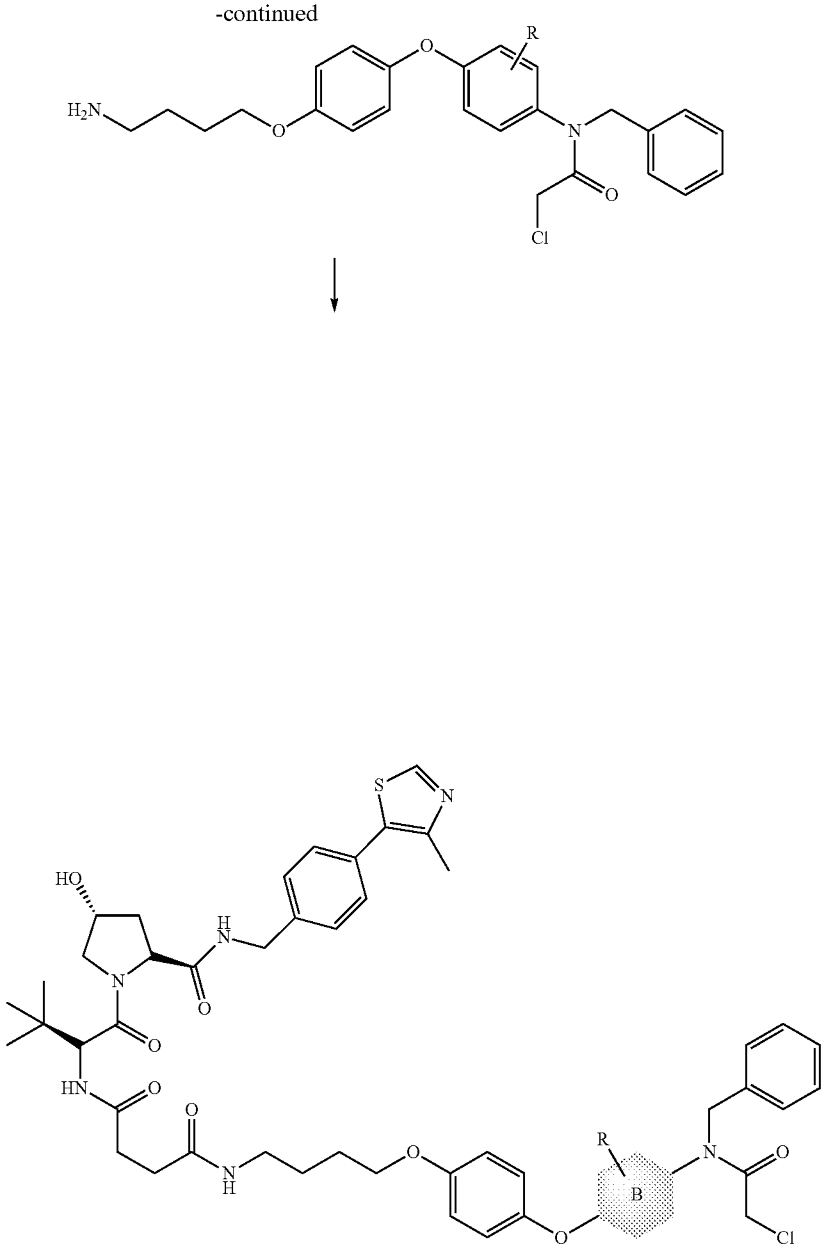
R = $CH_3$, OMe, F, Cl, Br, CN, $CF_3$
An exemplary synthetic route for structural modifications on the phenyl ring C of RNF4 ligand is as follows:
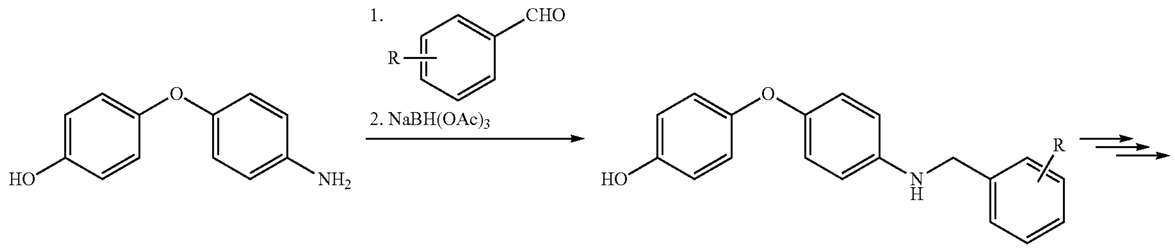
R = halogen, alkyl, $NO_2$, $CF_3$ -continued
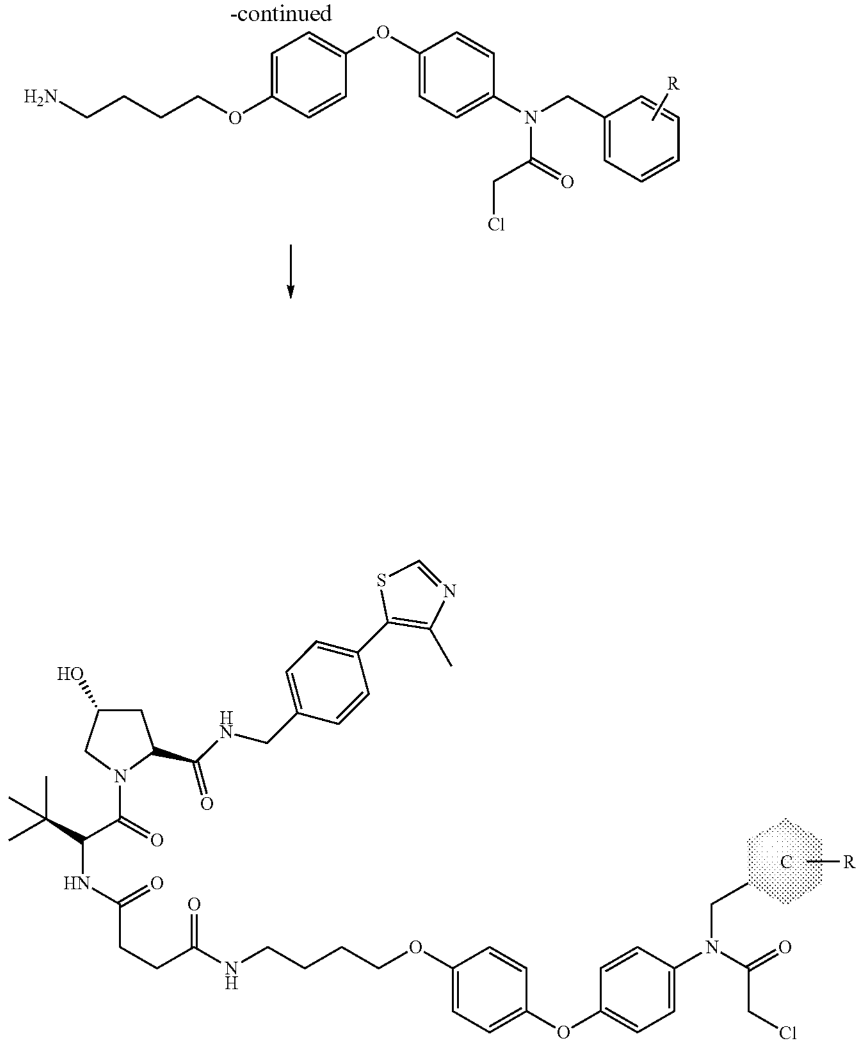
R = halogen, alkyl, $NO_2$, $CF_3$
An exemplary synthetic route for structural modifications on the phenyl ring C with a variety of pyridine rings is as follows:
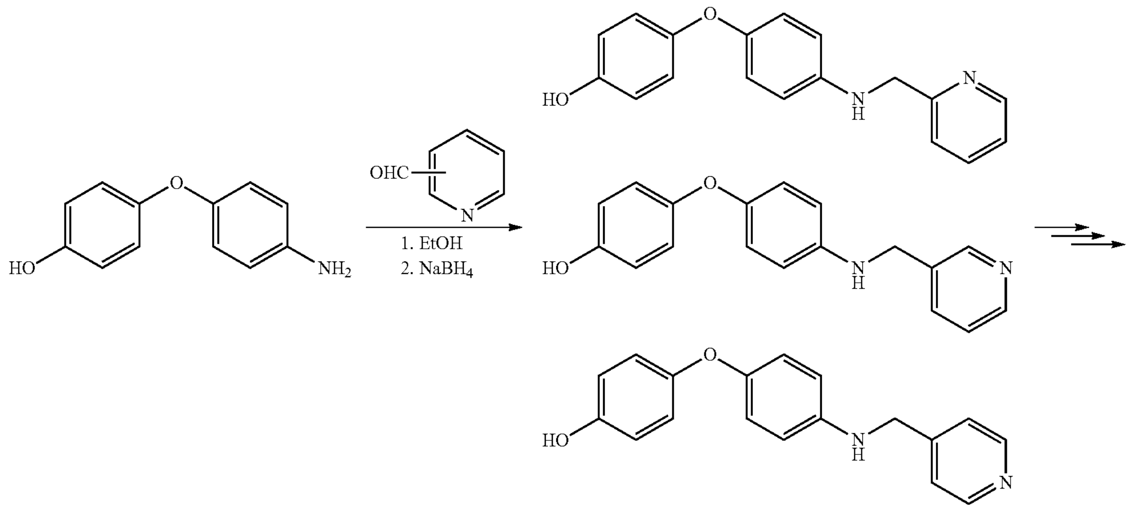

-continued
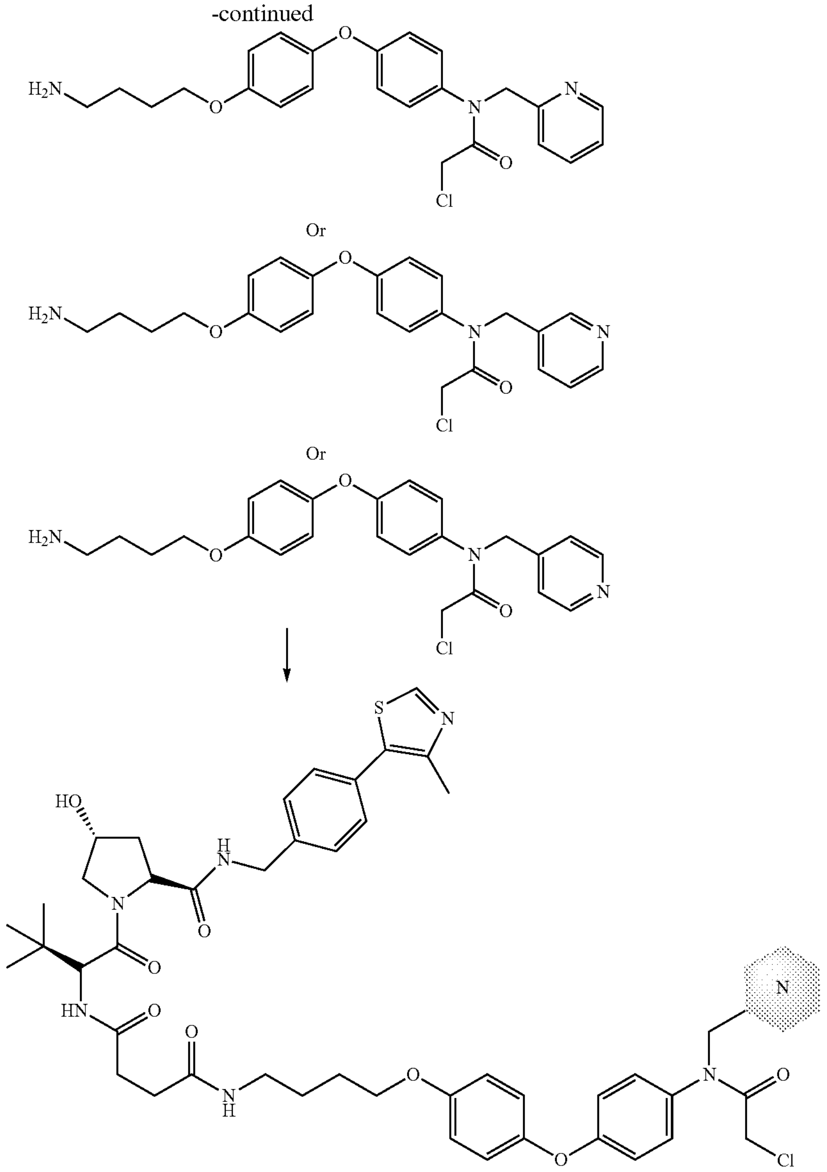
An exemplary synthetic route for structural modifications on the phenyl ring C with a variety of five-membered rings such as oxazoles, pyrroles, and thiazoles is as follows:
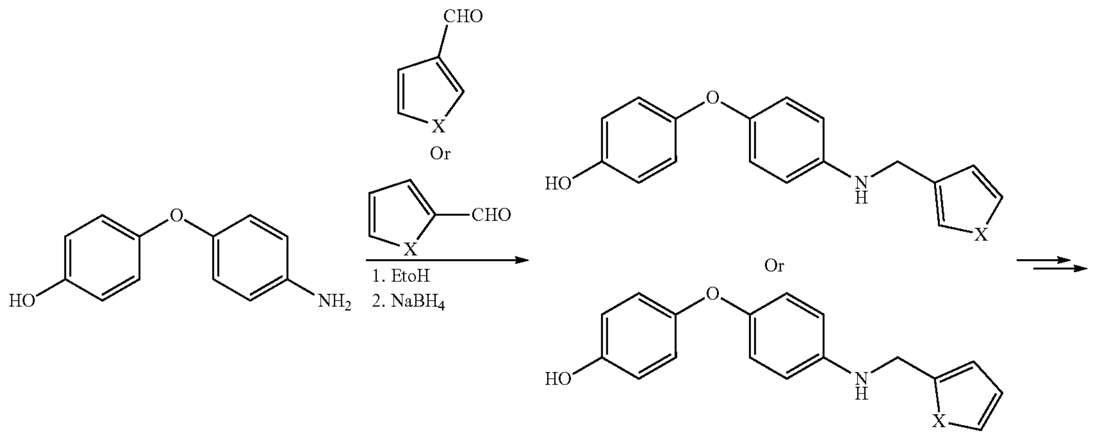

-continued
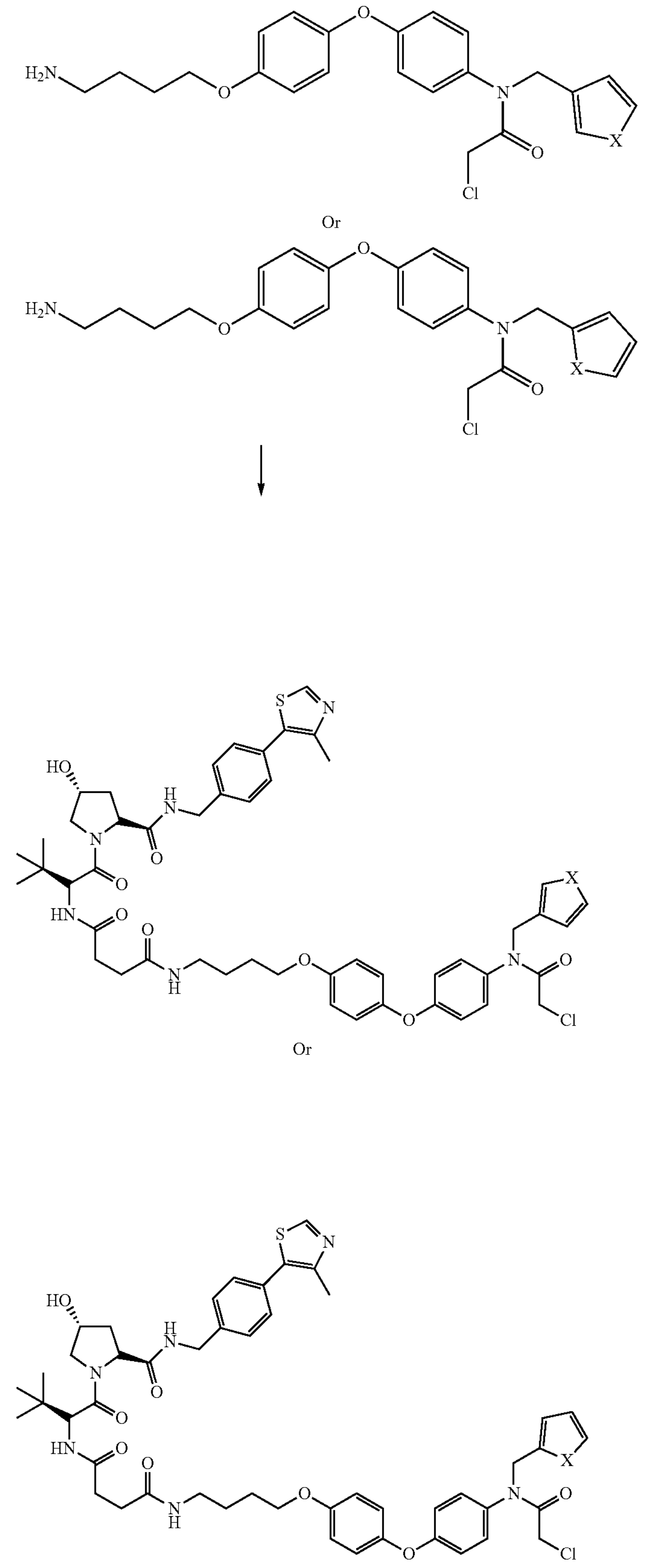
X = O, N, S

The linker length can be modified by changing the carbon chain in the sequence and also, one or multiple polyethylene glycol (PEG) units can be included to enhance the solubility. An exemplary synthetic route for structural modifications on the linker of VHL ligand is as follows:
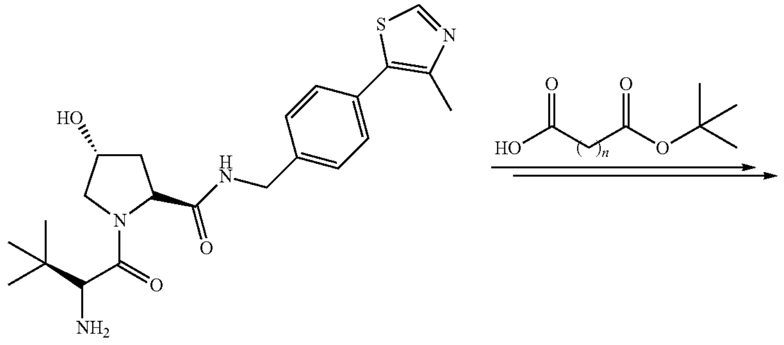
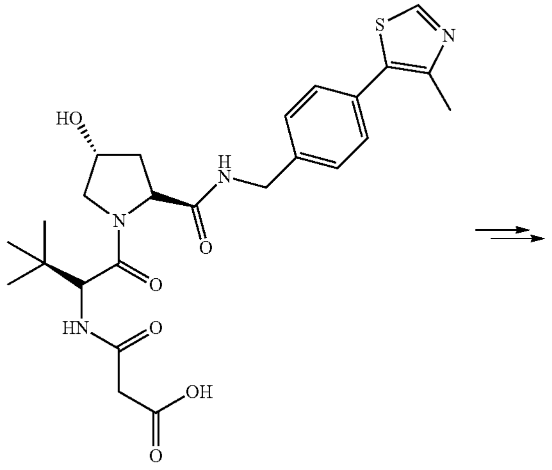
n = 1 to 6
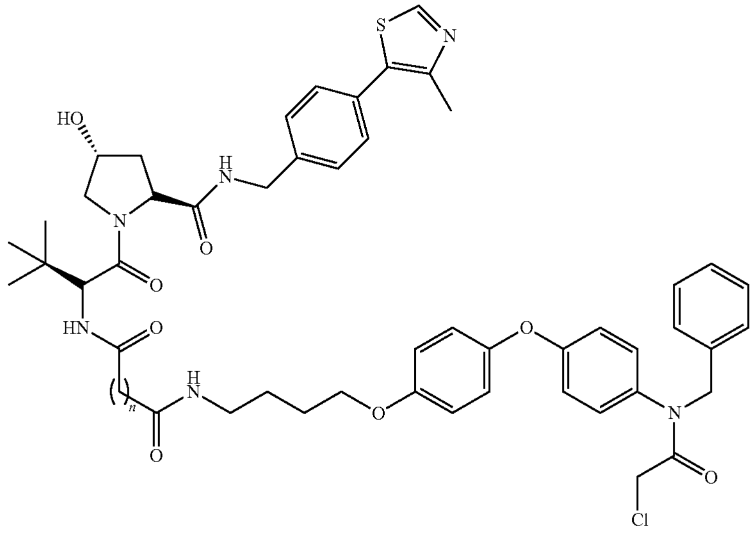
n = 1 to 6

-continued

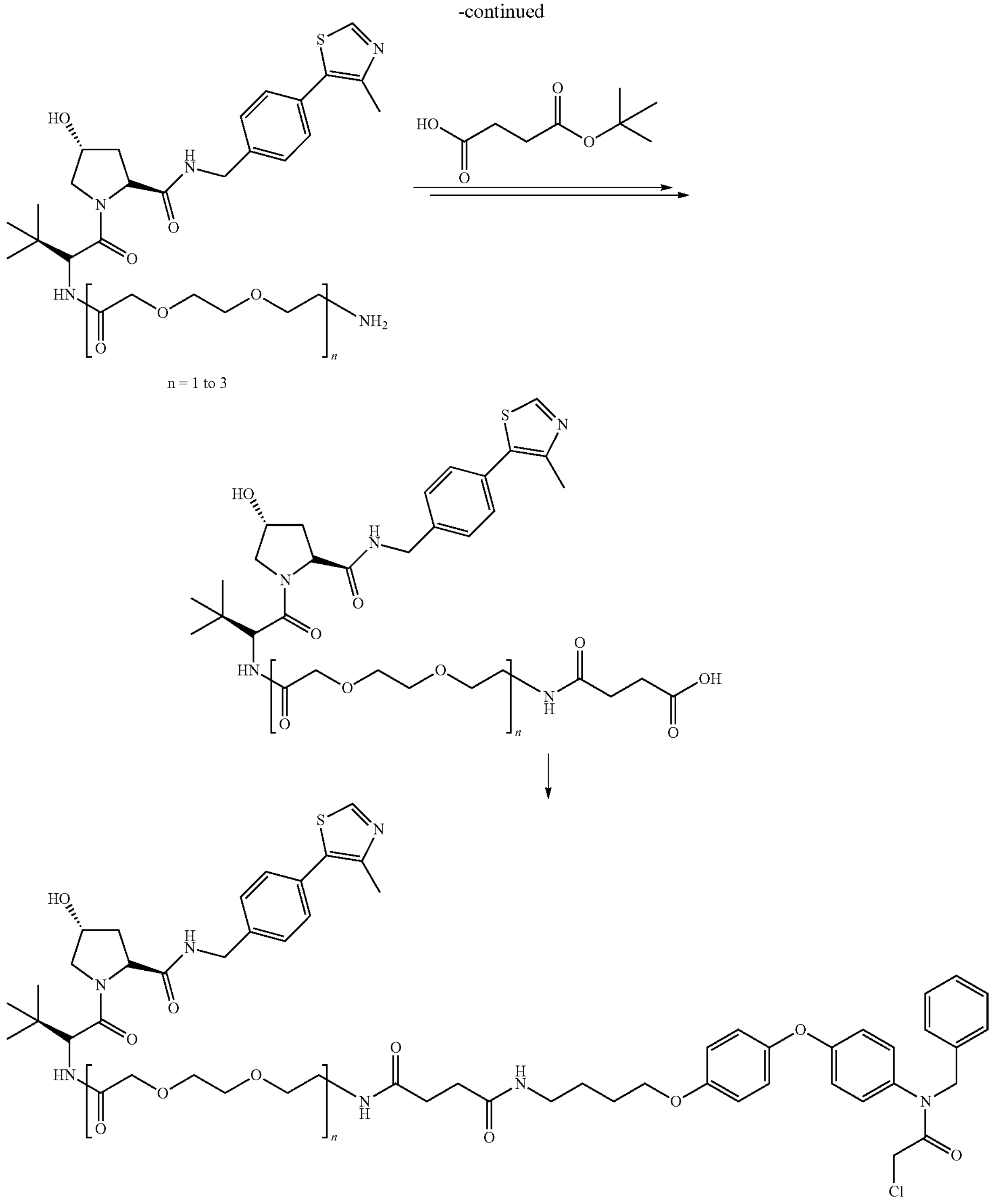

n = 1 to 3 n = 1 to 3

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A compound, including a salt an enantiomer, a diastereomer or a tautomer thereof, wherein said compound is represented by Formula I:

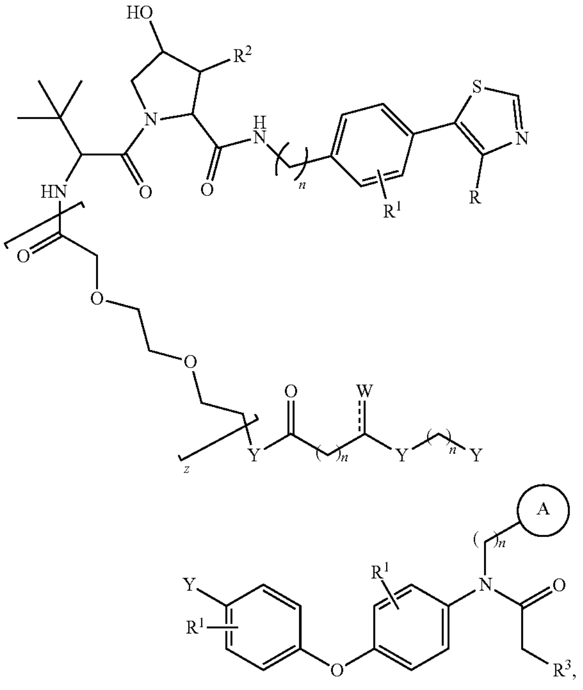

wherein:

each Y independently is selected from the group consisting of: NH, S, O and CH;

----- represents a single bond or a double bond;

W is selected from the group consisting of: H, NH, $NH_2$, S, SH, O, OH, $CH_2$ and CH;

each n independently represents an integer in a range from 1 to 10;

z represents an integer in a range from 0 to 6;

R, $R^2$ and $R^3$ each independently represents hydrogen, a hydroxy group, a methyl group, or a halo group;

each $R^1$ independently is selected from the group consisting of: a methyl group, an isopropyl group, a tert-butyl group, a ($C_2$-$C_{10}$) alkyl group, a substituted ($C_2$-$C_{10}$) alkyl group, a cycloalkyl group, an alkyne group, a substituted alkyne group, an alkylhydroxy group, an alkoxy group, an hydroxy group, a phenoxy group, a methoxy group, a carboxy group, a keto group, a halo group, a haloalkyl group, a nitro group, a cyano group, an amino group, an amide group, a thioalkoxy group, a thioalkyl group, a thiohydroxy group, trihalomethyl group, a sulfonyl group, a sulfoxy group, a sulfinyl group, a sulfonamide group, and any combination thereof; and A represents an aryl, a substituted aryl, a heteroaryl, a substituted heteroaryl, a $C_3$-$C_8$ cycloalkyl, a substituted $C_3$-$C_8$ cycloalkyl, an alkaryl, a substituted alkaryl, a bicyclic aromatic ring, a substituted bicyclic aromatic ring, a bicyclic heteroaryl, a substituted bicyclic heteroaryl, a bicyclic heterocyclyl, a substituted bicyclic heterocyclyl, a bicyclic cycloalkyl, a substituted bicyclic cycloalkyl, or a combination thereof.

2. The compound of claim 1, wherein A comprises any of:

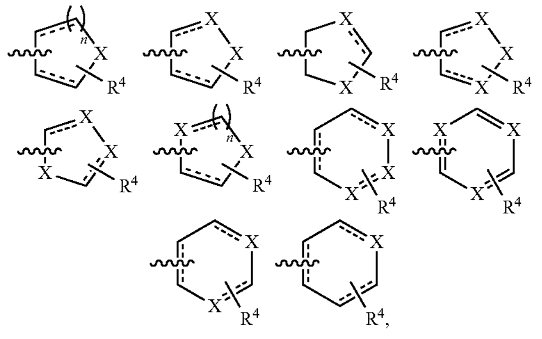

wherein:

each X independently represents CH, C, N, NH, S or O;

n is 1 or 2; and $R^4$ is absent or selected from the group consisting of: a methyl group, an isopropyl group, a tert-butyl group, a ($C_2$-$C_{10}$) alkyl group, a substituted ($C_2$-$C_{10}$) alkyl group, a cycloalkyl group, an alkyne group, a substituted alkyne group, an alkylhydroxy group, an alkoxy group, an hydroxy group, a phenoxy group, a methoxy group, a carboxy group, a keto group, a halo group, a haloalkyl group, a nitro group, a cyano group, an amino group, an amide group, a thioalkoxy group, a thioalkyl group, a thiohydroxy group, trihalomethyl group, a sulfonyl group, a sulfoxy group, a sulfinyl group, a sulfonamide group, and any combination thereof.

3. The compound of claim 1, wherein said A comprises any one of:

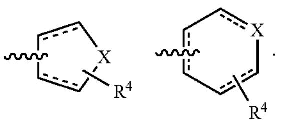

4. The compound of claim 1, wherein said z represents an integer in a range from 0 to 3.

5. The compound of claim 1, wherein said compound is represented by Formula II:

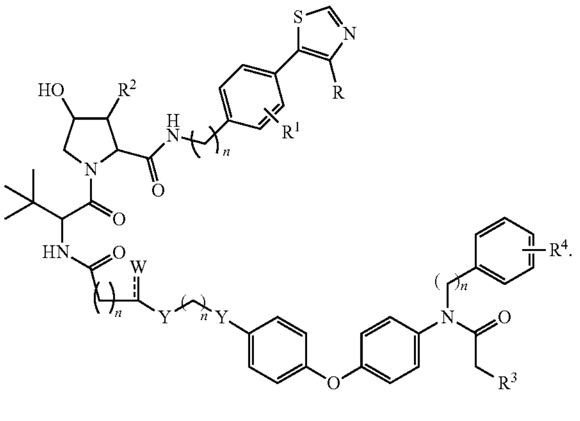

6. The compound of claim 1, wherein said compound is represented by Formula III:

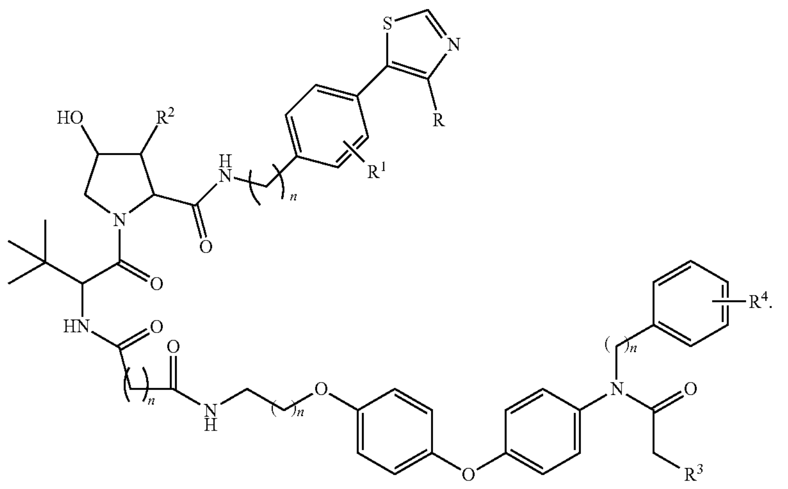

7. The compound of claim 1, wherein said compound is represented by Formula IV:

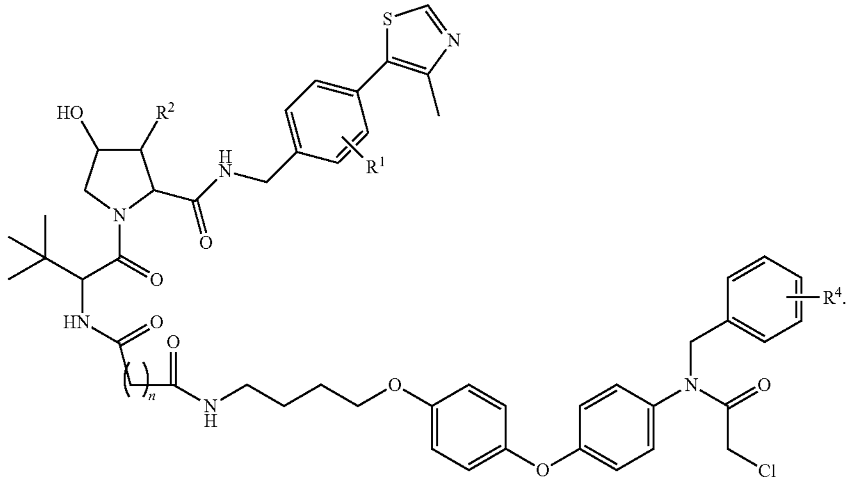

8. The compound of claim 1, wherein each of said n independently represents an integer in a range from 1 to 5.

9. The compound of claim 1, wherein said $R^1$ is selected from the group consisting of: a methyl group, an isopropyl group, a tert-butyl group, a ($C_2$-$C_{10}$) alkyl group, a substituted ($C_2$-$C_{10}$) alkyl group, a cycloalkyl group, a phenoxy group, a methoxy group, a carboxy group, a nitro group, and a trihalomethyl group.

10. The compound of claim 1, wherein said $R^2$ is a halo group.

11. The compound of claim 1, wherein said $R^4$ is selected from the group consisting of: a methyl group, an isopropyl group, a tert-butyl group, a ($C_2$-$C_{10}$) alkyl group, a substituted ($C_2$-$C_{10}$) alkyl group, a phenoxy group, a methoxy group, a halo group, a haloalkyl group, a nitro group, and a trihalomethyl group.

12. The compound of claim 1, wherein said compound is:

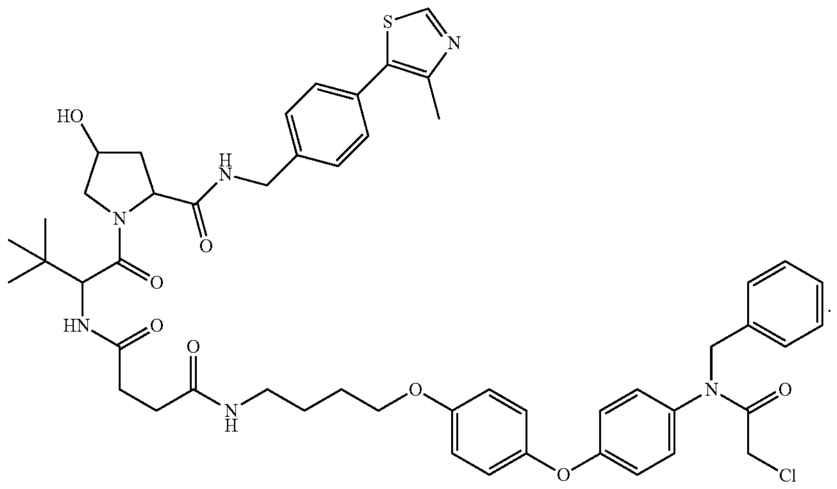 [SMILES: Cc1ncsc1-c1ccc(CNC(=O)C2CC(O)CN2C(=O)C(NC(=O)CCC(=O)NCCCCOc2ccc(Oc3ccc(N(Cc4ccccc4)C(=O)CCl)cc3)cc2)C(C)(C)C)cc1]

13. A pharmaceutical composition comprising a therapeutically effective amount of the compound of claim 1, and an acceptable carrier.

14. The compound of claim 1, characterized by increased binding affinity to Ring Finger Protein 4 (RNF4).

15. A method for treating or preventing development of a RNF4 related disorder, in a subject in need thereof, comprising administering to said subject a therapeutically effective amount the pharmaceutical composition of claim 13.

16. The method of claim 15, wherein said disorder is selected from the group comprising: cancer, inflammatory disorder, autoimmune disorder, or viral infection.

17. The method of claim 16, wherein said cancer is selected from the group consisting of: melanoma, squamous cell carcinoma breast cancer, colorectal cancer, osteosarcoma, lung cancer, ovarian cancer, prostate cancer, pancreatic cancer and hematological cancers.

* * * * *